(12) United States Patent
Guenther et al.

(10) Patent No.: US 8,470,776 B2
(45) Date of Patent: Jun. 25, 2013

(54) CONJUGATES OF DISORAZOLES AND THEIR DERIVATIVES WITH CELL-BINDING MOLECULES, NOVEL DISORAZOLE DERIVATIVES, PROCESSES OF MANUFACTURING AND USES THEREOF

(75) Inventors: Eckhard Guenther, Maintal (DE); Olaf Schaefer, Biberach an der Riss (DE); Michael Teifel, Weiterstadt (DE); Klaus Paulini, Maintal (DE)

(73) Assignee: Aeterna Zentaris GmbH, Frankfurt (DE)

( * ) Notice: Subject to any disclaimer, the term of this patent is extended or adjusted under 35 U.S.C. 154(b) by 515 days.

(21) Appl. No.: 12/728,050

(22) Filed: Mar. 19, 2010

(65) Prior Publication Data

US 2010/0317580 A1 Dec. 16, 2010

Related U.S. Application Data

(63) Continuation of application No. 11/850,747, filed on Sep. 6, 2007, now Pat. No. 7,741,277.

(60) Provisional application No. 60/842,357, filed on Sep. 6, 2006.

(30) Foreign Application Priority Data

Sep. 7, 2006 (EP) .................................... 06018750

(51) Int. Cl.
*A61K 31/42* (2006.01)
*A61K 38/24* (2006.01)
*A61K 38/31* (2006.01)

(52) U.S. Cl.
USPC ........ 514/10.1; 514/11.1; 514/19.2; 514/374; 514/375; 548/217

(58) Field of Classification Search
None
See application file for complete search history.

(56) References Cited

U.S. PATENT DOCUMENTS

| 2004/0106662 A1 | 6/2004 | Irschik et al. |
| 2006/0199252 A1 | 9/2006 | Irschik et al. |
| 2007/0021480 A1 | 1/2007 | Irschik et al. |
| 2008/0090758 A1 | 4/2008 | Guenther et al. |
| 2009/0311264 A1 | 12/2009 | Irschik et al. |

FOREIGN PATENT DOCUMENTS

| EP | 1 743 897 A1 | 1/2007 |
| WO | WO 2004/024149 A1 | 3/2004 |
| WO | WO 2005/112919 A2 | 12/2005 |
| WO | WO 2006/135371 A1 | 12/2006 |
| WO | WO 2007/009897 A1 | 1/2007 |

OTHER PUBLICATIONS

U.S. Appl. No. 12/728,075, filed Mar. 19, 2010, Guenter, et al.
FDA Label for Avastin U.S. BL 125085/169 Amendment: Bevacizumab Genentech, Inc. May 2009.
Wipf et al., "Cellular Analysis of Disorazole C1 and Structure-Activity Relationship of Analogs of the Natural Product", Chem Biol Drug Des 2006; 67:66-73.

*Primary Examiner* — Christina Bradley
(74) *Attorney, Agent, or Firm* — Oblon, Spivak, McClelland, Maier & Neustadt, L.L.P.

(57) ABSTRACT

The present invention provides conjugates of disorazoles and their derivatives with cell-binding molecules, such as peptides, proteins, hormones, blood proteins and antibodies. The present invention further provides novel disorazole derivatives and processes of manufacturing such conjugates and disorazole derivatives. These compounds can be used as medicaments for the treatment of physiological and/or pathophysiological conditions in mammals, in particular for the treatment of various tumors.

23 Claims, 17 Drawing Sheets

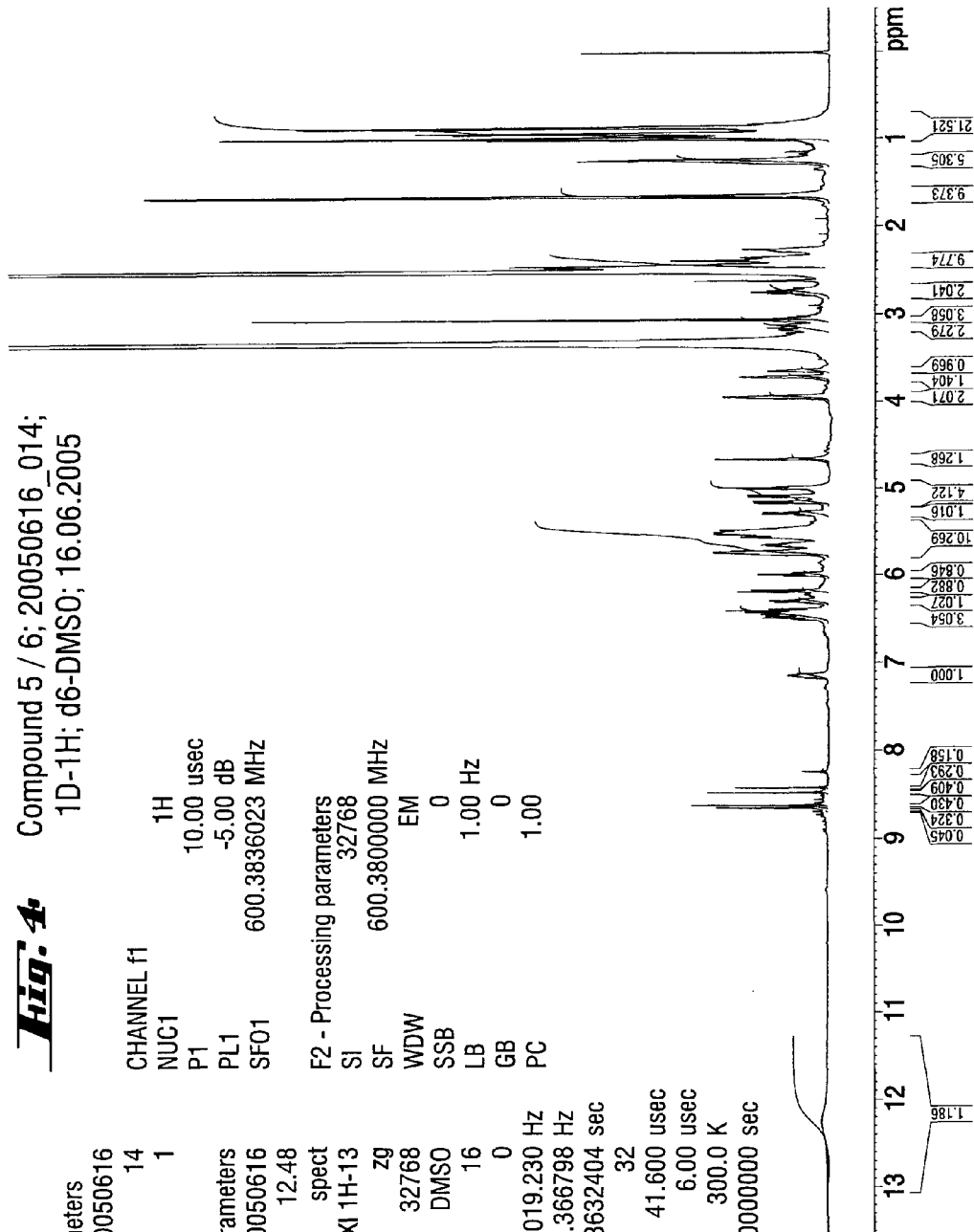

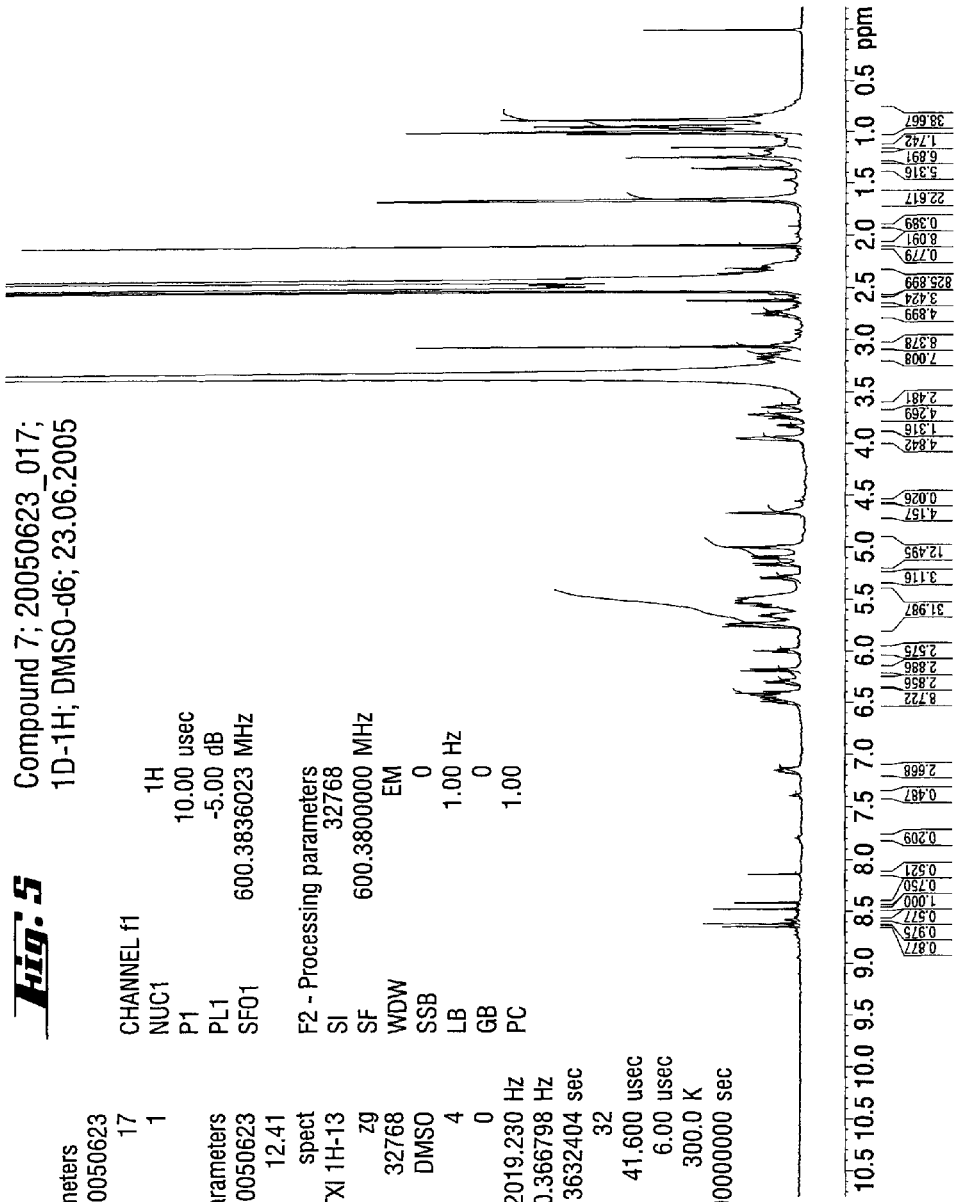

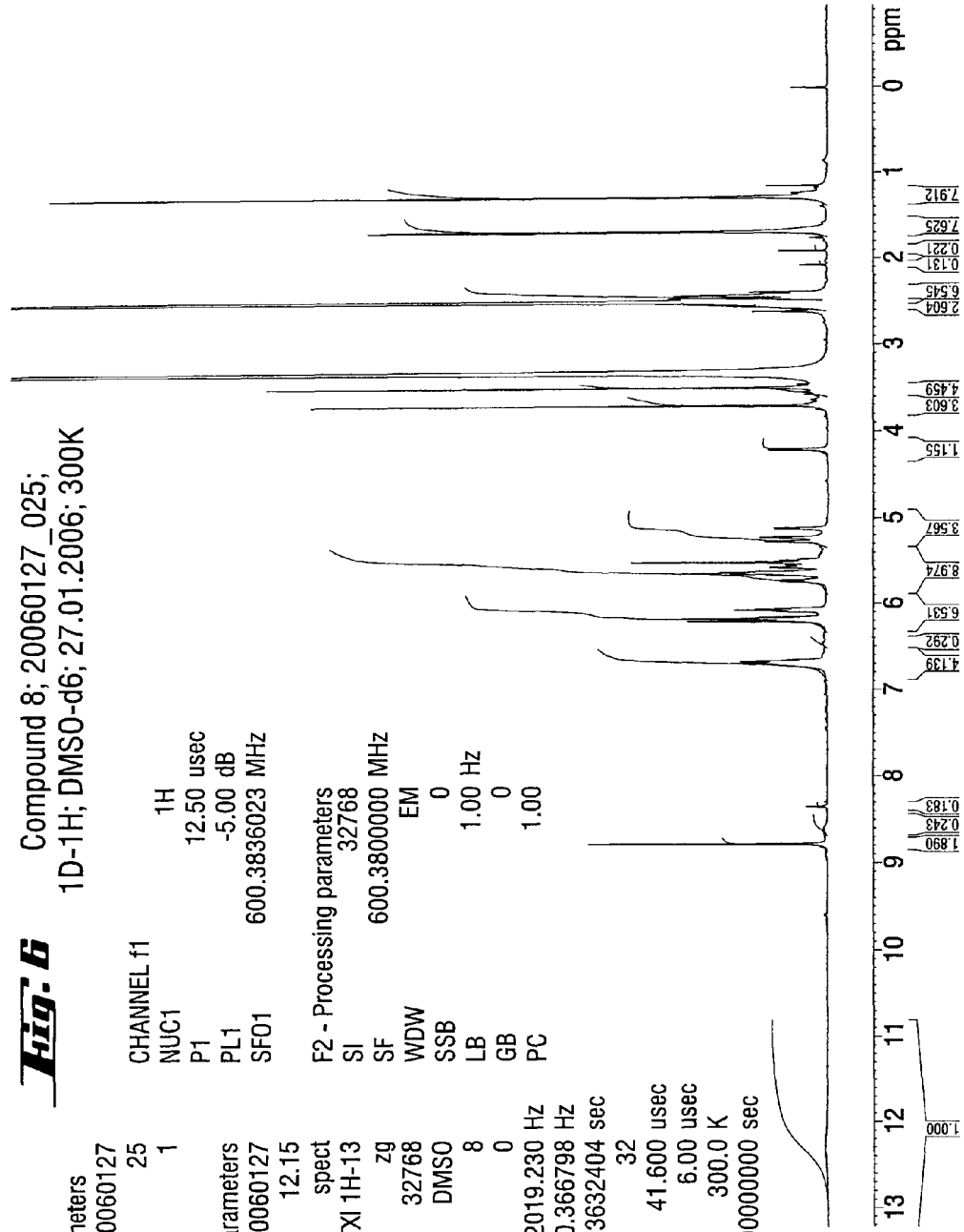

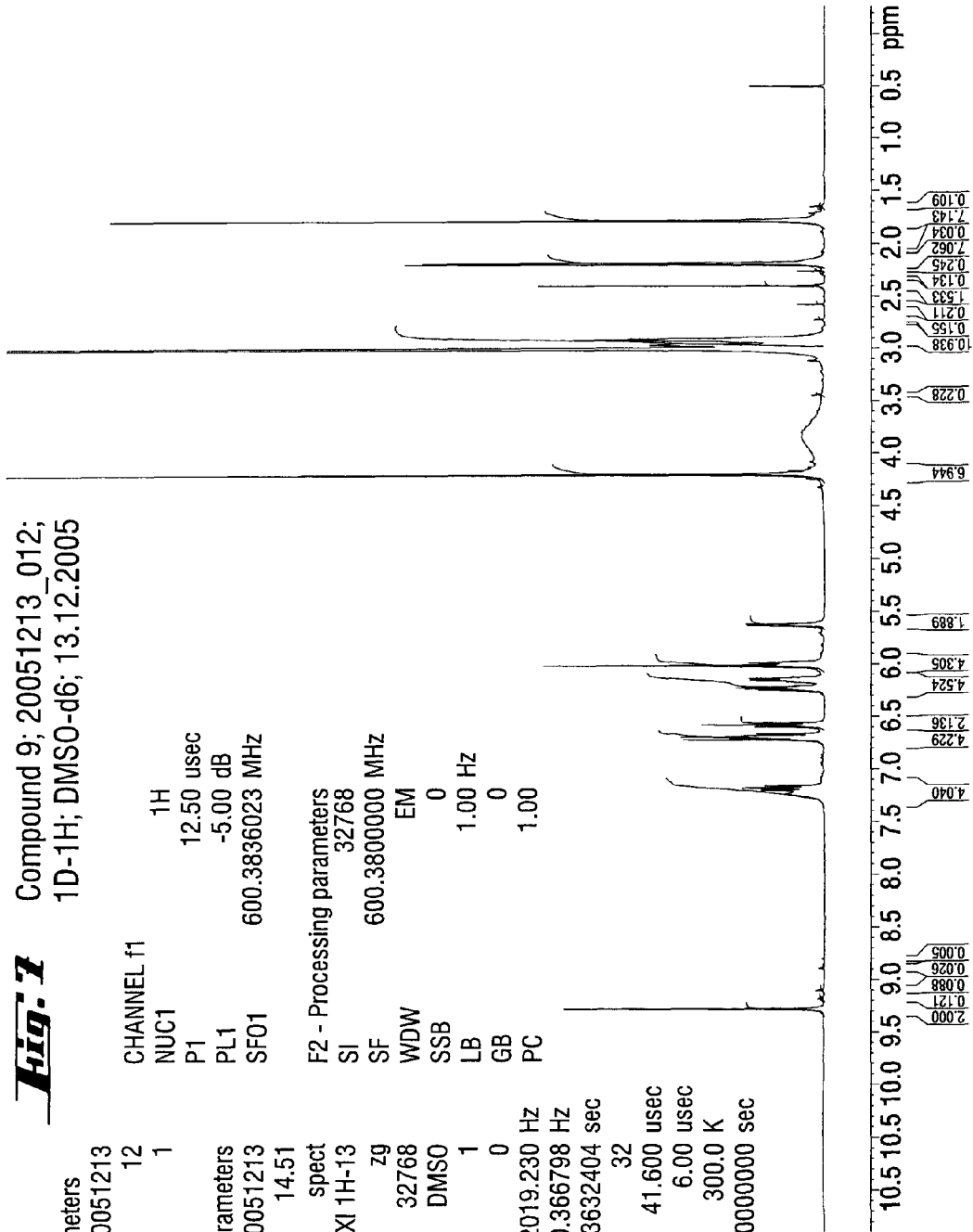

Fig. 8  Compound 10; 20051213_013; 1D-1H; DMSO-d6; 13.12.2005

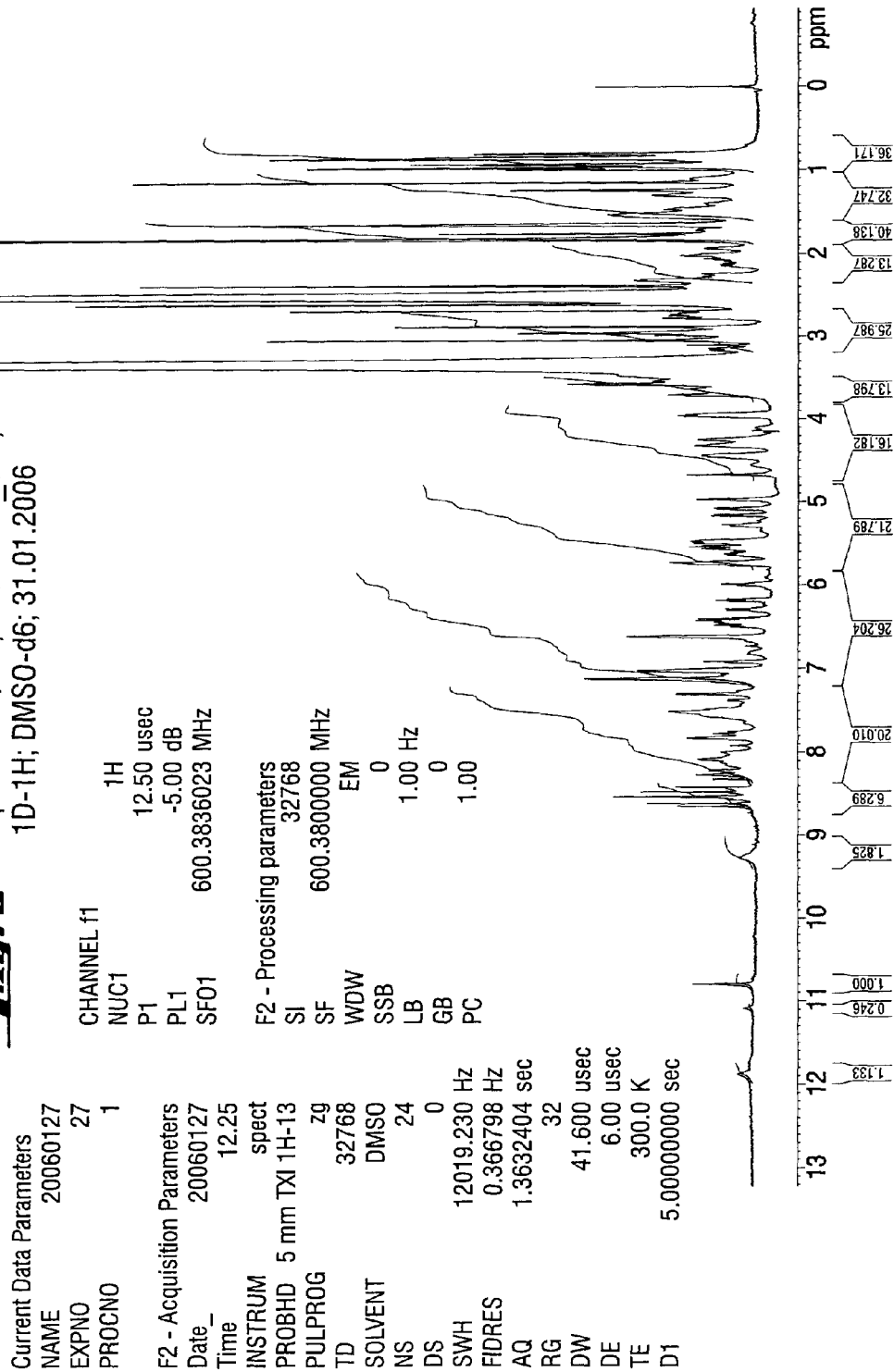

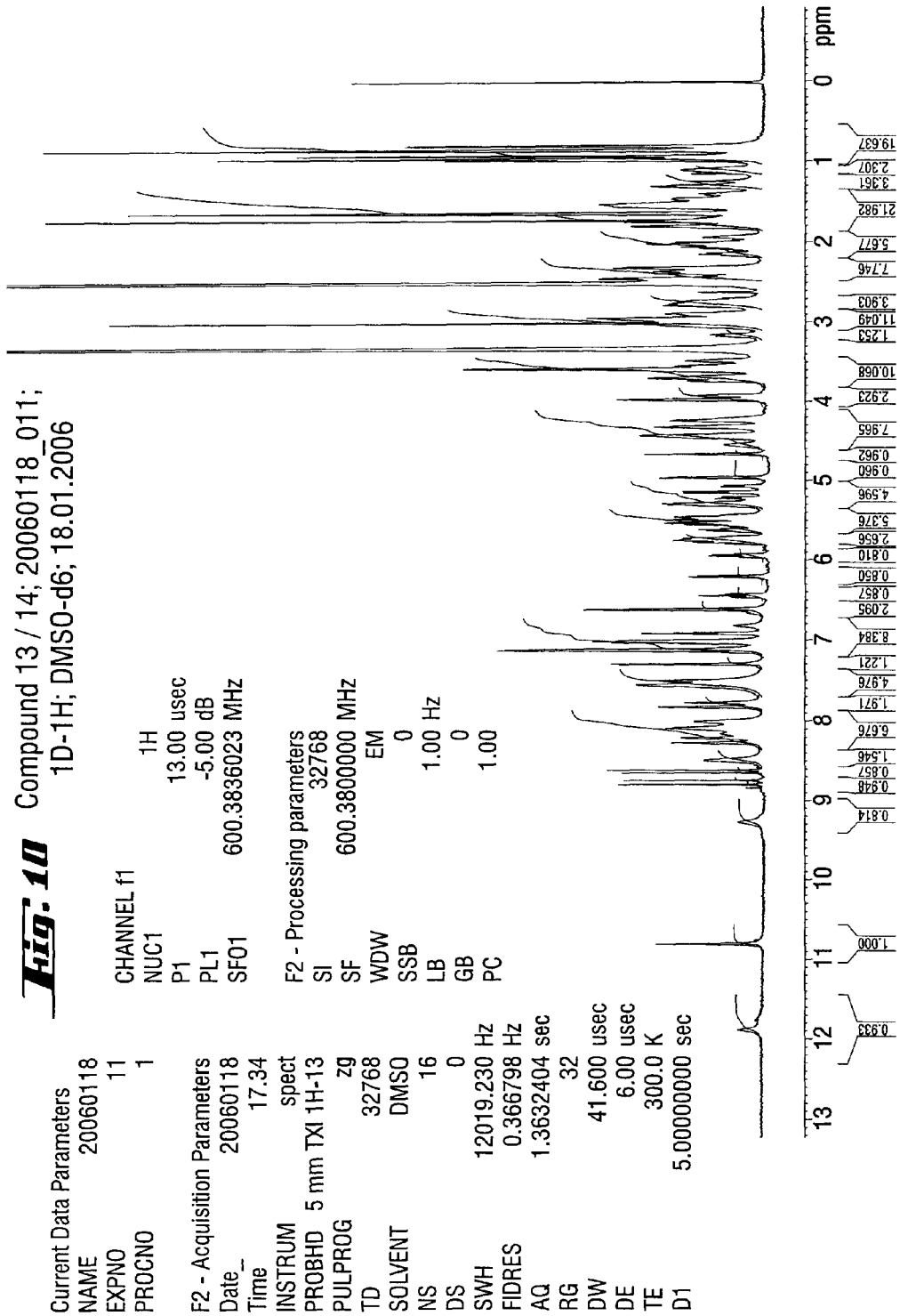

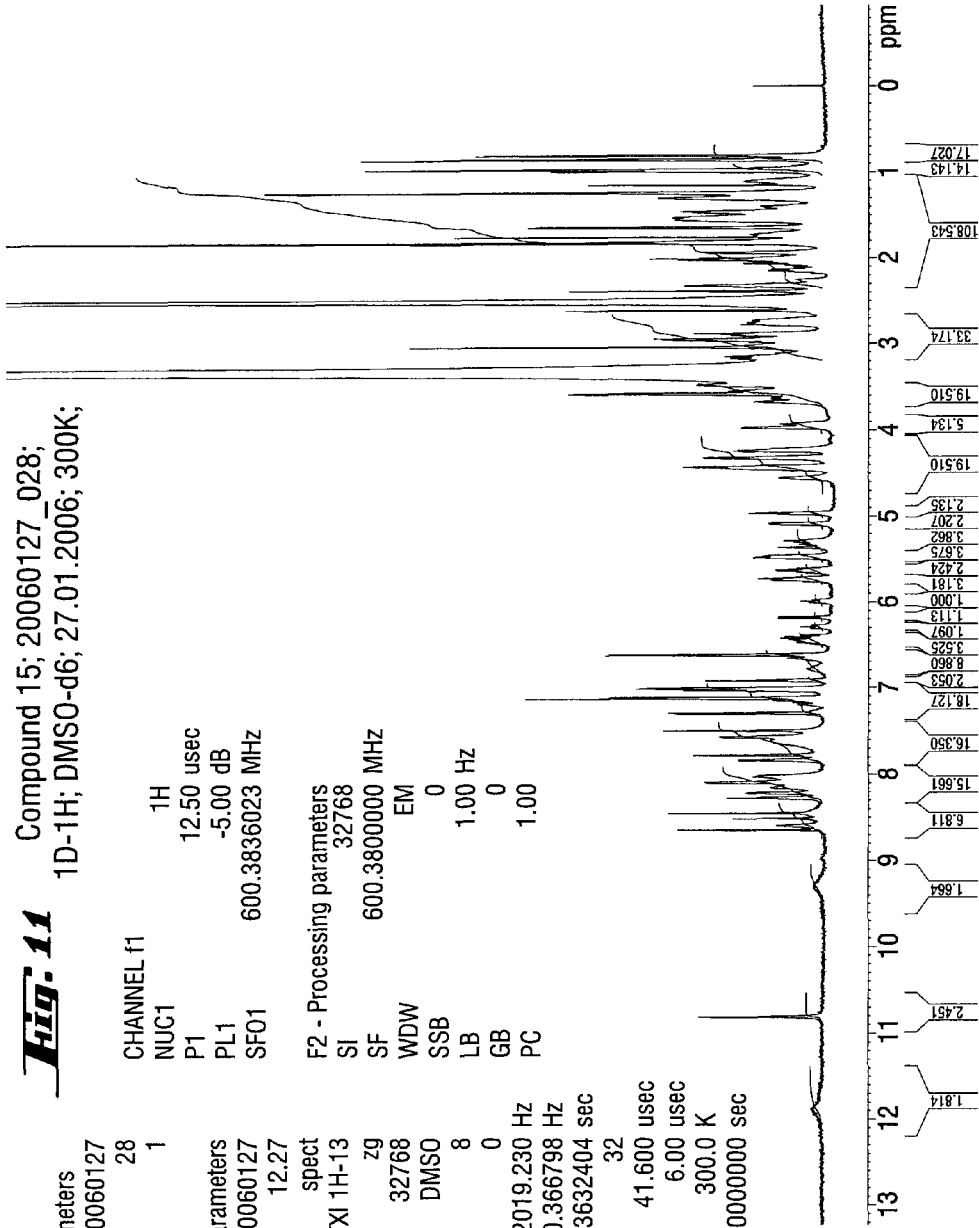

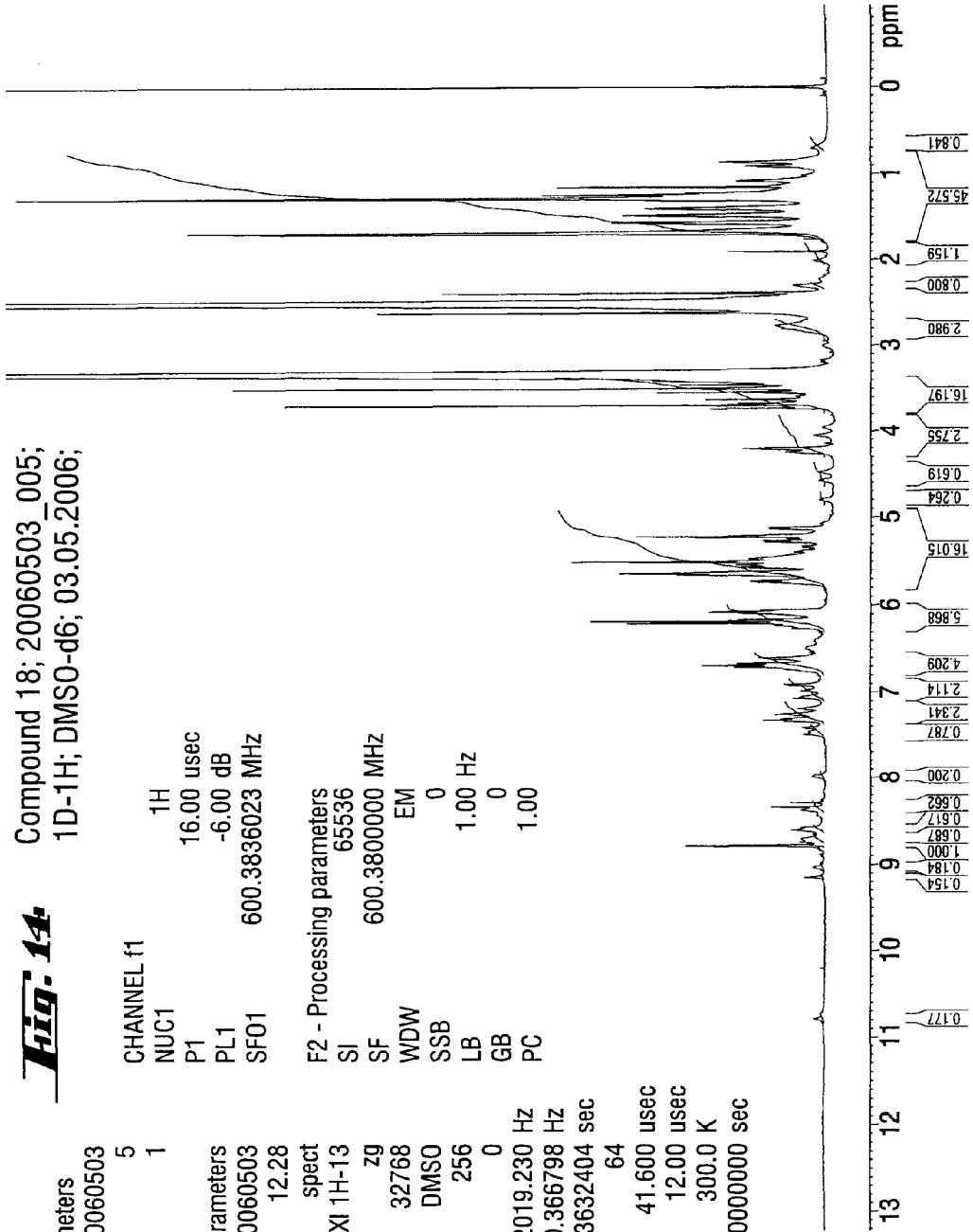

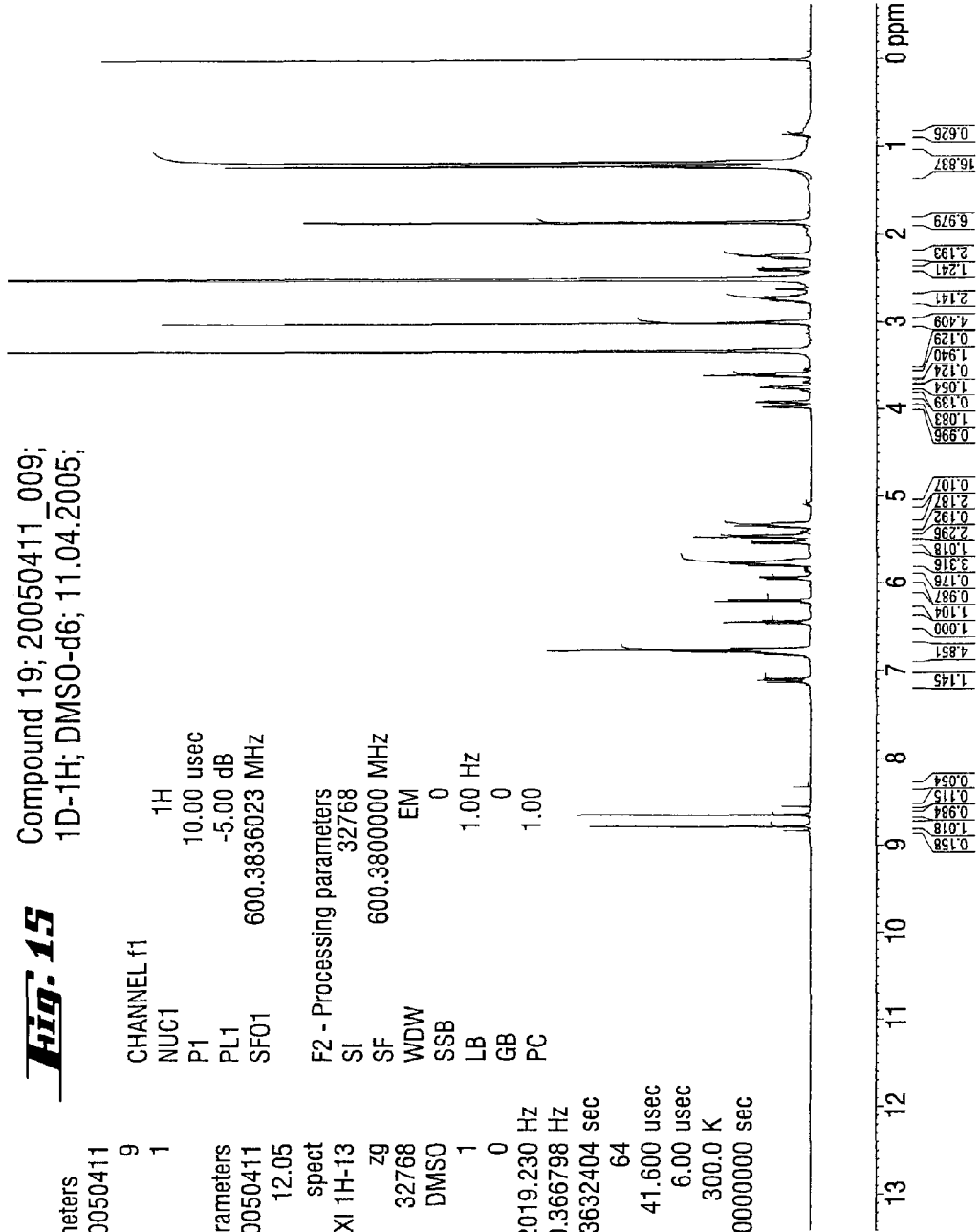

Fig. 16  Compound 20; 20050331_009; 1D-1H; DMSO-d6; 31.03.2005;

CONJUGATES OF DISORAZOLES AND THEIR DERIVATIVES WITH CELL-BINDING MOLECULES, NOVEL DISORAZOLE DERIVATIVES, PROCESSES OF MANUFACTURING AND USES THEREOF

CROSS-REFERENCE TO RELATED APPLICATIONS

The present application is a continuation of U.S. patent application Ser. No. 11/850,747, filed on Sep. 6, 2007, which claims priority to U.S. provisional application 60/842,357, filed on Sep. 6, 2006, and to European patent application 06018750.7, filed on Sep. 7, 2006, which are incorporated herein by reference in their entireties.

FIELD OF THE INVENTION

The invention relates to conjugates of disorazoles and their derivatives with cell-binding molecules, such as peptides and proteins, as well as novel disorazole derivatives and processes of manufacturing thereof. These compounds can be used as medicaments, in particular for the treatment of various tumors.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

For the next few years, a dramatic increase in oncoses and tumor-related cases of death is expected worldwide. In 2001, worldwide approximately 10 million people were suffering from cancer and over 6 million people died from this disease. The development of tumours is a fundamental disease of higher organisms in the plant kingdom, in the animal kingdom and in humans. The generally recognized multistep model of carcinogenesis assumes that as a result of accumulation of a number of mutations in an individual cell this is so modified in its proliferation and differentiation behaviour that finally, via benign intermediate stages, a malignant state with metastasis is reached.

The term cancer or tumor conceals a clinical picture with more than 200 various individual diseases. Oncoses can proceed in a benign or malignant manner. The most important tumours are those of the lung, the breast, the stomach, the neck of the uterus, the prostate, the head and neck, the large and small intestine, the liver and the blood system. There are great differences with respect to course, prognosis and therapy behaviour. More than the 90% of the cases recognized relate to solid tumours, which in particular in the advanced stage or on metastasis are treatable with difficulty or are untreatable. The three pillars of cancer control are still surgical removal, irradiation and chemotherapy. In spite of great advances it has not yet been possible to develop medicaments which bring about a marked prolongation of the survival time or even a complete cure in the widespread solid tumours. It is therefore meaningful to invent novel medicaments for the control of cancer.

Natural substances are an important source for novel lead structures in pharmaceutical research and are in some cases also directly suitable for the development of a novel medicament (Shu Y, J. Nat. Prod. 1998, 61: 1053-1071). It is known that many natural substances possess strongly cytotoxic action (Ram V J et al., Drug News Perspect 2001, 14(8): 465-482).

It is known that natural substances of the group consisting of the disorazoles are isolated from the bacterium of the strain *Sorangium cellulosum* So ce12 (Jansen R et al., Liebigs Ann. Chem. 1994, (8): 759-773).

In total, 29 disorazoles have been isolated and characterized physicochemically. For the disorazole A1, it was reported that it possesses an antiproliferative action in cell models (Irschik H et al., J. Antibiotics 1995, 48(1): 31-35; Elnakady Y A, Dissertation 2001, Technische Universität Carolo-Wilhelmina zu Braunschweig). However, use for the treatment of oncoses was neither disclosed nor suggested. A biological investigation of the other disorazoles was not carried out.

WO 2004/024149 reports that in particular disorazoles E1 and D1 possess cytotoxic action on various human tumor cell lines. In nano- and picomolar concentrations, the division, inter alia, of ovarian carcinoma, prostate carcinoma, glioblastoma, lung carcinoma and breast cancer cells is inhibited. The action of disorazoles E1 and D1 is in this case cell cycle-dependent. Even in nanomolar concentrations the cell cycle is held in the G2/M phase and the cancer cells are forced into apoptosis.

WO 2004/024149 further shows that the antiproliferative action of disorazoles is based, inter alia, on an effective inhibition of tubulin polymerization. Further, disorazole E1 is active against paclitaxel- and vindesine-resistant cell lines. This matters in particular, since disorazole A1 is unsuitable for use as a cytostatic (Hoefle G, Annual Report 1999/2000 of the Gesellschaft für Biotechnologische Forschung (GBF), pages 101/103).

Wipf and co-workers examined the cellular activity of disorazole C and the structure-activity relationship of eight of its analogues (Wipf et al., Chem. Biol. Drug Des. 2006, 67(1): 66-73).

Total Synthesis strategies for the synthesis of disorazoles A1 and C1 have been studied and thoroughly described (Hillier M C et al., J. Org. Chem. 2001, 66: 6037-6045; Hartung I V et al., Organic Letters 2002, 4(19): 3239-3242; Wipf P et al., J. Am. Chem. Soc. 2004, 126(47): 15346-15347).

Disorazole A1 has also been further characterized: it was shown that it acts as an antimitotic agent on tubulin polymerization and induces apoptosis in mammalian cells (Elnakady Y A et al., Biochem. Pharmacol. 2004, 67(5): 927-935). Furthermore, methanolysis products of disorazole A1 have been generated and studied for potential anti-proliferative activity (Hearn B R et al., J. Nat. Prod. 2006, 69(1): 148-150).

The following prior art documents are directed to the biosynthesis of disorazoles or related compounds: WO 2004/053065 describes polynucleotides that code for disorazole polyketide synthase. Schupp and co-workers characterized a *Sorangium cellulosum* gene cluster for the biosynthesis of the macrolide antibiotic Soraphen A (Schupp T et al., Journal of Bacteriology 1995, 177: 3673-3679). Biosynthetic genes for the disorazole biosynthesis were also characterized by Carvalho R et al. (Carvalho R et al., Gene 2005, 359: 91-98), Kopp and coworkers (Kopp M et al., Chembiochem. 2005, 6(7): 1277-1286) and WO 2006/075013.

However, none of the aforementioned prior art documents disclose or suggest conjugates of disorazoles.

U.S. Pat. No. 6,214,969 describes luteinizing hormone releasing hormone (LHRH) analogues with cytotoxic moieties. Such moieties can be either D-/L-Mel (4-[bis(2-chloroethyl)amino]-D/L-phenylalanine), cyclopropanealkanoyl, aziridine-2-carbonyl, epoxyalkyl, 1,4-naphthoquinone-5-oxycarbonyl-ethyl, doxorubicinyl (Doxorubicin, DOX), mitomicinyl (Mitomycin C), esperamycinyl or methotrexoyl.

Disorazoles, however, which are tubulin polymerization inhibitors and induce apoptosis, are not mentioned nor is the use of them rendered obvious.

U.S. Pat. No. 5,843,903 is directed to cytotoxic anthracycline analogues, in particular doxorubicin (DOX) or its daunosamine modified derivatives. Such cytotoxic moieties are conjugated to peptide hormones, such as LHRH, bombesin and somatostatin and their analogues.

Schally and Nagy review novel therapeutic modalities for various cancers that consist of the use of targeted cytotoxic analogues of LHRH, bombesin and somatostatin which contain doxorubicin (DOX) or 2-pyrrolino-DOX (Schally A V et al., Life Sciences 2003, 72: 2305-2320; Nagy A et al., Current Pharmaceutical Design 2005, 11: 1167-1180).

In all three foregoing references disorazoles are not disclosed nor suggested.

Other prior art documents that deal with cytotoxic agent containing conjugates comprise antibody-cytotoxic agent conjugates for use in cancer therapy (Chen J et al., Expert Opin. Drug Deliv. 2005, 2(5): 873-890), antibody-drug conjugates for use in oncology (Hamann P R, Expert Opin. Drug Deliv. 2005, 15(9): 1087-1103), multi-class-anticancer-drug conjugates for use in tumor targeting (Jaracz S et al., Bioorganic & Medicinal Chemistry 2005, 13: 5043-5054), vinca alkaloid cytotoxic agent-oligopeptide conjugates for the treatment of prostate cancer and/or benign prostate hyperplasia (WO 97/12624, WO 98/10651 and WO 99/02175), prodrug vinblastine-peptidyl conjugates for the treatment of prostate cancer (Brady S F et al., J. Med. Chem. 2002, 45: 4706-4715), enzyme- and proton-activated prodrugs for selective anticancer therapies (Tietze L F et al., Current Pharmaceutical Design 2003, 9: 2155-2175) and prodrugs of natural anthracyclines for use in antibody-directed enzyme prodrug therapy (Michel S et al., Studies in Natural Products Chemistry 2000, 21: 157-180).

Again, in all these foregoing references, disorazoles, however, which are tubulin polymerization inhibitors and induce apoptosis, are not mentioned nor is the use of them suggested.

DESCRIPTION OF THE INVENTION

The present invention has the object to provide conjugates of disorazoles and their derivatives with cell-binding molecules. It is another object of the underlying invention to provide novel disorazole derivatives. A further object of the present invention is to provide processes of manufacturing thereof. It is yet another object of the underlying invention to provide conjugates of disorazoles and their derivatives with cell-binding molecules and novel disorazole derivatives that can be used as medicaments, in particular for the treatment of various tumors.

The object of the invention has been surprisingly solved in one aspect by providing compounds according to formula (I)

$$C1\text{-}B1\text{-}A\text{-}B2\text{-}C2 \qquad (I),$$

wherein:
A is a disorazole moiety according to formula (II)

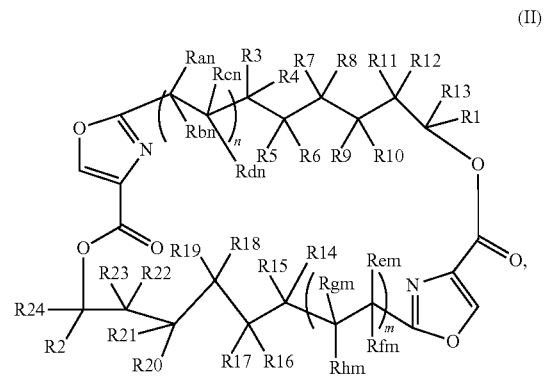

(II)

wherein:
Ra$_n$, Rb$_n$, Rc$_n$, Rd$_n$, Re$_m$, Rf$_m$, Rg$_m$, Rh$_m$, R1, R2, R3, R4, R5, R6, R7, R8, R9, R10, R11, R12, R13, R14, R15, R16, R17, R18, R19, R20, R21, R22, R23, R24 are independently from each other selected from the group consisting of hydrogen, alkyl, cycloalkyl, cycloalkyl-alkyl, aryl, heteroaryl, aryl-alkyl, heteroaryl-alkyl, heterocyclyl, heterocyclyl-alkyl, alkylsulfonyl, arylsulfonyl, aryl-alkylsulfonyl, halogen, hydroxyl, carbonyl, acetyl, carboxyl, carboxylester, amide, carbonate, carbamate, alpha-amino acid residues, beta-amino acid residues, alkoxyl, amino, imino, hydroxylamino, mono-alkylamino, di-alkylamino, hydrazinyl, cyano, alkyl-cyano, sulfhydryl, disulfidylalkyl and/or alkyl-sulfidyl which are optionally substituted in the alkyl, cycloalkyl, cycloalkyl-alkyl, aryl, heteroaryl, aryl-alkyl, heteroaryl-alkyl, heterocyclyl, heterocyclyl-alkyl, alkylsulfonyl, arylsulfonyl, aryl-alkylsulfonyl, carbonyl, acetyl, carboxyl, carboxylester, amide, carbonate, carbamate, alkoxyl, mono-alkylamino, di-alkylamino, alkyl-cyano, disulfidylalkyl and/or alkyl-sulfidyl group by 1, 2 or 3 substituents independently from each other selected from the group consisting of alkyl, cycloalkyl, cycloalkyl-alkyl, aryl, heteroaryl, aryl-alkyl, heteroaryl-alkyl, heterocyclyl, heterocyclyl-alkyl, alkylsulfonyl, arylsulfonyl, aryl-alkylsulfonyl, halogen, —F, —Cl, —Br, —I, —N$_3$, —NO$_2$, =O, =S =S(O)$_2$, hydroxyl, carbonyl, acetyl, carboxyl, carboxylester, —C(O)OH, —C(O)NH$_2$, amide, carbonate, carbamate, alpha-amino acid residues, beta-amino acid residues, alkoxyl, amino, imino, hydroxylamino, mono-alkylamino, di-alkylamino, hydrazinyl, cyano, alkyl-cyano, sulfhydryl, disulfidylalkyl and/or alkyl-sulfidyl;
optionally, any two adjacent radicals R of radicals Ra$_n$, Rb$_n$, Rc$_n$, Rd$_n$, Re$_m$, Rf$_m$, Rg$_m$, Rh$_m$, R1, R2, R3, R4, R5, R6, R7, R8, R9, R10, R11, R12, R13, R14, R15, R16, R17, R18, R19, R20, R21, R22, R23, R24 can form an atomic bond to yield a double bond or can form an epoxide (oxiran), aziran (aziridine), alkyl-, cycloalkyl-, cycloalkyl-alkyl-, heteroaryl-, aryl-alkyl-, heteroaryl-alkyl-, heterocyclyl- and/or heterocyclyl-alkyl-substituted aziran (aziridine), thiirane and/or thiirane-S-oxide group;
B1, B2 are independently from each other a linker, that covalently links A with C1 and/or C2;
C1, C2 are independently from each other a cell-binding molecule selected from the group consisting of peptide, peptide hormone, protein, protein hormone, receptor ligand, blood plasma protein, serum protein, antibody, antibody fragment;

n is 0, 1, 2, 3;

m is 0, 1, 2, 3.

For the avoidance of doubt, compounds according to above formulae (I) and (II), but also compounds according to below illustrated formulae (III) to (VI), can be present in the form of all possible double bond isomers, such as ..pure E- or Z-isomers or mixtures of these double bond isomers.

Further, regarding above formula (II), but also below illustrated formulae (III) to (VI), n/o=0 means that there are only 6 carbon atoms between the oxazole ring on the left hand side and the carboxy-group on the right hand side. As for n/o=1, 2, 3, this means that 8, 10 or 12 carbon atoms are included. Analogous, the same applies to m/p=0, 1, 2, 3, where, respectively 6, 8, 10 or 12 carbon atoms are included between the oxazole ring on the right and the carboxy-group on the left.

In a preferred embodiment, compounds according to above formulae (I) and (II) are provided, wherein A is a disorazole moiety according to formula (III)

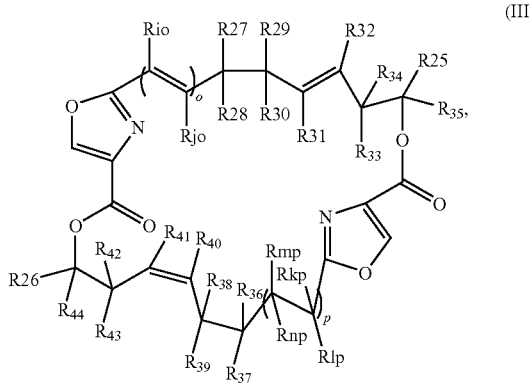

wherein:

$Ri_o$, $Rj_o$, $Rk_p$, $Rl_p$, $Rm_p$, $Rn_p$, R25, R26, R27, R28, R29, R30, R31, R32, R33, R34, R35, R36, R37, R38, R39, R40, R41, R42, R43, R44 are independently from each other selected from the group consisting of hydrogen, alkyl, cycloalkyl, cycloalkyl-alkyl, aryl, heteroaryl, aryl-alkyl, heteroaryl-alkyl, heterocyclyl, heterocyclyl-alkyl, alkylsulfonyl, arylsulfonyl, aryl-alkylsulfonyl, halogen, hydroxyl, carbonyl, acetyl, carboxyl, carboxylester, amide, carbonate, carbamate, alpha-amino acid residues, beta-amino acid residues, alkoxyl, amino, imino, hydroxylamino, mono-alkylamino, di-alkylamino, hydrazinyl, cyano, alkyl-cyano, sulfhydryl, disulfidylalkyl and/or alkyl-sulfidyl which are optionally substituted in the alkyl, cycloalkyl, cycloalkyl-alkyl, aryl, heteroaryl, aryl-alkyl, heteroaryl-alkyl, heterocyclyl, heterocyclyl-alkyl, alkylsulfonyl, arylsulfonyl, aryl-alkylsulfonyl, carbonyl, acetyl, carboxyl, carboxylester, amide, carbonate, carbamate, alkoxyl, mono-alkylamino, di-alkylamino, alkyl-cyano, disulfidylalkyl and/or alkyl-sulfidyl group by 1, 2 or 3 substituents independently from each other selected from the group consisting of alkyl, cycloalkyl, cycloalkyl-alkyl, aryl, heteroaryl, aryl-alkyl, heteroaryl-alkyl, heterocyclyl, heterocyclyl-alkyl, alkylsulfonyl, arylsulfonyl, aryl-alkylsulfonyl, halogen, —F, —Cl, —Br, —I, —N$_3$, —NO$_2$, =O, =S, =S(O)$_2$, hydroxyl, carbonyl, acetyl, carboxyl, carboxylester, —C(O)OH, —C(O)NH$_2$, amide, carbonate, carbamate, alpha-amino acid residues, beta-amino acid residues, alkoxyl, amino, imino, hydroxylamino, mono-alkylamino, di-alkylamino, hydrazinyl, cyano, alkyl-cyano, sulfhydryl, disulfidylalkyl and/or alkyl-sulfidyl;

optionally, any two adjacent radicals R of radicals $Ri_o$, $Rj_o$, $Rk_p$, $Rl_p$, $Rm_p$, $Rn_p$, R25, R26, R27, R28, R29, R30, R31, R32, R33, R34, R35, R36, R37, R38, R39, R40, R41, R42, R43, R44 can form an atomic bond to yield a double bond or can form an epoxide (oxiran), aziran (aziridine), alkyl-, cycloalkyl-, cycloalkyl-alkyl-, heteroaryl-, aryl-alkyl-, heteroaryl-alkyl-, heterocyclyl- and/or heterocyclyl-alkyl-substituted aziran (aziridine), thiirane and/or thiirane-5-oxide group;

o is 0, 1, 2, 3;

p is 0, 1, 2, 3.

In a further preferred embodiment, compounds according to above formulae (I), (II) and (III) and above embodiments are provided, wherein the linkers B1, B2 are independently from each other selected from the group consisting of: enzymatically cleavable linker, proteolytically cleavable linker, self-immolative linker, acid-labile linker, disulfide (exchange) linker, hydrolytically labile linker, bifunctional linker, multifunctional linker, ester linker, peptide linker, linker with 1, 2, 3, 4 or 5 amino acid residues, dipeptide linker, tetrapeptide linker, hydrazone linker, hydrazide linker, dicarbonic acid residue linker, poly-ethylenglycole (PEG) linker.

In yet a further preferred embodiment, compounds according to above formulae (I), (II) and (III) and above embodiments are provided, wherein the linkers B1, B2 are independently from each other selected from the group consisting of:

X1-alkyl-X2, X3-cycloalkyl-X4, X5-cycloalkyl-alkyl-X6, X7-alkyl-cycloalkyl-alkyl-X8, X9-aryl-X10, X11-aryl-alkyl-X12, X13-alkyl-aryl-alkyl-X14, X15-heteroaryl-X16, X17-heteroaryl-alkyl-X18, X19-alkyl-heteroaryl-alkyl-X20, X21-heterocyclyl-X22, X23-heterocyclyl-alkyl-X24, X25-alkyl-heterocyclyl-alkyl-X26, wherein X1, X2, X3, X4, X5, X6, X7, X8, X9, X10, X11, X12, X13, X14, X15, X16, X17, X18, X19, X20, X21, X22, X23, X24, X25, X26 are independently from each other selected from the group consisting of O—, S—, S—S—, C(O)O—, C(O)—, OC(O)O—, C(O)NH—, OC(O)NH—, NHC(O)—, NHC(O)O—, NH—, NY1-, C(O)NY2-, OC(O)NY3-, NY4C(O)—, NY5C(O)O—, C=N—NH—, NH—N=C—, C=N—NY6-, NY7-N=C—, wherein Y1, Y2, Y3, Y4, Y5, Y6, Y7 are independently from each other selected from the group consisting of alkyl, cycloalkyl, cycloalkyl-alkyl, aryl, heteroaryl, aryl-alkyl, heteroaryl-alkyl, heterocyclyl, heterocyclyl-alkyl, halogen, —F, —Cl, —Br, —I, —N$_3$, —NO$_2$, hydroxyl, alkoxyl, amino, imino, hydroxylamino, hydrazinyl, cyano, alkyl-cyano, sulfhydryl;

oxalyl, malonyl, succinyl, glutaryl, adipinyl, maleinyl, fumaryl;

and linkers based on the following molecules:

Gly-Phe-Leu-Gly, Phe-Lys, Val-Cit (citrulline);

1,4-bis(aminomethyl-)-cyclohexane, 1,4-bis(aminomethyl-)-cycloheptane, 1,3-bis(aminomethyl-)-cyclopentane, 1-amino-4-(aminomethyl)-cyclohexane, 1,4-diaminocyclohexane, 1,4-bis(aminomethyl)bicycle[2.2.2]octane, gamma-maleimidocaproylhydrazide, 4-hydrazinosulfonylbenzoic acid, SMCC bifunctional linker, MDS (methyldisulfanyl), PEG2, PEG3, PEG7;

Lilly Linker:

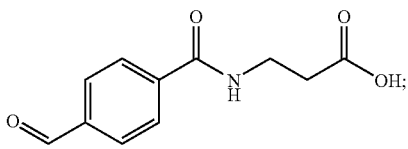 [SMILES: O=Cc1ccc(C(=O)NCCC(=O)O)cc1]

Lilly BAMME Linker:

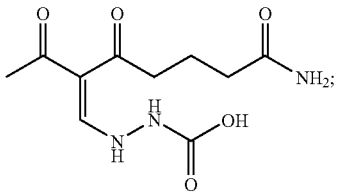 [SMILES: CC(=O)/C(=C/NNC(=O)O)C(=O)CCCC(N)=O]

Lilly BAP Linker:

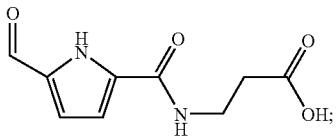 [SMILES: O=Cc1ccc(C(=O)NCCC(=O)O)[nH]1]

cis-Aconitic Linker:

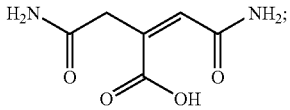 [SMILES: NC(=O)/C=C(/CC(N)=O)C(=O)O]

PABC1 Linker:

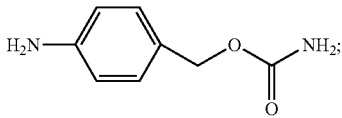 [SMILES: NC(=O)OCc1ccc(N)cc1]

PABC2 Linker:

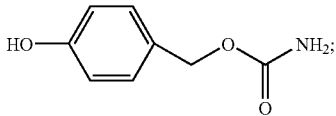 [SMILES: NC(=O)OCc1ccc(O)cc1]

PABC3 Linker:

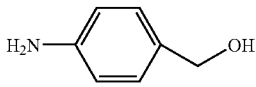

PABC4 Linker:

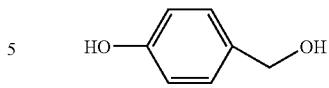

PABC5 Linker:

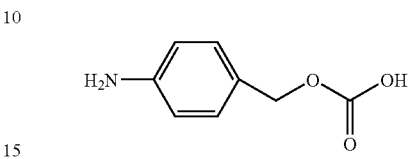

PABC6 Linker:

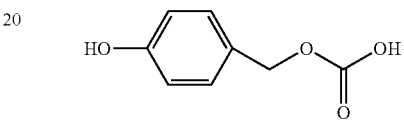

The term linker in the scope of the present invention is intended to comprise any linker, linking moiety, spacer and other molecules/moieties that are known to the skilled artisan and are suitable to link the disorazoles moieties A to the cell-binding molecules C1 and/or C2.

It is within the knowledge of a skilled artisan to use appropriate activated forms and/or radicals of above preferred linker molecules for the generation of the final conjugates.

Relevant prior art literature regarding suitable linkers comprises for example Michel S et al., Studies in Natural Products Chemistry 2000, 21: 157-180; Tietze L F et al., Current Pharmaceutical Design 2003, 9: 2155-2175; Brady S F et al., J. Med. Chem. 2002, 45: 4706-4715; WO 99/02175; Jaracz S et al., Bioorganic & Medicinal Chemistry 2005, 13: 5043-5054; Hamann P R, Expert Opin. Drug Deliv. 2005, 15(9): 1087-1103; Chen J et al., Expert Opin. Drug Deliv. 2005, 2(5): 873-890; U.S. Pat. No. 5,843,903, U.S. Pat. No. 6,214,969.

In another preferred embodiment, compounds according to above formulae (I), (II) and (III) and above embodiments are provided, wherein the cell-binding molecules C1, C2 are independently from each other selected from the group consisting of: octamer peptide, nonamer peptide, decamer peptide, LHRH analogue, LHRH agonist, LHRH antagonist, bombesin, bombesin analogue, bombesin antagonist, somatostatin, somatostatin analogue, serum albumin, human serum albumin (HSA), Galanin receptor ligand, GAL1 receptor ligand, GAL2 receptor ligand, galanin (Chemical Abstract Services Registry No. 119418-04-1) and analogues, somatostatin receptor ligand, sst1 receptor ligand, sst2 receptor ligand, sst4 receptor ligand, sst5 receptor ligand, somatostatin (Chemical Abstract Services Registry No. 38916-34-6) and analogues, octreotide (Chemical Abstract Services Registry No. 83150-76-9) and analogues, RC-121 (D-Phe-Cys-Tyr-D-Trp-Lys-Val-Cys[cyclic(2→7)disulfide]-Thr-NH$_2$; Chemical Abstract Services Registry No. 99660-13-6) and analogues, bombesin receptor ligand, BB1 receptor ligand, BB2 receptor ligand, BB3 receptor ligand, gastrin-releasing-peptide-receptor (GRP-R) ligand, Bombesin (Bn; Chemical Abstract Services Registry No. 31362-50-2) and analogues, gastrin-releasing-peptide (GRP) and analogues, neuromedin B (Chemical Abstract Services Registry No. 102577-19-5) and analogues, [D-Tyr$^6$,beta-Ala$^{11}$,Phe$^{13}$,Nle(Norleucin)$^{14}$]-Bombesin(6-14) and analogues, RC-3095 (H-D-Tpi-Gln- Trp-Ala-Val-Gly-His-Leu-psi-Leu-NH$_2$; Chemical Abstract Services Registry No. 138147-78-1; U.S. Pat. No. 5,244,883; U.S. Pat. No. 5,369,094) and analogues, Gln-Trp-Ala-Val-Gly-His-Psi-Leu-Leu-NH$_2$ (U.S. Pat. No. 5,843,903) and analogues, Gonadotropin-releasing-hormone receptor (GnRH-R) ligand, GnRH-R type I ligand, GnRH-R type II ligand, luteinizing hormone releasing hormone (LHRH; Glp-His-Trp-Ser-Tyr-Gly-Leu-Arg-Pro-Gly-NH$_2$) and analogues, [D-Lys$^6$]-LHRH, Triptorelin ([D-Trp$^6$]-LHRH; Chemical Abstract Services Registry No. 57773-63-4) and analogues, Histrelin (6-[1-(phenylmethyl)-D-histidine]-9-(N-ethyl-L-prolinamide)-10-deglycinamide-LHRH; Chemical Abstract Services Registry No. 76712-82-8) and analogues, Buserelin (6-[O-(1,1-dimethylethyl)-D-serine]-9-(N-ethyl-L-prolinamide)-10-deglycinamide-LHRH; Chemical Abstract Services Registry No. 57982-77-1) and analogues, Leuprorelin (6-D-leucine-9-(N-ethyl-L-prolinamide)-10-deglycinamide-LHRH; Chemical Abstract Services Registry No. 53714-56-0) and analogues, Goserelin (6-[O-(1,1-dimethylethyl)-D-serine]-LHRH-2-(aminocarbonyl)hydrazide; Chemical Abstract Services Registry No. 65807-02-5) and analogues, Nafarelin (6-[3-(2-naphthalenyl)-D-alanine]-LHRH; Chemical Abstract Services Registry No. 76932-56-4) and analogues, LHRH-II(Pyr-His-Trp-Ser-His-Gly-Trp-Tyr-Pro-Gly-NH$_2$) and analogues, Cetrorelix (Chemical Abstract Services Registry No. 120287-85-6) and analogues, Teverelix/Antarelix (Chemical Abstract Services Registry No. 144743-92-0) and analogues, Ozarelix (D-63153; Chemical Abstract Services Registry No. 295350-45-7) and analogues, Abarelix (Chemical Abstract Services Registry No. 183552-38-7) and analogues, Degarelix (Chemical Abstract Services Registry No. 214766-78-6) and analogues, Detirelix (Chemical Abstract Services Registry No. 89662-30-6) and analogues, Ganirelix (Chemical Abstract Services Registry No. 124904-93-4) and analogues, Iturelix/Antide (Chemical Abstract Services Registry No. 112568-12-4) and analogues, GPR54 receptor ligands, Kisspeptins and analogues, kisspeptin-10/Kp-10 (Chemical Abstract Services Registry No. 374675-21-5) and analogues, kisspeptin-13/Kp-13 (Chemical Abstract Services Registry No. 374675-18-0) and analogues, metastin (Chemical Abstract Services Registry No. 388138-21-4) and analogues, neurokinin receptor ligand, NK1/NKA receptor ligand, NK2/NKB receptor ligand, NK3 receptor ligand, substance P(H-Arg-Pro-Lys-Pro-Gln-Gln-Phe-Phe-Gly-Leu-Met-NH$_2$); Chemical Abstract Services Registry No. 33507-63-0) and analogues, H-Asp-Ser-Phe-Val-Gly-Leu-Nle-NH$_2$ and analogues, [Sar$^9$, Met(O$_2$)$^{11}$]-substance P and analogues, [Nle$^{10}$]-Neurokinin A(4-10) and analogues, [MePhe$^7$]-Neurokinin B and analogues, [beta-Ala$^8$]-Neurokinin A(4-10) and analogues, Bradykinin receptor ligand, B1 receptor ligand, B2 receptor ligand, Bradykinin (H-Arg-Pro-Pro-Gly-Phe-Ser-Pro-Phe-Arg-OH; Chemical Abstract Services Registry No. 58-82-2) and analogues, desArg$^9$-[Leu$^8$]-Bradykinin and analogues, desArg$^9$-Bradykinin and analogues, LysdesArg$^9$-Bradykinin and analogues, LysdesArg$^9$-[Leu$^8$]-Bradykinin and analogues, [Hyp$^3$,Tyr(Me)$^8$]-Bradykinin and analogues, D-Arg [Hyp$^3$,D-Phe$^7$,Leu$^8$]-Bradykinin and analogues, BKM 718 (Chemical Abstract Services Registry No. 259883-69-7) and analogues, BKM 822 (Chemical Abstract Services Registry No. 259884-10-1) and analogues, BKM 570 (Chemical Abstract Services Registry No. 259885-54-6) and analogues, BKM-638 (Chemical Abstract Services Registry No. 259885-81-9) and analogues, GHS receptor ligand, Ghrelin (Chemical Abstract Services Registry No. 304853-26-7) and analogues, Hexarelin (Chemical Abstract Services Registry No. 140703-51-1) and analogues, GHRP-1 (Chemical Abstract Services Registry No. 141925-59-9) and analogues, GHRP-2 (Chemical Abstract Services Registry No. 158861-67-7) and analogues, GHRP-6 (His-D-Trp-Ala-Trp-D-Phe-Lys-NH$_2$; Chemical Abstract Services Registry No. 87616-84-0) and analogues, D-Lys$^3$-GHRP-6 and analogues, EP-1572 (Chemical Abstract Services Registry No. 381231-18-1) and analogues, des-octanoyl ghrelin and analogues, relaxin receptor ligand, LGR7 receptor ligand, LGR8 receptor ligand, relaxin (Chemical Abstract Services Registry No. 9002-69-1) and analogues, insulin-like 3 peptide (INSL3; Chemical Abstract Services Registry No. 166515-61-3) and analogues, glucagon-like peptide 1 receptor ligand, glucagon receptor ligand, glucagon like peptide-1 (GLP-1; Chemical Abstract Services Registry No. 89750-14-1) and analogues, glucagon like peptide-2 (GLP-2; Chemical Abstract Services Registry No. 116469-36-4) and analogues, Cholecystokinin receptor ligand, CCK1/CCKA receptor ligand, CCK2/CCKB receptor ligand, CCKC receptor ligand, Cholecystokinin (Chemical Abstract Services Registry No. 9011-97-6) and analogues, neuropeptide Y (NPY) receptor ligand, NPY1 receptor ligand, NPY2 receptor ligand, NPY3 receptor ligand, neuropeptide Y (NPY; Chemical Abstract Services Registry No. 82785-45-3) and analogues, [Leu$^{31}$,Pro$^{34}$]NPY and analogues, NPY-(13-36) and analogues, peptide yy (Chemical Abstract Services Registry No. 106388-42-5) and analogues, Endothelin receptor ligand, ETA receptor ligand, ETB receptor ligand, endothelin 1 (Chemical Abstract Services Registry No. 123626-67-5) and analogues, endothelin 2 (Chemical Abstract Services Registry No. 122879-69-0) and analogues, endothelin 3 (Chemical Abstract Services Registry No. 125692-40-2) and analogues, vasoactive intestinal peptide receptor (VPAC1, VIP1) ligand, VPAC2/VIP2 receptor ligand, PAC1/PACAP receptor ligand, PACAP(1-27) (Chemical Abstract Services Registry No. 137061-48-4) and analogues, PACAP(1-38) (Chemical Abstract Services Registry No. 137061-48-4) and analogues, PACAP(6-27) (Chemical Abstract Services Registry No. 137061-48-4) and analogues, PACAP(6-38) (Chemical Abstract Services Registry No. 137061-48-4) and analogues, Vasoactive intestinal polypeptide (VIP) (Chemical Abstract Services Registry No. 37221-79-7) and analogues, VIP (6-28) (Chemical Abstract Services Registry No. 37221-79-7) and analogues, [(Ac-His$^1$,D-Phe$^2$,Lys$^{15}$,Arg$^{16}$,Leu$^{27}$)-VIP (1-7)-GRF (8-27)] and analogues, [Lys$^1$,Pro$^{2,5}$,Arg$^{3,4}$,Tyr$^6$]-VIP and analogues, VEGF receptor ligand, NP-1 receptor ligand, neuropilin-1 receptor ligand, vascular endothelial growth factor (VEGF; Chemical Abstract Services Registry No. 127464-60-2) and analogues, Fibroblast growth factor receptor ligand, Fibroblast growth factor (FGF; Chemical Abstract Services Registry No. 62031-54-3) and analogues and preferably are selected from the group consisting of: octamer peptide, nonamer peptide, decamer peptide, luteinizing hormone releasing hormone (LHRH), [D-Lys$^6$]-LHRH, LHRH analogue, LHRH agonist, Triptorelin ([D-Trp$^6$]-LHRH), LHRH antagonist, bombesin, bombesin analogue, bombesin antagonist, somatostatin, somatostatin analogue, serum albumin, human serum albumin (HSA).

All these cell-binding molecules and their analogues are well known in the prior art. Where available, Chemical Abstract Services (CAS) Registry Numbers are given. However, it is not intended to restrict the scope of cell-binding molecules to only those referred to by the respective CAS registry number. That is by the cell-binding molecule term any possible structural and/or functional variant/family member is intended to be comprised.

By the term analogue referring to cell-binding molecule any structurally and/or functionally related cell-binding molecule analogue that is known to the skilled artisan from the prior art is intended to be within the scope of the present invention. Non-limiting examples are for instance analogues of LHRH, such as triporelin, cetrorelix and others.

The term analogue referring to cell-binding molecule is also intended to comprise, if applicable, agonists and antagonists of the cell-binding molecule in question, i.e. the term LHRH analogue does comprise LHRH agonists and LHRH antagonists in the scope of the present invention.

In another preferred embodiment of the present invention, compounds according to above formulae (I), (II) and (III) and above embodiments are provided, wherein the linkers B1 and B2 are identical and the cell-binding molecules C1 and C2 are identical.

In another preferred embodiment of the present invention, compounds according to above formulae (I), (II) and (III) and above embodiments are provided, wherein the linker B2 and the cell-binding molecule C2 are not present, according to formula (IV)

C1-B1-A                  (IV).

In yet another preferred embodiment of the present invention, compounds according to above formulae (I), (II) and (III) and above embodiments are provided, wherein:
A is a disorazole moiety according to formula (III);
$Ri_o$, $Rj_o$, $Rk_p$, $Rm_p$, R28, R30, R31, R32 R33, R34, R35, R36, R38, R40, R41, R42, R43, R44 are hydrogen;
$Rl_p$, $Rn_p$ together form a double bond or are independently selected from the group consisting of hydrogen, alkoxyl;
R27, R29 together form a double bond or an epoxide (oxiran);
R37, R39 together form a double bond or an epoxide (oxiran);

R25, R26 are independently from each other selected from the group consisting of: alkyl which is optionally substituted in the alkyl group by 1, 2 or 3 substituents independently from each other selected from the group consisting of alkyl, cycloalkyl, cycloalkyl-alkyl, aryl, heteroaryl, aryl-alkyl, heteroaryl-alkyl, heterocyclyl, heterocyclyl-alkyl, alkylsulfonyl, arylsulfonyl, aryl-alkylsulfonyl, halogen, —F, —Cl, —Br, —I, —$N_3$, —$NO_2$, =O, =S, =$S(O)_2$, hydroxyl, carbonyl, acetyl, carboxyl, carboxylester, amide, carbonate, carbamate, alpha-amino acid residues, beta-amino acid residues, alkoxyl, amino, imino, hydroxylamino, mono-alkylamino, di-alkylamino, hydrazinyl, cyano, alkyl-cyano, sulfhydryl, disulfidylalkyl and/or alkyl-sulfidyl;

B1 and/or B2 are independently from each other selected from the group consisting of dicarbonic acid residue linker, succinyl, glutaryl;

C1 and/or C2 are independently from each other selected from the group consisting of LHRH, [D-Lys$^6$]-LHRH, somatostatin, somatostatin analogues, human serum albumin (HSA);

o is 1 or 2;

p is 1 or 2.

In a further preferred embodiment n or o is 1, m or p is 1. In another preferred embodiment, n or o is 2, m or p is 2.

In a yet further preferred embodiment, the compound is selected from the group consisting of:

"Disorazole A1-Succinyl-[D-Lys$^6$]LHRH (Regioisomeric Compounds 11 and 12):

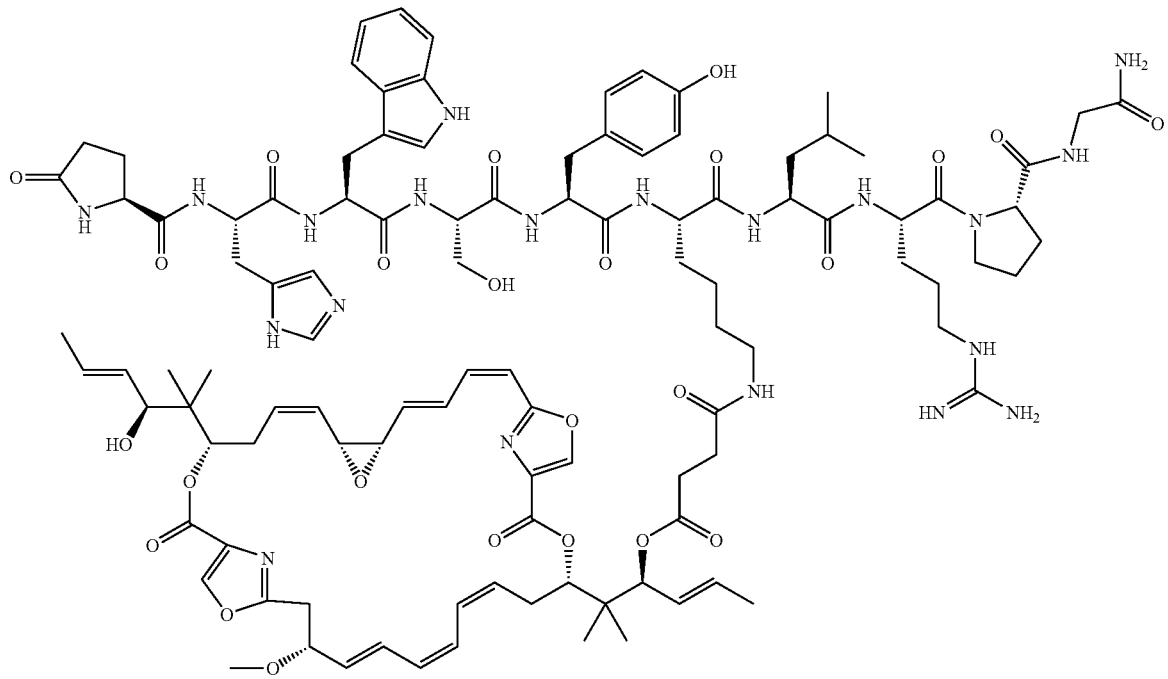

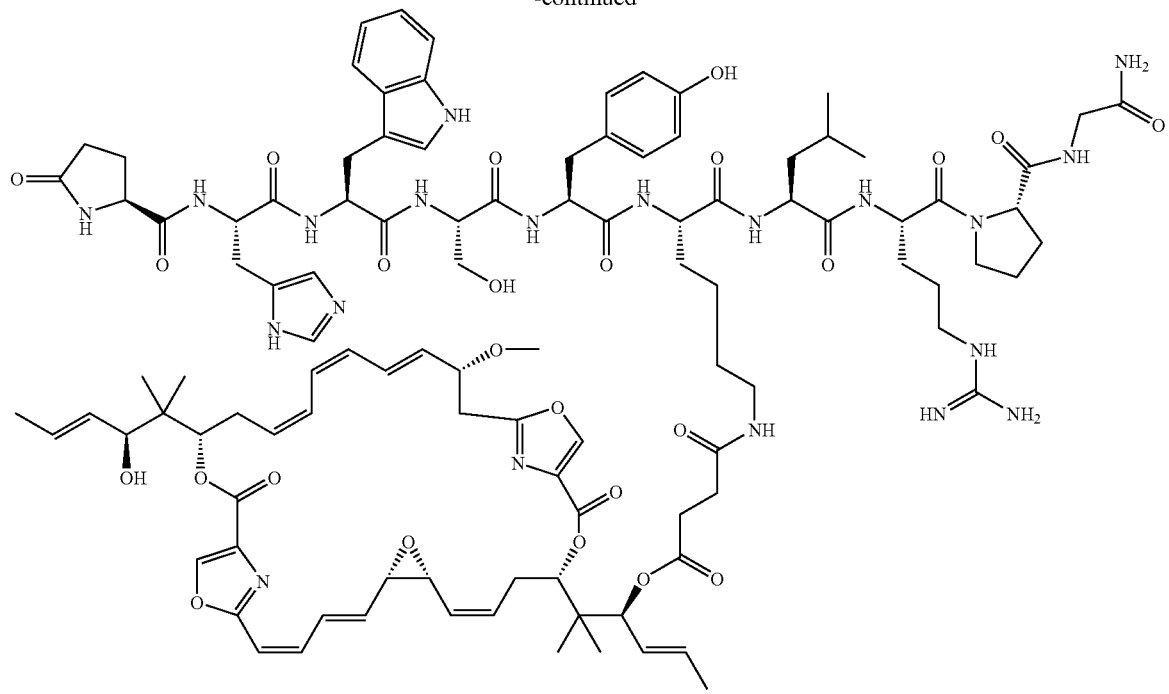
Disorazole E1-Succinyl-[D-Lys$^6$]LHRH (Regioisomeric Compounds 13 and 14):
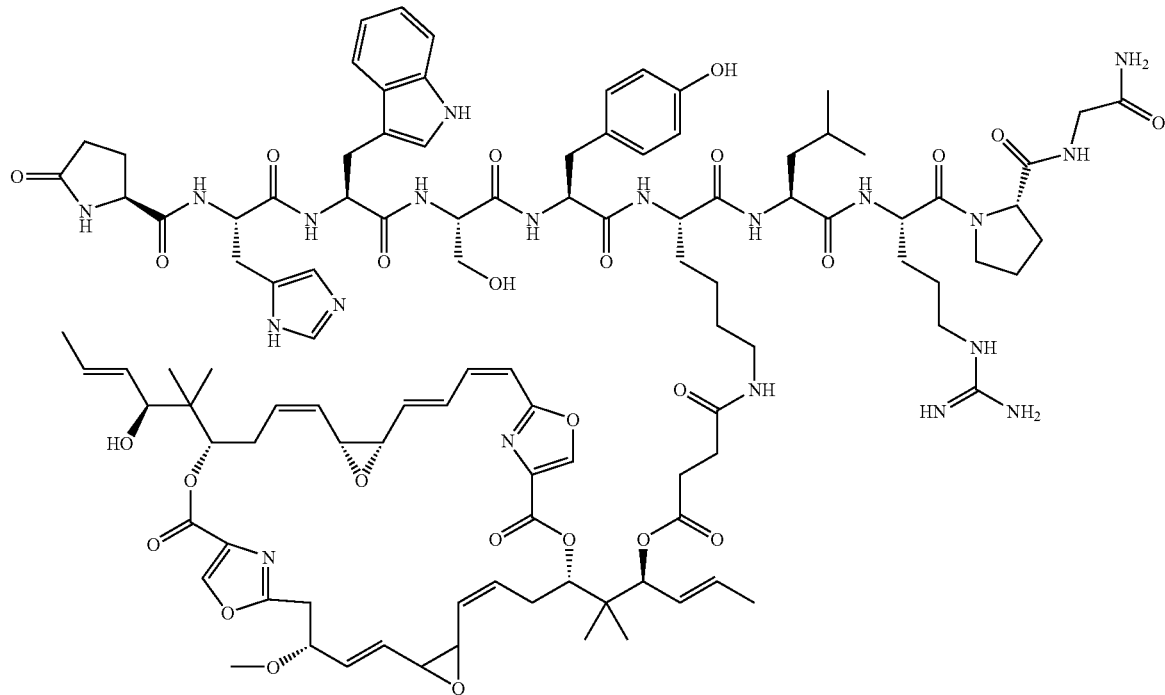

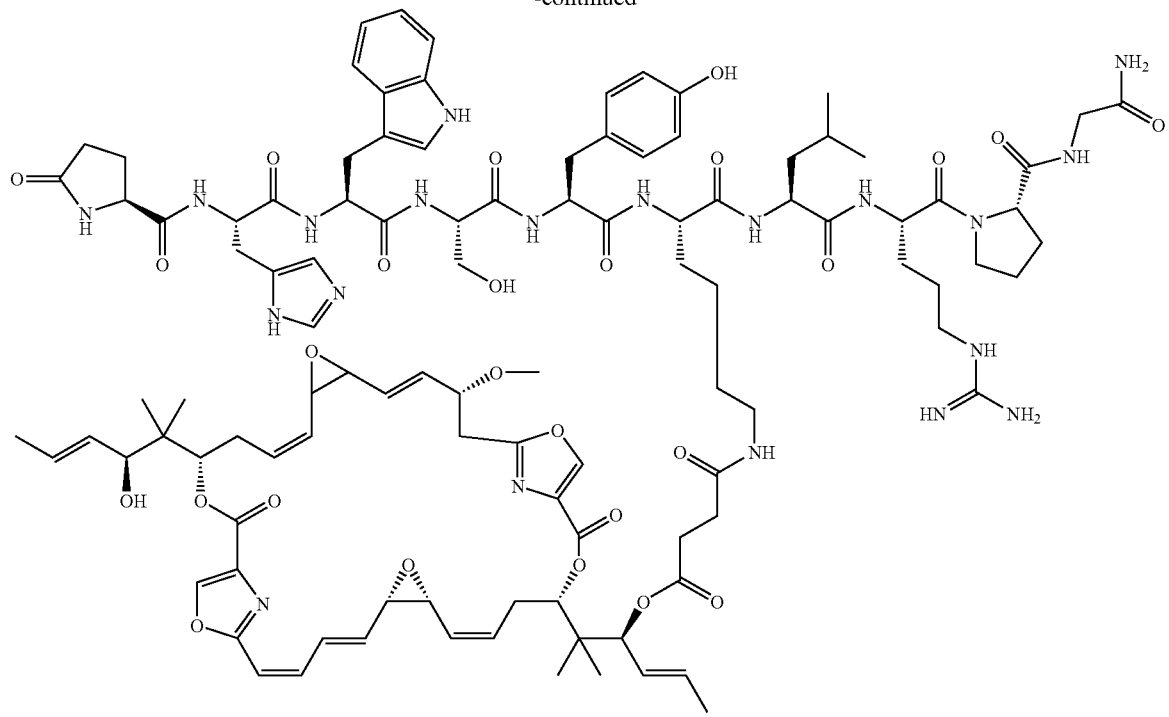
Disorazole A1-(Succinyl-[D-Lys⁶]LHRH)₂ (Compound 15):
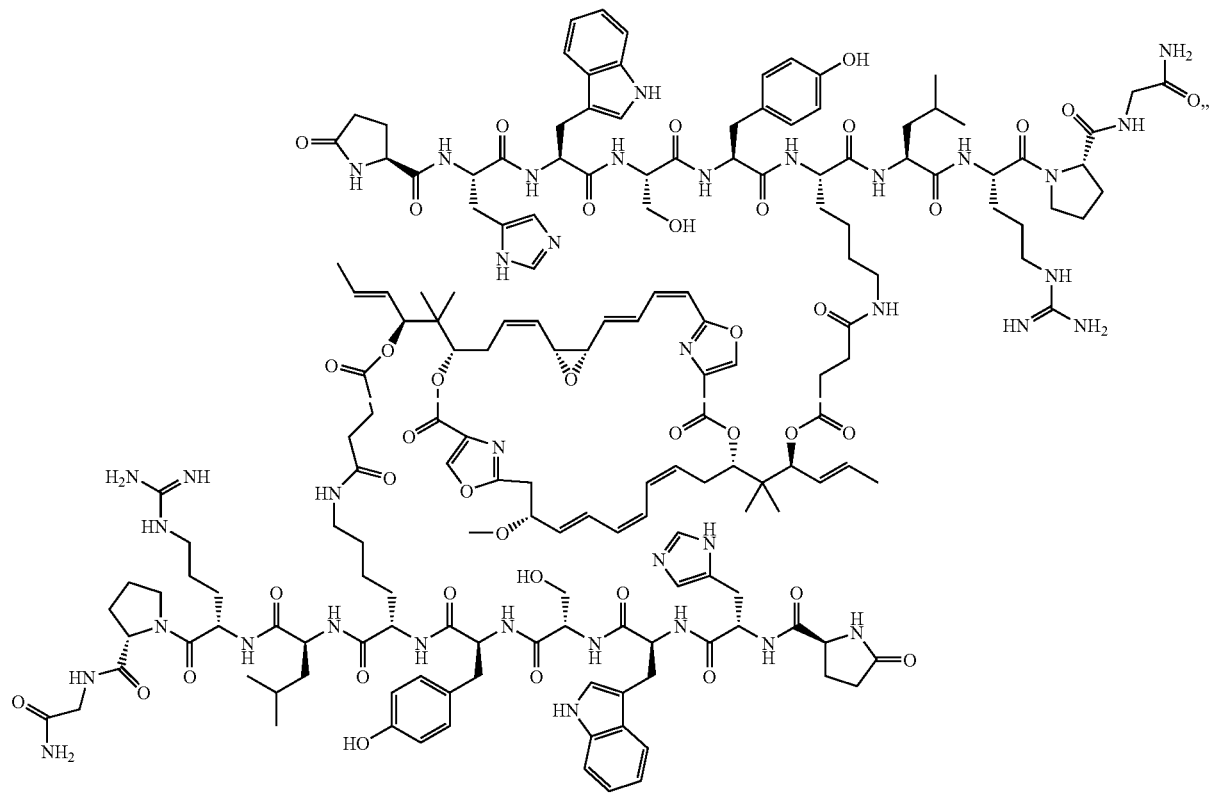

Disorazole Z-Succinyl-[D-Lys⁶]LHRH (Compound 16):
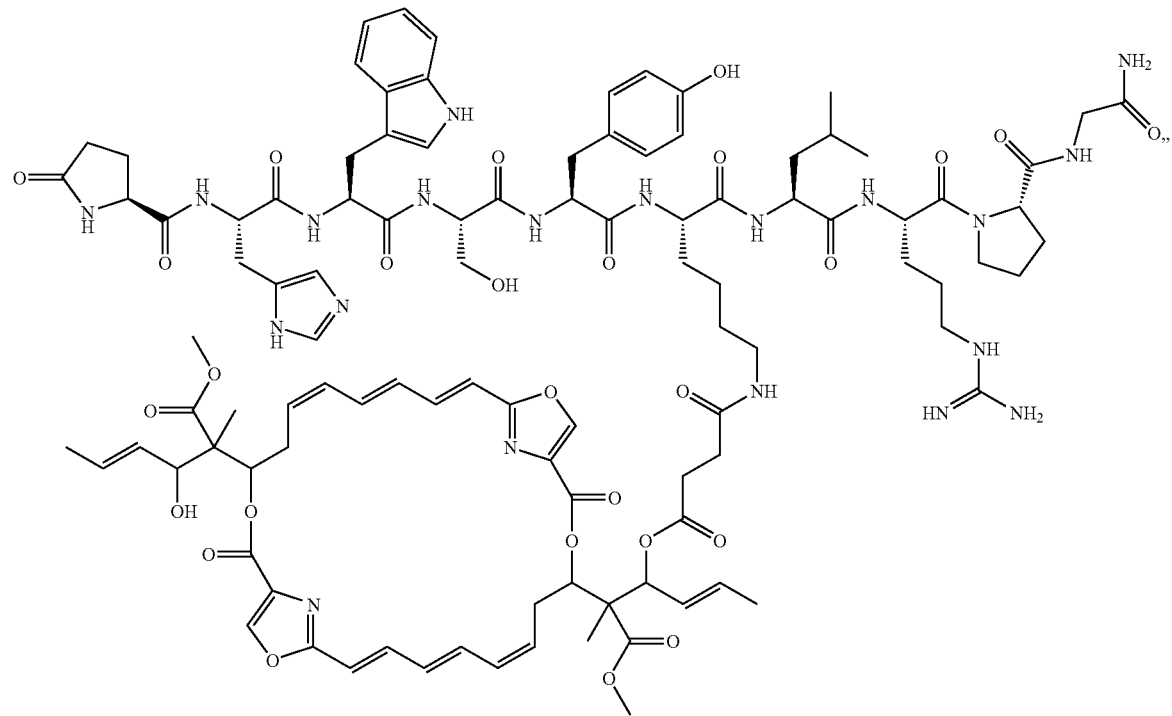
Disorazole Z-(Glutaryl-[D-Lys⁶]LHRH)₂ (Compound 17):
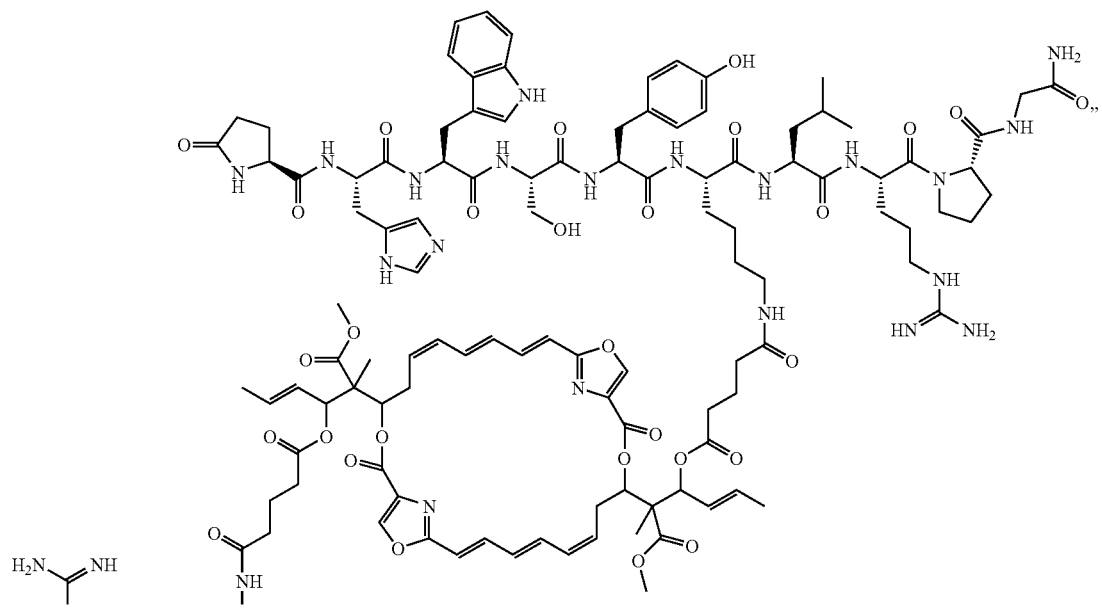

-continued
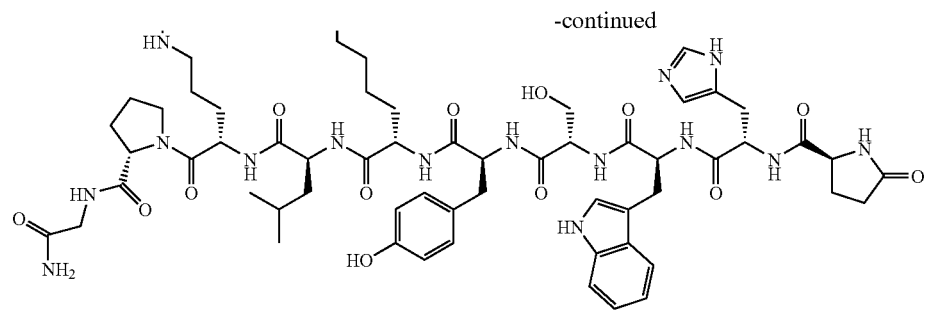
Disorazole Z-Succinyl-Somatostatin (Compound 18):
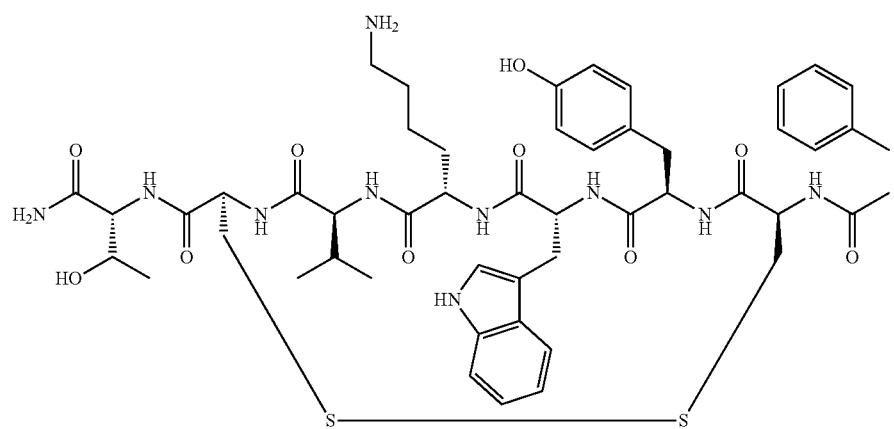
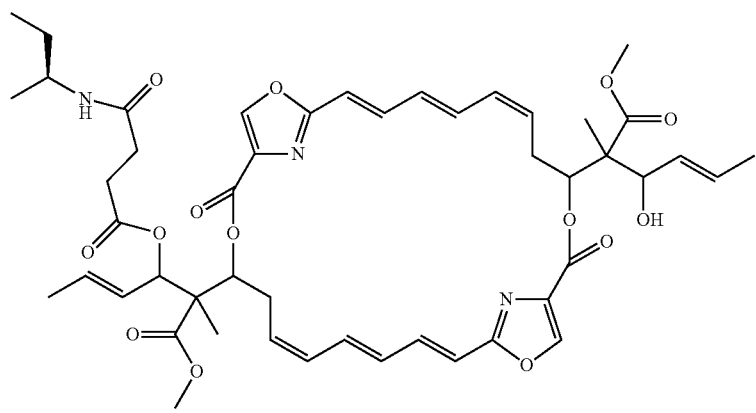

In another aspect, the object of the present invention has been surprisingly solved by providing disorazole compounds according to formula (V)

(V)

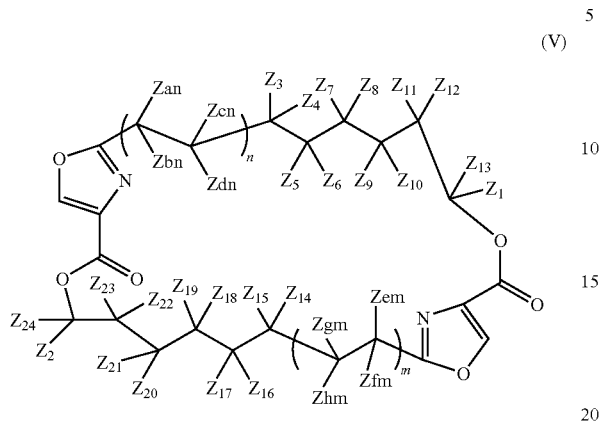

wherein:
$Za_n$, $Zb_n$, $Zc_n$, $Zd_n$, $Ze_m$, $Zf_m$, $Zg_m$, $Zh_m$, Z1, Z2, Z3, Z4, Z5, Z6, Z7, Z8, Z9, Z10, Z11, Z12, Z13, Z14, Z15, Z16, Z17, Z18, Z19, Z20, Z21, Z22, Z23, Z24 are independently from each other selected from the group consisting of hydrogen, alkyl, cycloalkyl, cycloalkyl-alkyl, aryl, heteroaryl, aryl-alkyl, heteroaryl-alkyl, heterocyclyl, heterocyclyl-alkyl, alkylsulfonyl, arylsulfonyl, aryl-alkylsulfonyl, halogen, hydroxyl, carbonyl, acetyl, carboxyl, carboxylester, amide, carbonate, carbamate, alpha-amino acid residues, beta-amino acid residues, alkoxyl, amino, imino, hydroxyl-amino, mono-alkylamino, di-alkylamino, hydrazinyl, cyano, alkyl-cyano, sulfhydryl, disulfidylalkyl and/or alkyl-sulfidyl which are optionally substituted in the alkyl, cycloalkyl, cycloalkyl-alkyl, aryl, heteroaryl, aryl-alkyl, heteroaryl-alkyl, heterocyclyl, heterocyclyl-alkyl, alkylsulfonyl, arylsulfonyl, aryl-alkylsulfonyl, carbonyl, acetyl, carboxyl, carboxylester, amide, carbonate, carbamate, alkoxyl, mono-alkylamino, di-alkylamino, alkyl-cyano, disulfidylalkyl and/or alkyl-sulfidyl group by 1, 2 or 3 substituents independently from each other selected from the group consisting of alkyl, cycloalkyl, cycloalkyl-alkyl, aryl, heteroaryl, aryl-alkyl, heteroaryl-alkyl, heterocyclyl, heterocyclyl-alkyl, alkylsulfonyl, arylsulfonyl, aryl-alkylsulfonyl, halogen, —F, —Cl, —Br, —I, —N$_3$, —NO$_2$, =O, =S, =S(O)$_2$, hydroxyl, carbonyl, acetyl, carboxyl, carboxylester, —C(O)OH, —C(O)NH$_2$, amide, carbonate, carbamate, alpha-amino acid residues, beta-amino acid residues, alkoxyl, amino, imino, hydroxylamino, mono-alkylamino, di-alkylamino, hydrazinyl, cyano, alkyl-cyano, sulfhydryl, disulfidylalkyl and/or alkyl-sulfidyl;
with the proviso that at least one of radicals $Za_n$, $Zb_n$, $Zc_n$, $Zd_n$, $Ze_m$, $Zf_m$, $Zg_m$, $Zh_m$, Z1, Z2, Z3, Z4, Z5, Z6, Z7, Z8, Z9, Z10, Z11, Z12, Z13, Z14, Z15, Z16, Z17, Z18, Z19, Z20, Z21, Z22, Z23, Z24 is independently selected from the group consisting of carboxylester, amide, carbonate, carbamate, alpha-amino acid residues, beta-amino acid residues;
with the further proviso that acetyl is excluded from carboxylester;
optionally, any two adjacent radicals Z of radicals $Za_n$, $Zb_n$, $Zc_n$, $Zd_n$, $Ze_m$, $Zf_m$, $Zg_m$, $Zh_m$, Z1, Z2, Z3, Z4, Z5, Z6, Z7, Z8, Z9, Z10, Z11, Z12, Z13, Z14, Z15, Z16, Z17, Z18, Z19, Z20, Z21, Z22, Z23, Z24 can form an atomic bond to yield a double bond or can form an epoxide (oxiran), aziran (aziridine), alkyl-, cycloalkyl-, cycloalkyl-alkyl-, heteroaryl-, aryl-alkyl-, heteroaryl-alkyl-, heterocyclyl- and/or heterocyclyl-alkyl-substituted aziran (aziridine), thiirane and/or thiirane-S-oxide group;
n is 0, 1, 2, 3;
m is 0, 1, 2, 3.
In a preferred embodiment of the present invention, disorazole compounds according to below formula (VI) are provided, (VI)

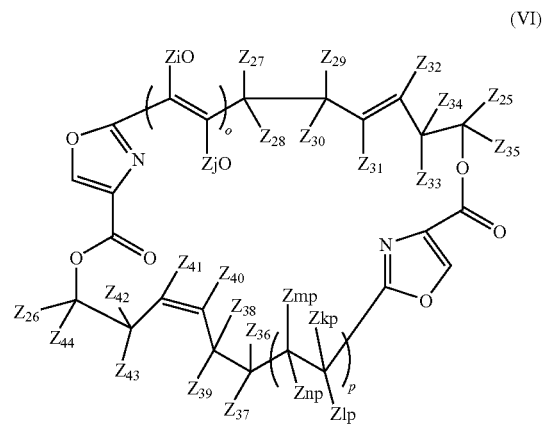

wherein:
$Zi_o$, $Zj_o$, $Zk_p$, $Zl_p$, $Zm_p$, $Zn_p$, Z25, Z26, Z27, Z28, Z29, Z30, Z31, Z32, Z33, Z34, Z35, Z36, Z37, Z38, Z39, Z40, Z41, Z42, Z43, Z44 are independently from each other selected from the group consisting of hydrogen, alkyl, cycloalkyl, cycloalkyl-alkyl, aryl, heteroaryl, aryl-alkyl, heteroaryl-alkyl, heterocyclyl, heterocyclyl-alkyl, alkylsulfonyl, arylsulfonyl, aryl-alkylsulfonyl, halogen, hydroxyl, carbonyl, acetyl, carboxyl, carboxylester, amide, carbonate, carbamate, alpha-amino acid residues, beta-amino acid residues, alkoxyl, amino, imino, hydroxylamino, mono-alkylamino, di-alkylamino, hydrazinyl, cyano, alkyl-cyano, sulfhydryl, disulfidylalkyl and/or alkyl-sulfidyl which are optionally substituted in the alkyl, cycloalkyl, cycloalkyl-alkyl, aryl, heteroaryl, aryl-alkyl, heteroaryl-alkyl, heterocyclyl, heterocyclyl-alkyl, alkylsulfonyl, arylsulfonyl, aryl-alkylsulfonyl, carbonyl, acetyl, carboxyl, carboxylester, amide, carbonate, carbamate, alkoxyl, mono-alkylamino, di-alkylamino, alkyl-cyano, disulfidylalkyl and/or alkyl-sulfidyl group by 1, 2 or 3 substituents independently from each other selected from the group consisting of alkyl, cycloalkyl, cycloalkyl-alkyl, aryl, heteroaryl, aryl-alkyl, heteroaryl-alkyl, heterocyclyl, heterocyclyl-alkyl, alkylsulfonyl, arylsulfonyl, aryl-alkylsulfonyl, halogen, —F, —Cl, —Br, —I, —N$_3$, —NO$_2$, =O, =S, =S(O)$_2$, hydroxyl, carbonyl, acetyl, carboxyl, carboxylester, —C(O)OH, —C(O)NH$_2$, amide, carbonate, carbamate, alpha-amino acid residues, beta-amino acid residues, alkoxyl, amino, imino, hydroxylamino, mono-alkylamino, di-alkylamino, hydrazinyl, cyano, alkyl-cyano, sulfhydryl, disulfidylalkyl and/or alkyl-sulfidyl;
with the proviso that at least one of radicals $Zi_o$, $Zj_o$, $Zk_p$, $Zl_p$, $Zm_p$, $Zn_p$, Z25, Z26, Z27, Z28, Z29, Z30, Z31, Z32, Z33, Z34, Z35, Z36, Z37, Z38, Z39, Z40, Z41, Z42, Z43, Z44 is independently selected from the group consisting of carboxylester, amide, carbonate, carbamate, alpha-amino acid residues, beta-amino acid residues;
with the further proviso that acetyl is excluded from carboxylester;
optionally, any two adjacent radicals Z of radicals $Zi_o$, $Zj_o$, $Zk_p$, $Zl_p$, $Zm_p$, $Zn_p$, Z25, Z26, Z27, Z28, Z29, Z30, Z31, Z32, Z33, Z34, Z35, Z36, Z37, Z38, Z39, Z40, Z41, Z42, Z43, Z44 can form an atomic bond to yield a double bond or can form an epoxide (oxiran), aziran (aziridine), alkyl-, cycloalkyl-, cycloalkyl-alkyl-, heteroaryl-, aryl-alkyl-, heteroaryl-alkyl-, heterocyclyl- and/or heterocyclyl-alkyl-substituted aziran (aziridine), thiirane and/or thiirane-S-oxide group;

o is 0, 1, 2, 3;
p is 0, 1, 2, 3.

In a further preferred embodiment, disorazole compounds according to formulae (V) and (VI) are provided, wherein n or o is 1 and m or p is 1. In another preferred embodiment, disorazole compounds according to formulae (V) and (VI) are provided, wherein n or o is 2, m or p is 2.

In a yet further preferred embodiment, the disorazole derivative is selected from the group consisting of:

Regioisomeric Compounds 1 and 2:

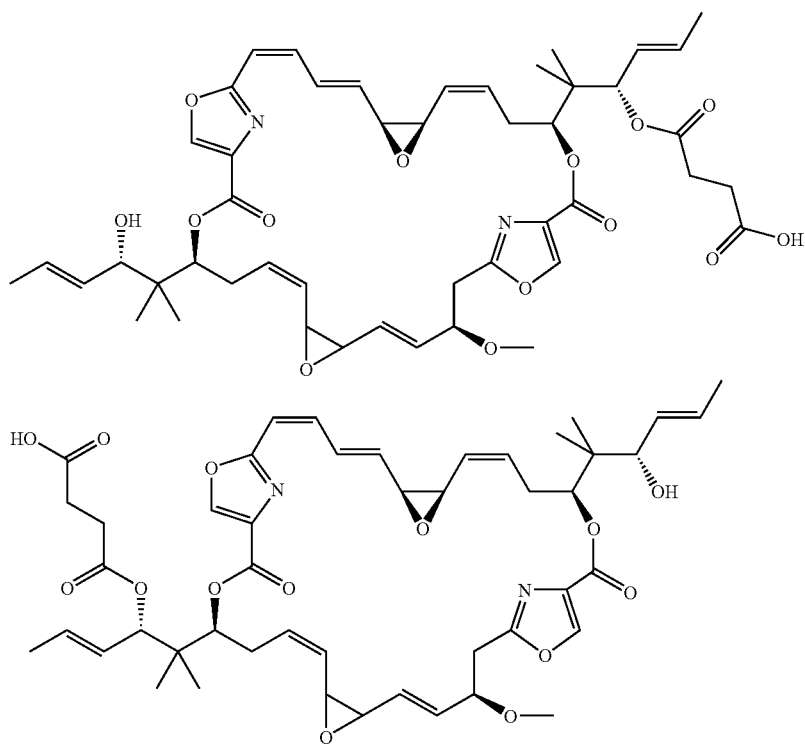

Compound 3:

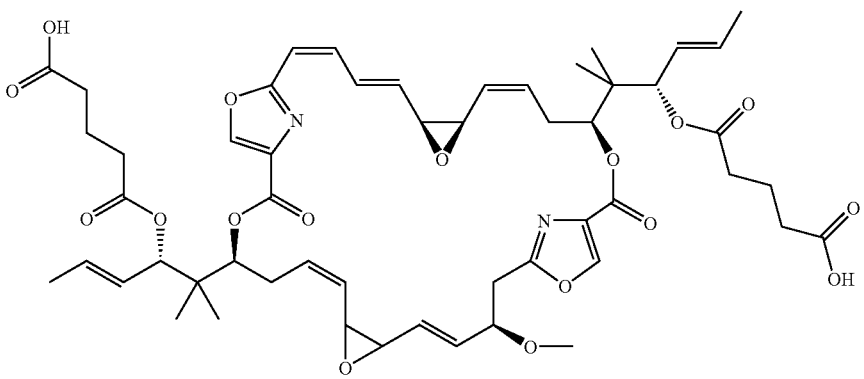 [SMILES: C/C=C/[C@H](OC(=O)CCCC(=O)O)C(C)(C)[C@@H]1C/C=C\C2OC2/C=C/[C@H](OC)Cc2nc(co2)C(=O)O[C@H](C(C)(C)[C@H](/C=C/C)OC(=O)CCCC(=O)O)C/C=C\[C@H]2O[C@H]2/C=C/C=C\c2nc(co2)C(=O)O1]

Compound 4:
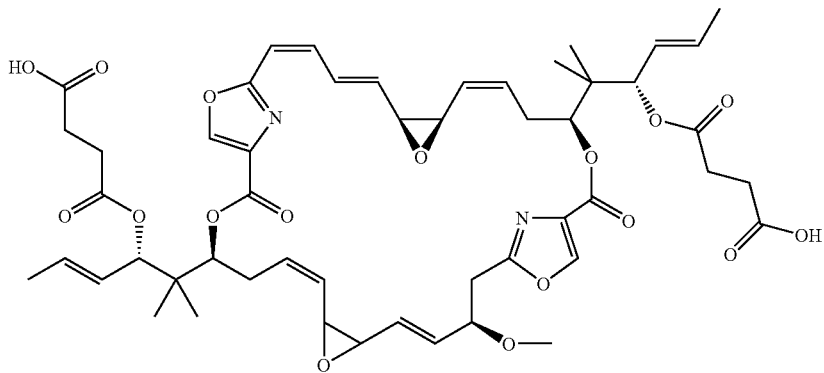 [SMILES: C/C=C/[C@H](OC(=O)CCC(=O)O)C(C)(C)[C@@H]1C/C=C\C2OC2/C=C/[C@H](OC)Cc2nc(co2)C(=O)O[C@H](C(C)(C)[C@H](/C=C/C)OC(=O)CCC(=O)O)C/C=C\[C@H]2O[C@H]2/C=C/C=C\c2nc(co2)C(=O)O1]
Regioisomeric Compound 5 and 6:
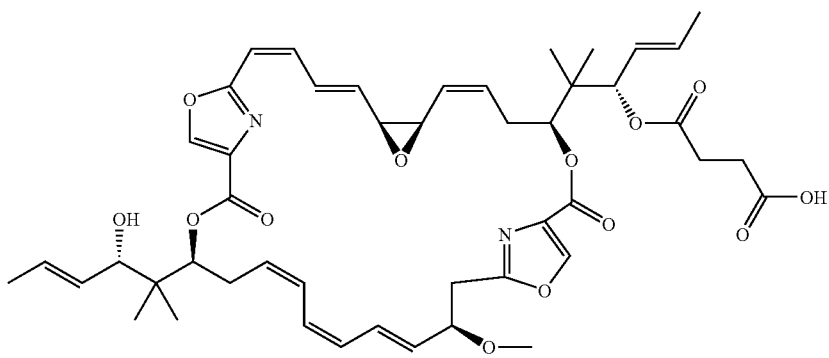
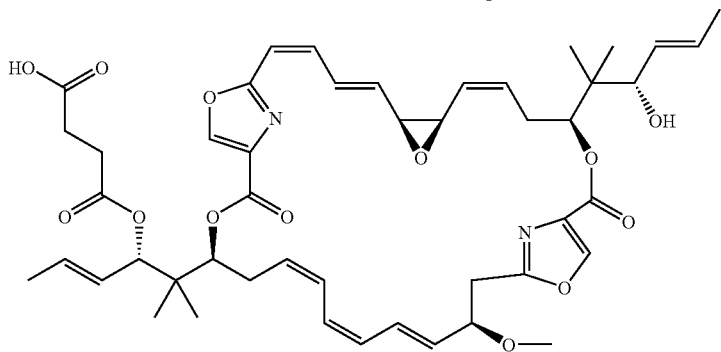
Compound 7:
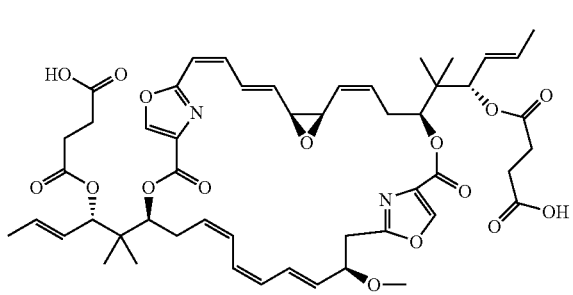 [SMILES: C/C=C/[C@H](OC(=O)CCC(=O)O)C(C)(C)[C@@H]1C\C=C/C=C\C=C\[C@H](OC)Cc2nc(co2)C(=O)O[C@H](C(C)(C)[C@H](/C=C/C)OC(=O)CCC(=O)O)C/C=C\[C@H]2O[C@H]2/C=C/C=C\c2nc(co2)C(=O)O1]
Compound 9:
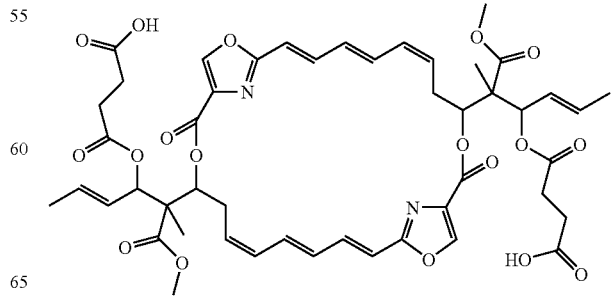

Compound 10:

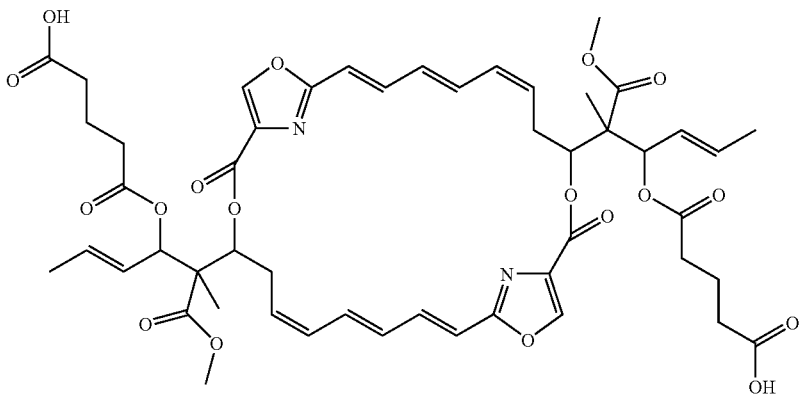 [SMILES: C/C=C/C(OC(=O)CCCC(=O)O)C(C)(C(=O)OC)C1C\C=C/C=C/C=C/c2nc(co2)C(=O)OC(C(C)(C(=O)OC)C(/C=C/C)OC(=O)CCCC(=O)O)C\C=C/C=C/C=C/c2nc(co2)C(=O)O1]

Compound 19:

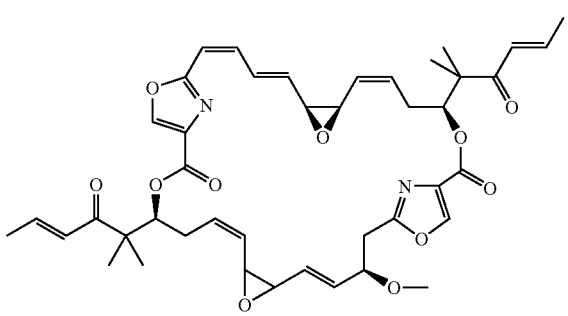 [SMILES: C/C=C/C(=O)C(C)(C)[C@@H]1C/C=C\C2OC2/C=C/[C@H](OC)Cc2nc(co2)C(=O)O[C@H](C(C)(C)C(=O)/C=C/C)C/C=C\[C@H]2O[C@H]2/C=C/C=C\c2nc(co2)C(=O)O1]

Compound 20:

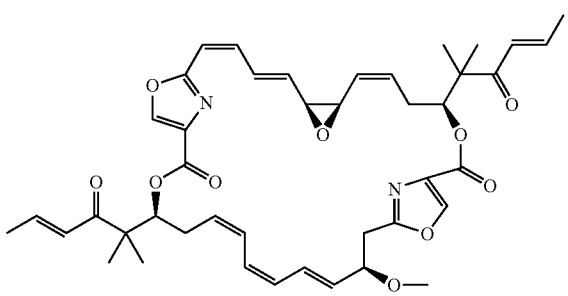 [SMILES: C/C=C/C(=O)C(C)(C)[C@@H]1C\C=C/C=C\C=C\[C@H](OC)Cc2nc(co2)C(=O)O[C@H](C(C)(C)C(=O)/C=C/C)C/C=C\[C@H]2O[C@H]2/C=C/C=C\c2nc(co2)C(=O)O1]

Compound 21:

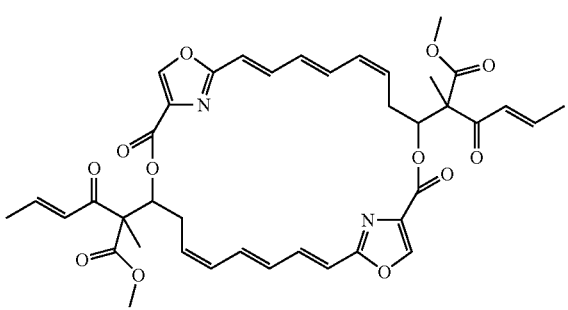 [SMILES: C/C=C/C(=O)C(C)(C(=O)OC)C1C\C=C/C=C/C=C/c2nc(co2)C(=O)OC(C(C)(C(=O)/C=C/C)C(=O)OC)C\C=C/C=C/C=C/c2nc(co2)C(=O)O1]

All compounds, i.e. disorazole conjugates and disorazole derivatives, illustrated herein, generically [by above formulae (I) to (VI) and different R radicals] and explicitly, are in the following referred to as the compounds of the (present) invention.

The terms indicated for explanation of the above compounds of the invention always, unless indicated otherwise in the description or in the claims, have the following meanings:

The term substituted means that the corresponding radical or group has one or more substituents. Where a radical has a plurality of substituents, and a selection of various substituents is specified, the substituents are selected independently of one another and need not be identical. The term unsubstituted means that the corresponding group has no substituent.

The term optionally substituted means that the corresponding group is either unsubstituted or substituted by one or more substituents. The term substituted by up to 3 substituents means that the corresponding radical or group is substituted either by one or by two or three substituents.

The term alkyl includes for the purposes of this invention acyclic saturated, partially unsaturated or unsaturated hydrocarbons having C1-C12 carbon atoms, which may be straight-chain or branched and may contain one or more double bonds and/or one or more triple bonds. The term alkyl preferably stands for alkyl chains of 1 to 8, particularly preferably 1 to 6, carbon atoms. Examples of suitable alkyl radicals are methyl, ethyl, n-propyl, isopropyl, n-butyl, isobutyl. sec-butyl, tert-butyl, n-pentyl, isopentyl, neo-pentyl, tert-pentyl, 2- or 3-methyl-pentyl, n-hexyl, 2-hexyl, isohexyl, n-heptyl, n-octyl, n-nonyl, n-decyl, n-undecyl, n-dodecyl, n-tetradecyl, n-hexadecyl, n-octadecyl, n-icosanyl, n-docosanyl, ethylenyl (vinyl), propenyl (—CH$_2$CH=CH$_2$; —CH=CH—CH$_3$, —C(=CH$_2$)—CH$_3$), butenyl, pentenyl, hexenyl, heptenyl, octenyl, octadienyl, octadecenyl, octadec-9-enyl, icosenyl, icos-11-enyl, (Z)-icos-11-enyl, docosnyl, docos-13-enyl, (Z)-docos-13-enyl, ethynyl, propynyl (—CH$_2$—C≡CH, —C≡C—CH$_3$), butynyl, pentynyl, hexynyl, heptynyl and octynyl.

The term cycloalkyl stands for a saturated or partially unsaturated non-aromatic cyclic hydrocarbon group/radical, containing 1, 2 or 3 rings, including monocyclic alkyl, bicyclic alkyl and tricyclic alkyl, and containing a total of 3 to 20 carbon atoms forming the rings, preferably 3 to 10, most preferably (C$_3$-C$_8$)-cycloalkyl. Examples of suitable cycloalkyl radicals are cyclopropyl, cyclobutyl, cyclopentyl, cyclohexyl, cycloheptyl, cyclooctyl, cyclodecyl, cyclohexenyl, cyclopentenyl, cyclooctadienyl.

The term cycloalkyl-alkyl refers to a radical in which the cycloalkyl group is linked via an alkyl group, where the alkyl and cycloalkyl groups have the meanings defined herein, preferably a $(C_3-C_8)$-cycloalkyl-$(C_1-C_4)$-alkyl radical. Examples thereof are cyclopropylmethyl, cyclohexylmethyl, cyclopentylethyl, cyclohexenylethyl.

The term aryl refers to aromatic hydrocarbon systems having 3 to 14, preferably 5 to 14, carbon atoms. The term aryl also includes systems in which the aromatic cycle is part of a bi- or polycyclic saturated, partially unsaturated and/or aromatic system, such as were the aromatic cycle is fused to an aryl, cycloalkyl, heteroaryl or heterocyclyl group as defined herein via any desired and possible ring member of the aryl radical. Such aryl radicals can be linked via any ring member. Examples of aryl are inter alia phenyl, biphenyl, naphthyl and anthracenyl, but also indanyl, indenyl, or 1,2,3,4-tetrahydronaphthyl.

The term heteroaryl refers to a 5-, 6- or 7-membered cyclic aromatic radical which comprises at least 1, where appropriate also 2, 3, 4 or 5 heteroatoms, preferably nitrogen, oxygen and/or sulfur, where the heteroatoms are identical or different. The number of nitrogen atoms is preferably 0, 1, 2, or 3, and that of the oxygen and sulfur atoms is independently 0 or 1. The term heteroaryl also includes systems in which the aromatic cycle is part of a bi- or polycyclic saturated, partially unsaturated and/or aromatic system, such as were the aromatic cycle is fused to an aryl, cycloalkyl, heteroaryl or heterocyclyl group as defined herein via any desired and possible ring member of the heteroaryl radical. Such heteroaryl radicals can be linked via any ring member. Examples of heteroaryl include pyrrolyl, thienyl, furyl, imidazolyl, thiazolyl, isothiazolyl, oxazolyl, oxadiazolyl, isoxazolyl, pyrazolyl, pyridinyl, pyrimidinyl, pyrazinyl, indolyl, quinolinyl, isoquinolinyl, imidazolyl, triazolyl, tetrazolyl, pyridazinyl, phthalazinyl, indazolyl, indolizinyl, quinoxalinyl, quinazolinyl, pteridinyl, carbazolyl, phenazinyl, phenoxazinyl, phenothiazinyl, acridinyl.

The terms aryl-alkyl and heteroaryl-alkyl refer to radicals in which the aryl or heteroaryl radical is linked via an alkyl group, where the alkyl, aryl and heteroaryl groups have the meanings defined herein. Preferred aryl-alkyl groups are phenyl-$(C_1-C_4)$-alkyl radicals, preferably benzyl or phenylethyl radicals. Preferred heteroaryl-alkyl groups are indolyl-$(C_1-C_4)$-alkyl radicals, preferably 1H-indole-3-yl-methyl or 2-(1H-indole-3-yl)-ethyl.

The term heterocyclyl refers to a mono- or polycyclic system of 3 to 20, preferably 5 or 6 to 14 ring atoms comprising carbon atoms and 1, 2, 3, 4, or 5 heteroatoms, in particular nitrogen, oxygen and/or sulfur, which are identical or different. The cyclic system may be saturated, mono- or polyunsaturated but may not be aromatic. In the case of a cyclic system consisting of at least two rings the rings may be fused or spiro- or otherwise connected. Such heterocyclyl radicals can be linked via any ring member. The term heterocyclyl also includes systems in which the heterocycle is part of a bi- or polycyclic saturated, partially unsaturated and/or aromatic system, such as where the heterocycle is fused to an aryl, cycloalkyl, heteroaryl or heterocyclyl group as defined herein via any desired and possible ring member of the heterocycyl radical. Examples of heterocyclyl include pyrrolidinyl, thiapyrrolidinyl, piperidinyl, piperazinyl, oxapiperazinyl, oxapiperidinyl, oxadiazolyl, tetrahydrofuryl, imidazolidinyl, thiazolidinyl, tetrahydropyranyl, morpholinyl, tetrahydrothiophenyl, dihydropyranyl.

The term heterocyclylalkyl refers to radicals in which the heterocyclyl group is linked via an alkyl group, where the alkyl and heterocyclyl groups have the meanings defined herein. Preferred are heterocyclyl-$(C_1-C_4)$-alkyl radicals.

The terms alkylsulfonyl, arylsulfonyl and aryl-alkylsulfonyl refer to radicals in which the alkyl, aryl or aryl-alkyl group is linked via a —$SO_2$— group, where the alkyl, aryl and aryl-alkyl groups have the meanings defined herein. Examples are methylsulfonyl and phenylsulfonyl.

The term halogen, halogen atom or halogen substituent (Hal-) refers to one, where appropriate, a plurality of fluorine (F, fluoro), bromine (Br, bromo), chlorine (Cl, chloro), or iodine (I, iodo) atoms. The designations dihalogen, trihalogen and perhalogen refer respectively to two, three and four substituents, where each substituent can be selected independently from the group consisting of fluorine, chlorine, bromine and iodine. Halogen preferably means a fluorine, chlorine or bromine atom.

The term carbonyl refers to radicals in which an alkyl, cycloalkyl, cyloalkyl-alkyl, aryl, heteroaryl, aryl-alkyl, heteroaryl-alkyl, heterocyclyl and/or heterocyclyl-alkyl group is linked via a —C(O)— group, where the alkyl, cycloalkyl, cyloalkyl-alkyl, aryl, heteroaryl, aryl-alkyl, heteroaryl-alkyl, heterocyclyl and/or heterocyclyl-alkyl groups have the meanings defined herein. Examples are —C(O)—$CH_3$, —C(O)—$CH_2CH_3$, —C(O)-isopropyl and —C(O)-tBu (tBu=tert. Butyl).

The term carboxyl refers to radicals in which an alkyl, cycloalkyl, cyloalkyl-alkyl, aryl, heteroaryl, aryl-alkyl, heteroaryl-alkyl, heterocyclyl and/or heterocyclyl-alkyl group is linked via a —C(O)O— group, where the alkyl, cycloalkyl, cyloalkyl-alkyl, aryl, heteroaryl, aryl-alkyl, heteroaryl-alkyl, heterocyclyl and/or heterocyclyl-alkyl groups have the meanings defined herein. Examples are —C(O)O—$CH_3$ and —C(O)O-phenyl.

The term carboxylester refers to radicals in which an alkyl, cycloalkyl, cyloalkyl-alkyl, aryl, heteroaryl, aryl-alkyl, heteroaryl-alkyl, heterocyclyl and/or heterocyclyl-alkyl group is linked via a —OC(O)— group, where the alkyl, cycloalkyl, cyloalkyl-alkyl, aryl, heteroaryl, aryl-alkyl, heteroaryl-alkyl, heterocyclyl and/or heterocyclyl-alkyl groups have the meanings defined herein. Examples are acetyl, —OC(O)-phenyl and the like.

The term carbonate refers to radicals in which an alkyl, cycloalkyl, cyloalkyl-alkyl, aryl, heteroaryl, aryl-alkyl, heteroaryl-alkyl, heterocyclyl and/or heterocyclyl-alkyl group is linked via a —OC(O)O— group, where the alkyl, cycloalkyl, cyloalkyl-alkyl, aryl, heteroaryl, aryl-alkyl, heteroaryl-alkyl, heterocyclyl and/or heterocyclyl-alkyl groups have the meanings defined herein. Examples are —OC(O)O—$CH_3$ and —OC(O)O-phenyl.

The term carbamate refers to radicals in which an alkyl, cycloalkyl, cyloalkyl-alkyl, aryl, heteroaryl, aryl-alkyl, heteroaryl-alkyl, heterocyclyl and/or heterocyclyl-alkyl group is linked via a —OC(O)NH— group, a —NHC(O)O— group, a —OC(O)NR— group or a —NRC(O)O— group, wherein R is independently selected from the group consisting of "alkyl, cycloalkyl, cycloalkyl-alkyl, aryl, heteroaryl, aryl-alkyl, heteroaryl-alkyl, heterocyclyl, heterocyclyl-alkyl, halogen, —F, —Cl, —Br, —I, —$N_3$, —$NO_2$, hydroxyl, alkoxyl, amino, imino, hydroxylamino, hydrazinyl, cyano, alkyl-cyano, sulfhydryl, where the alkyl, cycloalkyl, cycloalkyl-alkyl, aryl, heteroaryl, aryl-alkyl, heteroaryl-alkyl, heterocyclyl, heterocyclyl-alkyl, alkoxyl, hydrazinyl and/or alkyl-cyano groups have the meanings defined herein.

The term alpha-amino acid residue for the purpose of the present invention refers to all known 20 proteinogenic alpha-amino acids as well as to naturally occurring (i.e. in any biological systems) alpha-amino acids, such as for instance selenocystein, pyrrolysine, citrulline, ornithine, homocysteine, N-methylariginine, N-acetyllysine, gamma-carboxyglutamate, 5-hydroxylysine, 3-methylhistidine and/or N,N,N-trimethyllysine. In this connection residue refers to the entire amino acid moiety including alpha-carbon atom attached side chain and backbone. The term alpha-amino acid residue for the purpose of the present invention also refers to all known alpha-amino acids that are not proteinogenic nor are known to occur naturally (i.e. in any biological systems). Examples are norleucine, cyclohexylglycine, 2-naphthylalanine, substituted alpha-amino acids (e.g. halogen substituted Tyr or Phe) as well as protected alpha-amino acid side chains, where a protection group such as Fmoc, Boc, Cbz, Aloc, trityl, acetyl and/or benzyl is directly attached/reacted to a functionalization (e.g. amino, hydroxy and/or carboxy residue). In this connection residue refers to the entire amino acid moiety including alpha-carbon atom attached side chain and backbone.

Accordingly, the term beta-amino acid residue for the purpose of the present invention refers to all known beta-amino acids that are not proteinogenic nor are known to occur naturally (i.e. in any biological systems). In this connection residue refers to the entire amino acid moiety including beta-carbon atom attached side chain and backbone.

The term "alkoxyl refers to radicals in which an "alkyl, "cycloalkyl, "cycloalkyl-alkyl, "aryl, "aryl-alkyl, "heteroaryl, "heteroaryl-alkyl, "heterocyclyl and/or "heterocyclyl-alkyl group is linked via an oxygen atom (—O-group), where "alkyl, "cycloalkyl, "cycloalkyl-alkyl, "aryl, "arylalkyl, "heteroaryl, "heteroaryl-alkyl, "heterocyclyl and "heterocyclyl-alkyl have the meanings as defined herein.

The terms "mono-alkylamino and "di-alkylamino refer to radicals in which one or two alkyl groups, respectively, are linked via a nitrogen atom, where the alkyl group has the meaning defined herein. Examples are ethylamino, dimethylamino and isopropylethylamino.

The term hydrazinyl refers to a C=N—NH—, NH—N=C—, C=N—NR— and/or NR—N=C— group, wherein R is independently selected from the group consisting of "alkyl, cycloalkyl, cycloalkyl-alkyl, aryl, heteroaryl, aryl-alkyl, heteroaryl-alkyl, heterocyclyl, heterocyclyl-alkyl, halogen, —F, —Cl, —Br, —I, —N$_3$, —NO$_2$, hydroxyl, alkoxyl, amino, imino, hydroxylamino, hydrazinyl, cyano, alkyl-cyano, sulfhydryl, where the alkyl, cycloalkyl, cycloalkyl-alkyl, aryl, heteroaryl, aryl-alkyl, heteroarylalkyl, heterocyclyl, heterocyclyl-alkyl, alkoxyl, hydrazinyl and/or alkyl-cyano groups have the meanings defined herein.

The term "alkyl-cyano refers to radicals in which an alkyl group is linked via a cyano group, where the alkyl group has the meaning defined herein. Examples are methylcyano and n-propylcyano.

The term "disulfidalkyl refers to radicals in which an alkyl group is linked via a —S—S— group, where the alkyl group has the meaning defined herein.

The term "alkyl-sulfidyl refers to radicals in which an alkyl group is linked via a sulfur atom, where the alkyl group has the meaning defined herein.

All stereoisomers of the compounds of the invention are contemplated, either in a mixture or in pure or substantially pure form. The compounds of the present invention can have asymmetric centers at any of the carbon atoms including any one of the substituent radicals. Consequently, compounds of the invention can exist in the form of their racemates, in the form of the pure enantiomers and/or diastereomers or in the form of mixtures of these enantiomers and/or diastereomers. The mixtures may have any desired mixing ratio of the stereoisomers. All these different stereochemical forms and mixtures are within the scope of the present invention.

Thus, for example, the compounds of the invention which have one or more centers of chirality and which occur as racemates or as diastereomer mixtures can be fractionated by methods known per se into their optical pure isomers, i.e. enantiomers or diastereomers. The separation of the compounds of the invention can take place by column separation on chiral or nonchiral phases or by recrystallization from an optionally optically active solvent or with use of an optically active acid or base or by derivatization with an optically active reagent such as, for example, an optically active alcohol, and subsequent elimination of the radical.

For the avoidance of doubt, compounds of the invention can be present in the form of all possible double bond isomers, such as "pure E- or Z-isomers or mixtures of these double bond isomers.

Where possible, the compounds of the invention may be in the form of the tautomers.

It is likewise possible for the compounds of the invention to be in the form of any desired prodrugs such as, for example, esters, carbonates, carbamates, ureas, amides or phosphates, in which cases the actually biologically active form is released only through metabolism. Any compound that can be converted in vivo to provide the bioactive agent (i.e. a compound of the invention) is a prodrug within the scope and spirit of the invention.

Various forms of prodrugs are well known in the art and are described for instance in:
  (i) The Practice of Medicinal Chemistry (Wermuth C G et al., Chapter 31, Academic Press 1996);
  (ii) Design of Prodrugs (editor: Bundgaard H, Elsevier 1985); and
  (iii) A Textbook of Drug Design and Development (Krogsgaard-Larson P and Bundgaard H, eds., Chapter 5: 113-191, Harwood Academic Publishers 1991).

Said references are incorporated herein by reference.

It is further known that chemical substances are converted in the body into metabolites which may where appropriate likewise elicit the desired biological effect—in some circumstances even in more pronounced form.

Any biologically active compound that was converted in vivo by metabolism from any compound of the invention is a metabolite within the scope and spirit of the invention.

The compounds of the invention can, if they have a sufficiently basic group such as, for example, a primary, secondary or tertiary amine, be converted with inorganic and organic acids into salts. The pharmaceutically acceptable salts of the compounds of the invention are preferably formed with hydrochloric acid, hydrobromic acid, iodic acid, sulfuric acid, phosphoric acid, methanesulfonic acid, p-toluenesulfonic acid, carbonic acid, formic acid, acetic acid, sulfoacetic acid, trifluoroacetic acid, oxalic acid, malonic acid, maleic acid, succinic acid, tartaric acid, racemic acid, malic acid, embonic acid, mandelic acid, fumaric acid, lactic acid, citric acid, taurocholic acid, glutaric acid, stearic acid, glutamic acid or aspartic acid. The salts which are formed are, inter alia, hydrochlorides, chlorided, hydrobromides, bromides, iodides, sulfates, phosphates, methanesulfonates, tosylates, carbonates, bicarbonates, formates, acetates, sulfoacetates, triflates, oxalates, malonates, maleates, succinates, tartrates, malates, embonates, mandelates, fumarates, lactates, citrates, glutarate, stearate, aspartates and glutamates. The stoichiometry of the salts formed from the compounds of the invention may moreover be an integral or non-integral multiple of one.

The compounds of the invention can, if they contain a sufficiently acidic group such as, for example, the carboxy, sulfonic acid, phosphoric acid or a phenolic group, be converted with inorganic and organic bases into their physiologically tolerated salts. Examples of suitable inorganic bases are ammonium, sodium hydroxide, potassium hydroxide, calcium hydroxide, and of organic bases are ethanolamine, diethanolamine, triethanolamine, ethylenediamine, t-butylamine, t-octylamine, dehydroabietylamine, cyclohexylamine, dibenzylethylene-diamine and lysine. The stoichiometry of the salts formed from the compounds of the invention can moreover be an integral or non-integral multiple of one.

It is likewise possible for the compounds of the invention to be in the form of their solvates and, in particular, hydrates which can be obtained for example by crystallization from a solvent or from aqueous solution. It is moreover possible for one, two, three or any number of solvate or water molecules to combine with the compounds of the invention to give solvates and hydrates.

It is known that chemical substances form solids which exist in different order states which are referred to as polymorphic forms or modifications. The various modifications of a polymorphic substance may differ greatly in their physical properties. The compounds of the invention can exist in various polymorphic forms, and certain modifications may moreover be metastable. All these polymorphic forms of the compounds of the invention are to be regarded as belonging to the invention.

The compounds of the invention are advantageously characterized by a strong biological action. With regard to the disorazole conjugates of the present invention, they are superior to prior art conjugates due to an increased inherent potency. Furthermore, in particular the bis-substituted C1-B1-A-B2-C2 conjugates surprisingly display a higher specificity and reduced toxicity before release of the cytotoxic disorazole moiety.

With the conjugates of the present invention, specific targeting of (tumor) tissues of interest is possible, for instance via use of a desired receptor-ligand as cell-binding molecule that directs the conjugate to such receptor-expressing (tumor) tissues. More-over, the specific targeting advantageously results in high local concentrations of the conjugates in situ (at the tumor site) leading to a significantly increased efficacy. These advantages may translate into dose reductions of a potential drug administered in the clinic as well as less or no medicinal adverse effects.

In another aspect, the object of the present invention has been surprisingly solved by providing a process of manufacturing the compounds of the invention.

In a preferred embodiment, a process of manufacturing the compounds of the invention is provided comprising the steps:
a) reacting a disorazole compound with a linker, preferably a linker anhydride, to yield a mono- and/or bisfunctionalized disorazole-linker moiety,
b) optionally, separation (purification) of the mono- and/or bisfunctionalized disorazole-linker moiety from reaction educts and side products,
c) coupling of the optionally separated (purified) mono- and/or bisfunctionalized disorazole-linker moiety with cell-binding molecules to yield a disorazole conjugate of formula (I) C1-B1-A-B2-C2 and/or formula (IV) C1-B1-A,
d) optionally, separation (purification) of the disorazole conjugate of formula (I) C1-B1-A-B2-C2 and/or formula (IV) C1-B1-A from reaction educts and side products.

The compounds of the invention can be administered to various mammalian species, including human, for the treatment or prophylaxis of physiological and/or pathophysiological conditions.

For the purpose of the present invention, all mammalian species are regarded as being comprised. Preferably, such mammals are selected from the group consisting of human, domestic animals, cattle, livestock, pets, cow, sheep, pig, goat, horse, pony, donkey, hinny, mule, hare, rabbit, cat, dog, guinea pig, hamster, rat, mouse. More preferably, such mammals are human.

In another aspect, the object of the present invention has been surprisingly solved by providing the compounds of the invention for the manufacture of a medicament.

In another aspect, the object of the present invention has been surprisingly solved by providing the compounds of the invention for the manufacture of a medicament for the treatment and/or prophylaxis of "acute leukemia, adenocarcinoma, basalioma, benign tumors, bladder cancer, bowel cancer, brain tumors, breast cancer, bronchial carcinoma, carcinoids, carcinomas, cervical cancer, cervical carcinoma, chronic leukemia, colon cancer, colon carcinoma, colorectal cancer, connective tissue cancer, corpus carcinoma, endometrial cancer, esophageal cancer, Ewing-Sarcoma, gastrinoma, glioblastoma, glioma, gynaecological tumors, head and/or neck cancer, hepatoblastoma, hepatoma, hyperplasia, hyperproliferative diseases, intraocular melanoma, Kaposi-Sarcoma, laryngeal carcinoma, larynx cancer, leimoyoma, leukemia, liver tumor, lung cancer, non-small cell lung cancer, lymphoma, malign tumors, mamma carcinoma, medulloblastoma, melanoma, multiple myeloma, nephroblastoma, neuroblastoma, neuroendocrine tumors, osteosarcoma, ovarian cancer, pancreas tumor, prostate cancer, prostate carcinoma, rectal carcinoma, renal cancer, renal cell carcinoma, retinoblastoma, rhabdoid tumor, sarcomas, skin cancer, soft part sarcoma, solid tumors, spinalioma, stomach cancer, testicular cancer, thymoma, thyroid gland cancer, tumors starting from the brain and/or nervous system and/or meninges (WO 99/01764), urinary cancer and/or uterus cancer.

In a further aspect, the object of the present invention has been surprisingly solved by providing the compounds of the invention for the manufacture of a medicament, wherein the medicament further comprises at least one additional pharmaceutically active substance.

In a further aspect, the object of the present invention has been surprisingly solved by providing the compounds of the invention for the manufacture of a medicament, wherein the medicament is applied before and/or during and/or after treatment with at least one additional pharmacologically active substance.

In a further aspect, the object of the present invention has been surprisingly solved by providing the compounds of the invention for the manufacture of a medicament, wherein the medicament is administered before and/or during and/or after radiation therapy treatment and/or surgery.

In the course of the present invention, the compounds of the invention can thereby be administered as illustrated as single substances or in combination with all known pharmacologically active substances in the course of a combination therapy.

In a preferred embodiment, the compounds of the invention are provided for above illustrated uses, wherein the additional pharmacologically active substance is selected from the group consisting of: DNA topoisomerase I and/or II inhibitors, DNA intercalators, alkylating agents, microtubule destabilisators, hormone- and/or growth-factor-receptor-agonists and/or -antagonists, inhibitors of signal transduction, antibodies against growth factors and their receptors, kinase inhibitors, anti-metabolites.

In a preferred embodiment, the compounds of the invention are provided for above illustrated uses, wherein the additional pharmacologically active substance is selected from the group consisting of: actinomycin D, aminoglutethimide, asparaginase, avastin, azathioprin, BCNU (carmustine), bleomycin, busulfan, carboplatin, CCNU (lomustine), chlorambucil, cisplatin, colaspase, cyclophosphamide, cytarabin, dactinomycin, daunorubicin, diethylstilbestrole, docetaxel, doxorubicin (adriamycin), DTIC (dacarbacin), epirubicin, epothilone, erbitux, erythrohydroxynonyladenine, ethinylestradiole, etoposide, fludarabine phosphate, fluoxymesterone, flutamide, gemcitabine, gleevec/glivec, herceptin, hexamethylrmelamine, hydroxurea, hydroxyprogesterone caproate, idarubicin, ifosfamide, interferone, iressa, irinotecan, L-asparaginase, leucovorine, mechlorethamine, medroxyprogesterone acetate, megestrole acetate, melphalan, mesna, methotrexate, mitomycin C, mitotan, mitoxantrone, N-phosphonoacetyle-L-aspartate (PALA), oxaliplatin, paclitaxel, pentostatine, plicamycin, prednisolone, prednisone, procarbazine, raloxifen, rapamycin, semustin, sorafenib, streptozocin, tamoxifen, tarceva, taxotere, teniposide, testosterone propionate, thioguanine, thiotepa, topotecan, trimethylemelamine, uridine, vinblastine, vincristin, vindesine, vinorelbin, 2',2'-difluorodeoxycytidine, 5-fluorodeoxyuridine monophosphate, 5-azacytidine cladribine, 5-fluorodeoxyuridine, 5-fluorouracile (5-FU), 6-mercaptopurine.

The compounds of the present invention can be administered in a known manner. The route of administration may thereby be any route which effectively transports the active compound to the appropriate or desired site of action, for example non-orally or orally, in particular intravenously, topically, transdermally, pulmonary, rectally, intravaginally, nasally or parenteral or by implantation. Intravenous administration is preferred.

The compounds of the invention are converted into a form which can be administered and are mixed where appropriate with pharmaceutically acceptable carriers or diluents. Suitable excipients and carriers are described for example in Ullman's Encyclopedia of Technical Chemistry, Vol. 4, (1953), 1-39; Journal of Pharmaceutical Sciences, Vol. 52 (1963), 918 et seq.; H. v. Czetsch-Lindenwald, Hilfsstoffe für Pharmazie and angrenzende Gebiete; Pharm. Ind. 2, 1961, 72 et seq.; Dr. H. P. Fiedler, "Lexikon der Hilfsstoffe für Pharmazie, Kosmetik and angrenzende Gebiete, Cantor K G, Aulendorf in Württemberg, 1971.

Non-oral administration can take place for example by intravenous, subcutaneous, intramuscular injection of sterile aqueous or oily solutions, suspensions or emulsions, by means of implants or by ointments, creams or suppositories. Administration as sustained release form is also possible where appropriate. Implants may comprise inert materials, e.g. biodegradable polymers or synthetic silicones such as, for example, silicone rubber. Intravaginal administration is possible for example by means of vaginal rings. Intrauterine administration is possible for example by means of diaphragms or other suitable intrauterine devices. Transdermal administration is additionally provided, in particular by means of a formulation suitable for this purpose and/or suitable means such as, for example, patches.

Oral administration can take place for example in solid form as tablet, capsule, gel capsule, coated tablet, granulation or powder, but also in the form of a drinkable solution. The compounds of the invention can for oral administration be combined with known and ordinarily used, physiologically tolerated excipients and carriers such as, for example, gum arabic, talc, starch, sugars such as, for example, mannitol, methylcellulose, lactose, gelatin, surface-active agents, magnesium stearate, cyclodextrins, aqueous or nonaqueous carriers, diluents, dispersants, emulsifiers, lubricants, preservatives and flavorings (e.g. essential oils). The compounds of the invention can also be dispersed in a microparticulate, e.g. nanoparticulate, composition.

As already explained above, the compounds of the invention can also be combined with other active pharmaceutical ingredients. It is possible for the purposes of the combination therapy to administer the individual active ingredients simultaneously or separately, in particular either by the same route (e.g. intravenously) or by separate routes (e.g. intravenously and as oral application). They may be present and administered in identical or different amounts in a unit dose. It is also possible to use a particular dosage regimen when this appears appropriate. It is also possible in this way to combine a plurality of the novel compounds of the invention of the general formulae with one another.

The dosage may vary within a wide range depending on type and/or severity of the physiological and/or pathophysiological condition, the mode of administration, the age, gender, bodyweight and sensitivity of the subject to be treated. It is within the ability of a skilled worker to determine a pharmacologically effective amount of a compound of the invention and/or additional pharmacologically active substance. Administration can take place in a single dose or a plurality of separate dosages.

A suitable unit dose is, for example, from 0.0001 mg to 100 mg of the active ingredient, i.e. at least one compound of the invention and, where appropriate, at least one additional pharmacologically active substance, per kg of a patient's bodyweight.

In another aspect, the present invention relates to a pharmaceutical composition comprising a pharmacologically active amount of at least one compound of the invention, in particular "disorazole A1-succinyl-[D-Lys$^6$]LHRH (regioisomeric compounds 11 and 12), disorazole E1-succinyl-[D-Lys$^6$]LHRH (regioisomeric compounds 13 and 14), disorazole A1-(succinyl-[D-Lys$^6$]LHRH)$_2$ (compound 15), disorazole Z-succinyl-[D-Lys$^6$]LHRH (compound 16), disorazole Z-(glutaryl-[D-Lys$^6$]LHRH)$_2$ (compound 17), disorazole Z-succinyl-somatostatin (compound 18), regioisomeric compounds 1 and 2, compound 3, compound 4, regioisomeric compound 5 and 6, compound 7, compound 9, compound 10, compound 19, compound 20, compound 21.

In a further aspect, such a pharmaceutical composition may additionally comprise at least one pharmaceutically acceptable carrier and/or excipient and/or may comprise at least one further pharmacologically active substance.

In a preferred embodiment, such further pharmacologically active substance is selected from the group consisting of: DNA topoisomerase I and/or II inhibitors, DNA intercalators, alkylating agents, microtubule destabilisators, hormone- and/or growth-factor-receptor-agonists and/or -antagonists, inhibitors of signal transduction, antibodies against growth factors and their receptors, kinase inhibitors, anti-metabolites.

In a further preferred embodiment, such further pharmacologically active substance is selected from the group consisting of: actinomycin D, aminoglutethimide, asparaginase, avastin, azathioprin, BCNU (carmustine), bleomycin, busulfan, carboplatin, CCNU (lomustine), chlorambucil, cisplatin, colaspase, cyclophosphamide, cytarabin, dactinomycin, daunorubicin, diethylstilbestrole, docetaxel, doxorubicin (adriamycin), DTIC (dacarbacin), epirubicin, epothilone, erbitux, erythrohydroxynonyladenine, ethinylestradiole, etoposide, fludarabine phosphate, fluoxymesterone, flutamide, gemcitabine, gleevec/glivec, herceptin, hexamethylrmelamine, hydroxurea, hydroxyprogesterone caproate, idarubicin, ifosfamide, interferone, iressa, irinotecan, L-asparaginase, leucovorine, mechlorethamine, medroxyprogesterone acetate, megestrole acetate, melphalan, mesna, methotrexate, mitomycin C, mitotan, mitoxantrone, N-phosphonoacetyle-L-aspartate (PALA), oxaliplatin, paclitaxel, pentostatine, plicamycin, prednisolone, prednisone, procarbazine, raloxifen, rapamycin, semustin, sorafenib, streptozocin, tamoxifen, tarceva, taxotere, teniposide, testosterone propionate, thioguanine, thiotepa, topotecan, trimethylemelamine, uridine, vinblastine, vincristin, vindesine, vinorelbin, 2',2'-difluorodeoxycytidine, 5-fluorodeoxyuridine monophosphate, 5-azacytidine cladribine, 5-fluorodeoxyuridine, 5-fluorouracile (5-FU), 6-mercaptopurine.

Concerning the pharmaceutical compositions of the invention, at least one compound of the invention is present in a pharmacologically effective amount, preferably in a unit dose, e.g. the aforementioned unit dose, specifically and preferably in an administration form which makes intravenous administration possible. Furthermore, reference may be made to that already said in connection with the possible uses and administrations of the compounds of the invention.

In a further aspect, the object of the present invention has surprisingly been solved by providing a kit comprising a pharmacologically active amount of at least one compound of the invention and a pharmacologically active amount of at least one additional pharmaceutically active substance as defined above.

Chemical Synthesis:

General synthetic methods for the generation of disorazole conjugates of the general formulae (I) C1-B1-A-B2-C2 and (IV) C1-B1-A are given in this section.

Total synthesis and/or isolation strategies for obtaining disorazoles are known in the prior art and are, for instance, described in the following prior art documents: Jansen R et al., Liebigs Ann. Chem. 1994, (8): 759-773; WO 2004/024149; Wipf et al., Chem. Biol. Drug Des. 2006, 67(1): 66-73); Hillier M C et al., J. Org. Chem. 2001, 66: 6037-6045; Hartung I V et al., Organic Letters 2002, 4(19): 3239-3242; Wipf P et al., J. Am. Chem. Soc. 2004, 126(47): 15346-15347; Carvalho R et al., Gene 2005, 359: 91-98; Kopp M et al., Chembiochem. 2005, 6(7): 1277-1286; WO 2006/075013.

Disorazole Z

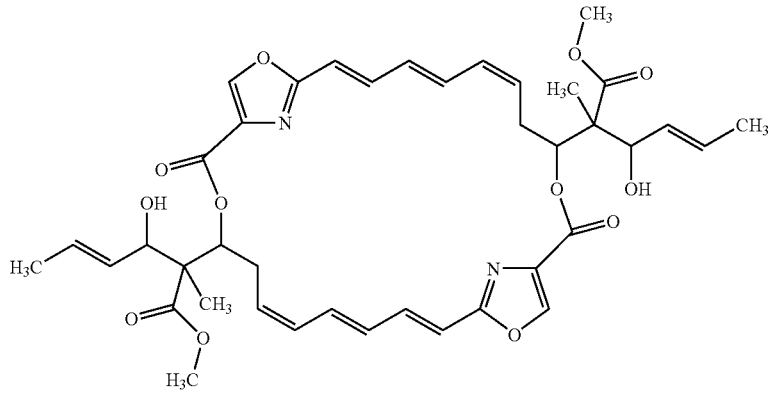

(disorazole Z)

can either be fully chemically synthesized according to above listed prior art descriptions or produced by fermentation as illustrated under II) in the example section.

The synthesis of conjugates according the invention was performed via common solution based organic chemistry.

A. Derivatization of Disorazole Secondary Hydroxyl Groups Via Esterfication with Organic Anhydrides In a typical reaction, the solid disorazole was dissolved in water free pyridine, previously dried over molecular sieve (40 nm). Under nitrogen atmosphere, 1-2.5 mol equivalents DMAP and 1.5-10 mol equivalents of the organic anhydride (glutaric anhydride, succinic anhydride) were added as calculated for either mono or bis-esterfication of the two secondary OH-groups available within the different disorazole molecules. Mol sieve was added optionally to the reaction in order to ensure water free conditions at all times. The mixture was stirred for 6 h-5 d, optionally at room temperature or 60° C. bath temperature, with regard to the respective desired derivatives. Esterfication was monitored by analytical HPLC-UV.

Typical Analytical HPLC-Conditions:
Eluent A: 20 mM $NH_4OAc$, 5% (v/v) AcN, 0.2% (v/v) HOAc
Eluent B: 95% (v/v) AcN, 5% (v/v) $H_2O$
Column: Merck LiChrosphere 100 $C_{18}$, 5 µm, 250×4 mm
Flow: 1 ml/min
Detection: UV-DAD, 220-380 nm
Gradient: 40%-100% B in 18 min, 100% B for 5 min, 100%-40% B in 2 min Purification of the mono or bis-esterfied disorazole was performed either by automated flash liquid chromatography using the Isco Companion system or by preparative HPLC. Therefore, the excess pyridine of the reaction mixture was removed under reduced pressure and the oily residue acidified with 10% acetic acid to pH 4-6. For Companion purification, the acidified aqueous phase was extracted several times with ethyl acetate, the organic extracts combined, dried over sodium sulfate and adsorbed to RP carrier material under reduced pressure. Flash chromatography was used for purification of bis-esterfied disorazoles and carried out under reversed phase conditions with 5% AcN (v/v), 0.1% HOAc as eluent A and 95% AcN as eluent B.

For preparative HPLC, the acidified aqueous mixture was diluted with starting eluent (50% B), filtered through a syringe filter membrane and injected into the preparative HPLC system.

Typical Preparative HPLC-Conditions:
Eluent A: 20 mM NH$_4$OAc, 5% (v/v) AcN, 0.2% (v/v) HOAc
Eluent B: 95% (v/v) AcN, 5% (v/v) H$_2$O
Column: Macherey&Nagel VarioPrep Nucleodur 100 C$_{18}$, 7 μm, 250×21 mm
Flow: 20 ml/min
Detection: UV
Gradient: 50% B for 5 min, 50%-100% B in 25 min, 100% B for 10 min LC fractions containing the desired products were analyzed by analytical HPLC, freed from AcN and HOAc under reduced pressure and the aqueous concentrate lyophilized to give the respective esters as solid compounds.

B. Amide Coupling of Disorazole Mono and Bis Hemi-Carboxylic Esters with Peptides The mono and bis functionalized carboxylic derivatives of disorazole were coupled to peptides via a classic amide coupling strategy. In brief, the carboxylic disorazole compound was dissolved in dry DMF with 3-6 mol equivalents of DIPEA and activated by addition of 1.1-1.5 mol equivalents of HATU per free carboxyl residue and subsequent stirring for 15 minutes at ambient temperature. The peptidic compound bearing a free amino group was then added at a slight molar excess (1.1-1.3 eq) and the reaction mixture stirred for 0.5-12 h at room temperature. Coupling efficiency was monitored via analytical HPLC (method described above).

For preparative HPLC purification the DMF solution was acidified to pH 5-6 with 10% HOAc and diluted with 4-6 volumes of starting eluent (40-50% B). The same typical preparative HPLC method was employed as described above. Pure conjugates were obtained after analytical HPLC evaluation of the respective fraction, removing of AcN and HOAc under reduced pressure and subsequent lyophilization of the aqueous concentrate.

C. Amide Coupling of Disorazole Bis Hemi-Carboxylic Esters with Serum Albumin

Coupling of functionalized disorazole derivatives to larger proteins such as serum albumin was carried out using the NHS/DCC method. Different molar ratios of protein and disorazole compound were used to achieve various loading rates of disorazole and the carrier protein. In a typical reaction, serum albumin was dissolved in 10 mM PBS pH 7.4 at an initial concentration of 20 mg/ml. Subsequent 1:1 (v/v) dilution with DMF gave a clear serum albumin solution with a final concentration of 10 mg/ml. Disorazole bis or mono hemi carboxylic esters were dissolved in DMF, 1.2-5 equivalents of DCC and 2-10 equivalents of NHS was added and stirred for 20 min to allow formation of the activated NHS-ester. Efficiency of activation was estimated by analytical HPLC (for typical method see above). Distinct aliquots of this solution were added drop wise and under vigorous stirring to the serum albumin buffer/DMF solution. Ratios of disorazole-NHS ester and serum albumin were chosen with regard to different loading rates based on empiric data. The aqueous amide coupling was carried out or 20 minutes at ambient temperature. The slightly cloudy reaction mixture was then vacuum-filtered through a SteriCup Filter (Milipore) and the filter washed with de-ionized water. The filtrate was then diluted with de-ionized water and low molecular compounds were separated by ultrafiltration. Therefore, the diluted SteriCup filtrate was placed into a AmiconUltra (milipore) filtration unit with an exclusion size of 30.000 Da and centrifuged at 4.000×g for 15 min. The concentrated, retained protein solution was washed 3 times with deionized water and centrifuged to remove all excess salts, DMF and unbound disorazole and DCC/NHS. The purified serum albumin disorazole conjugate solution was subsequently yophilized to give pale yellow colored crystals. The ultra filtrate was analyzed for unbound disorazole by analytical HPLC using the typical method described above in order to estimate mean loading rates of disorazole per serum albumin molecule.

D. Oxidation of Disorazoles with Dess-Martin Periodinane Reagent

Disorazoles (A1, E1 or Z for example) were dissolved in dichloromethane. 12 Mol equivalents of pyridine were added and the mixture was cooled down to less than 5° C. on an ice bath. 3 Mol equivalents of Dess-Martin periodinane reagent (triacetoxyperiodinane) was added in several portions and the reaction was allowed to stirr on the ice bath for 15 minutes. The mixture was warmed to room temperature and stirring was continued for 30 minutes (TLC control with dichloromethane/methanol 95:5). The reaction mixture was diluted with ethyl acetate and poured onto 0.5N hydrochloric acid. The organic phase was washed with brine until almost neutral (pH 6), dried over sodium sulfate and reduced in vacuo. Subsequent flash chromatography with dichloromethane/methanol provided the disorazole-ketone derivatives.

E. Abbreviations

| | |
|---|---|
| 5-FU | 5-fluorouracile |
| AcN | acetonitrile |
| Ala | alanine(yl) |
| Aloc | allyloxycarbonyl |
| Arg | arginine(yl) |
| Asn | asparagine(yl) |
| BCNU | carmustine |
| Boc | tert. Butyloxycarbonyl |
| Cbz | carbobenzoxycarbonyl |
| CCNU | lomustine |
| Cit | citrulline |
| DCC | N,N'-dicyclohexylcarbodiimide |
| DCM | dichlormethane |
| DIPEA | diisopropylethyl amine |
| DMAP | N,N'-4-dimethylamino pyridine |
| DMEM | Dulbecco's Modified Eagles Medium |
| DMF | N,N'-Dimethylformamid |
| DMSO | dimethylsulfoxide |
| Dox | doxorubicin |
| DTIC | dacarbacin |
| e.g. | example given |
| EDTA | ethylendiamine-tetraacetic acid |
| ELISA | Enzyme Linked Immunosorbent Assay |
| Fmoc | 9-fluorenylmethoxycarbonyl |
| Gln | glutamine(yl) |
| Glp | pyroglutamate(yl) |
| h | hour |
| HATU | N,N,N',N'-tetramethyl-O-(7-azabenzotriazol-1-yl)uronium hexafluorophosphat |
| HEPES | N-(2-hydroxyethyl)piperazin-N'-2-ethansulfonsäure |
| HOAc | acetic acid |
| HOBt | 1-hydroxybenzotriazole |
| HSA | human serum albumin |
| hTyr | homo-tyrosine(yl) |
| Hyp | Hydroxyproline |
| Ile | isoleucine(yl) |
| IPA | isopropyl alcohol |
| Leu | leucine(yl) |
| LH | luteinizing hormone |
| LHRH (GnRH) | luteinizing hormone releasing hormone |
| LHRH-R | luteinizing hormone releasing hormone receptor |
| Lys | lysine(yl) |
| MDS | methyldisulfanyl |
| Me | methyl |

-continued

| | |
|---|---|
| D-/L-Mel | (4-[bis(2-chloroethyl)amino]-D/L-phenylalanine) |
| MeOH | methanol |
| min | minute |
| ml | milliliter |
| NHS | N-hydroxysuccinimide |
| Nle | norleucin |
| PALA | N-phosphonoacetyl-L-aspartate |
| PEG2 | polyethylenglycole consisting of 2 ethylen glycole moeities |
| PEG3 | polyethylenglycole consisting of 3 ethylen glycole moeities |
| PEG7 | polyethylenglycole consisting of 7 ethylen glycole moeities |
| PMS | N-methyldibenzopyrazinemethylsulfate |
| Pyr | pyroglutamate(yl) |
| RIA | Radio Immuno Assay |
| RT | room temperature |
| Sar | sarcosine |
| tBu | tert. butyl |
| TEA | triethyl amine |
| TFA | trifluoro acetic acid |
| THF | tetrahydrofuran |
| TLC | thin layer chromatography |
| Tpi | tetrahydronorharman-3-carboxylic acid |
| trityl | triphenylcarbonyl |
| Tyr | tyrosine(yl) |
| Val | valine(yl) |
| XTT | sodium 3'-[1-(phenylaminocarbonyl)-3,4-tetrazolium]-bis(4-methoxy-6-nitro)benzenesulfonic acid |

5-FU 5-fluorouracile

AcN acetonitrile

Ala alanine(yl)

Aloc allyloxycarbonyl

Arg arginine(yl)

Asn asparagine(yl)

BCNU carmustine

Boc tent. Butyloxycarbonyl

Cbz carbobenzoxycarbonyl

CCNU lomustine

Cit citrulline

DCC N,N'-dicyclohexylcarbodiimide

DCM dichlormethane

DIPEA diisopropylethyl amine

DMAP N,N'-4-dimethylamino pyridine

DMEM Dulbecco's Modified Eagles Medium

DMF N,N'-Dimethylformamid

DMSO dimethylsulfoxide

Dox doxorubicin

DTIC dacarbacin e.g. example given

EDTA ethylendiamine-tetraacetic acid

ELISA Enzyme Linked Immunosorbent Assay

Fmoc 9-fluorenylmethoxycarbonyl

Gln glutamine(yl)

Glp pyroglutamate(yl)

h hour

HATU N,N,N',N'-tetramethyl-O-(7-azabenzotriazol-1-yl) uronium hexafluorophosphat HEPES N-(2-hydroxyethyl)piperazin-N'-2-ethansulfonsäure HOAc acetic acid HOBt 1-hydroxybenzotriazole HSA human serum albumin hTyr homo-tyrosine(yl)

Hyp Hydroxyproline

Ile isoleucine(yl)

IPA isopropyl alcohol

Leu leucine(yl)

LH luteinizing hormone

LHRH (GnRH) luteinizing hormone releasing hormone

LHRH-R luteinizing hormone releasing hormone receptor

Lys lysine(yl)

MDS methyldisulfanyl

Me methyl

D-/L-MeI (4-[bis(2-chloroethyl)amino]-D/L-phenylalanine)

MeOH methanol min minute ml milliliter

NHS N-hydroxysuccinimide

Nle norleucin

PALA N-phosphonoacetyl-L-aspartate

PEG2 polyethylenglycole consisting of 2 ethylen glycole moeities

PEG3 polyethylenglycole consisting of 3 ethylen glycole moeities

PEG7 polyethylenglycole consisting of 7 ethylen glycole moeities

PMS N-methyldibenzopyrazinemethylsulfate

Pyr pyroglutamate(yl)

RIA Radio Immuno Assay

RT room temperature

Sar sarcosine tBu tert. butyl

TEA triethyl amine

TFA trifluoro acetic acid

THF tetrahydrofuran

TLC thin layer chromatography

Tpi tetrahydronorharman-3-carboxylic acid trityl triphenylcarbonyl

Tyr tyrosine(yl)

Val valine(yl)

XTT sodium 3'-[1-(phenylaminocarbonyl)-3,4-tetrazolium]-bis(4-methoxy-6-nitro)benzenesulfonic acid

BRIEF DESCRIPTION OF THE DRAWINGS

FIGS. 1-17 show the measured H-NMR spectra of selected compounds of the invention: compounds 1/2, 3, 4, 5/6, 7, 8, 9, 10, 11/12, 13/14, 15, 16, 17, 18, 19, 20, 21.

The contents of all cited references and patents are hereby incorporated by reference. The invention is explained in more detail by means of the following examples without, however, being restricted thereto.

EXAMPLES
I) Synthesis of Compounds of the Invention
Example 1
Disorazole E1 Mono Hemi-Succinate, Both Regio-Isomers (1) & (2)
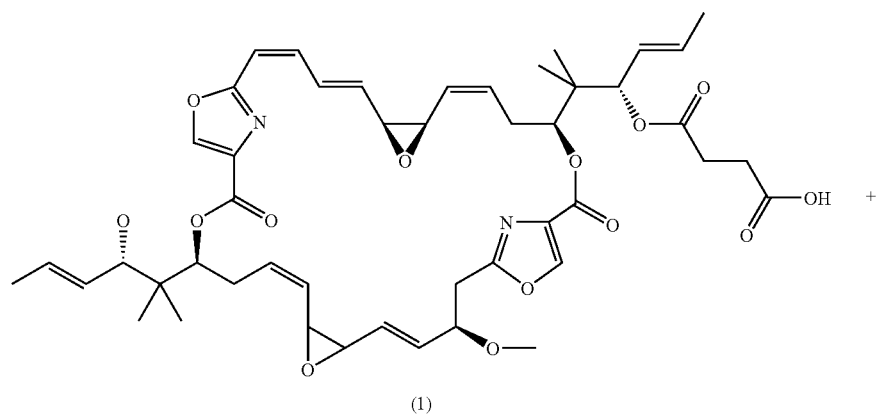
(1)
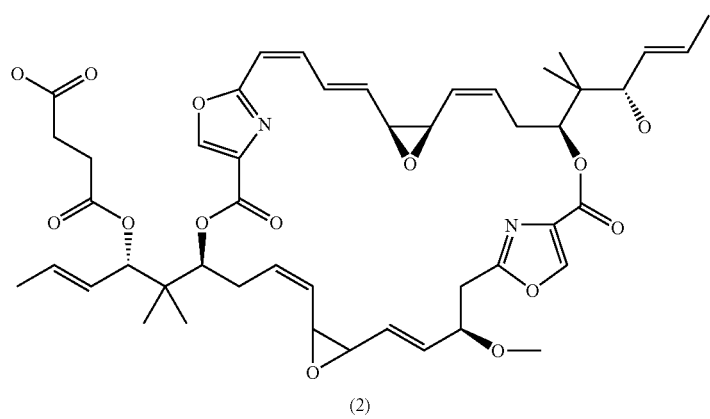
(2)

According to the general synthesis procedure listed under A., 30 mg disorazole E1, 12 mg DMAP and 150 mg succinic anhydride were dissolved in 2 ml dry pyridine and stirred for 4 days at RT under nitrogen. TLC-control: DCM-MeOH 9:1/DCM-IPA 9:1 plus analytical HPLC. The reaction mixture was poured on cold brine/0.5 M HCl and extracted with ethyl acetate, washed with brine to pH 4, dried over $Na_2SO_4$ and the excess solvent removed under reduced pressure. Purification of the raw product was performed by LC via Isco Companion using a DCM/MeOH gradient. 13 mg pure product was obtained as a 1:1 mixture of both regio-isomers 1 and 2 (combined yield: 39%).

LC-MS: $[M+H]^+$875.6 calculated mass: 874

Figure 1:
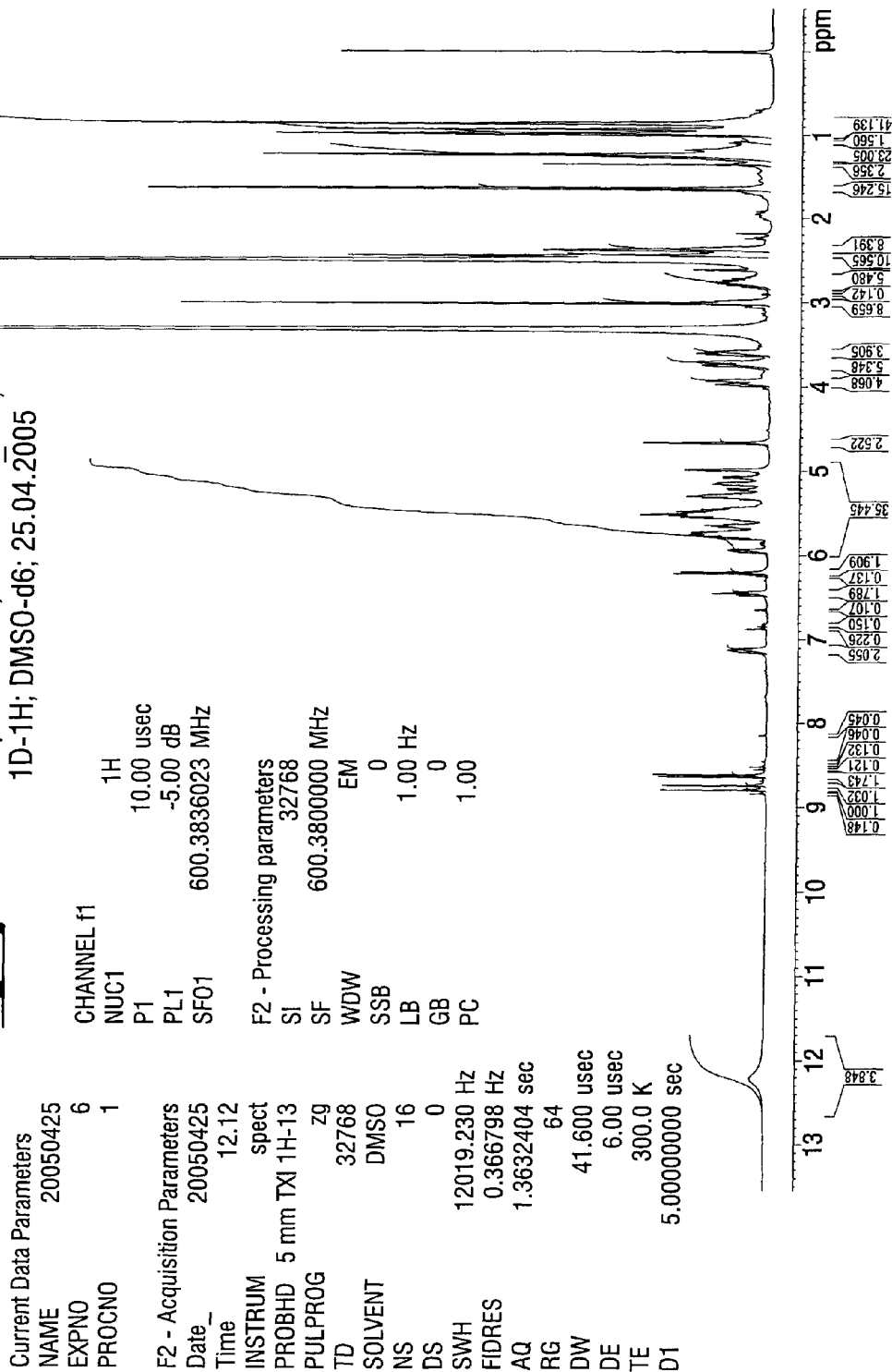

H-NMR: see FIG. 1

Example 2

Disorazole E1 Bis Hemi Glutarate (3)

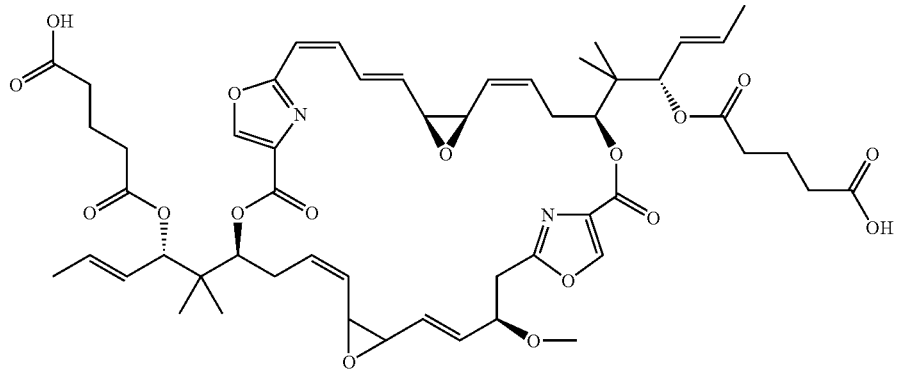

(3)

According to the general synthesis procedure listed under A., 100 mg disorazole E1, 30 mg DMAP and 150 mg glutaric anhydride were dissolved in 3 ml dry pyridine and 100 μl TEA was added and stirred for 4 days at RT under nitrogen. TLC-control: DCM-MeOH 9:1/DCM-IPA 9:1 plus analytical HPLC. The reaction mixture was poured on cold brine/0.5 M HCl and extracted with ethyl acetate, washed with brine to pH 4, dried over $Na_2SO_4$ and the excess solvent removed under reduced pressure. Purification of the raw product was performed by LC via Isco Companion using a DCM/MeOH gradient. 35 mg pure product was obtained (yield: 24%).

LC-MS: $[M+H]^+$1003.7 calculated mass: 1002

Figure 2:
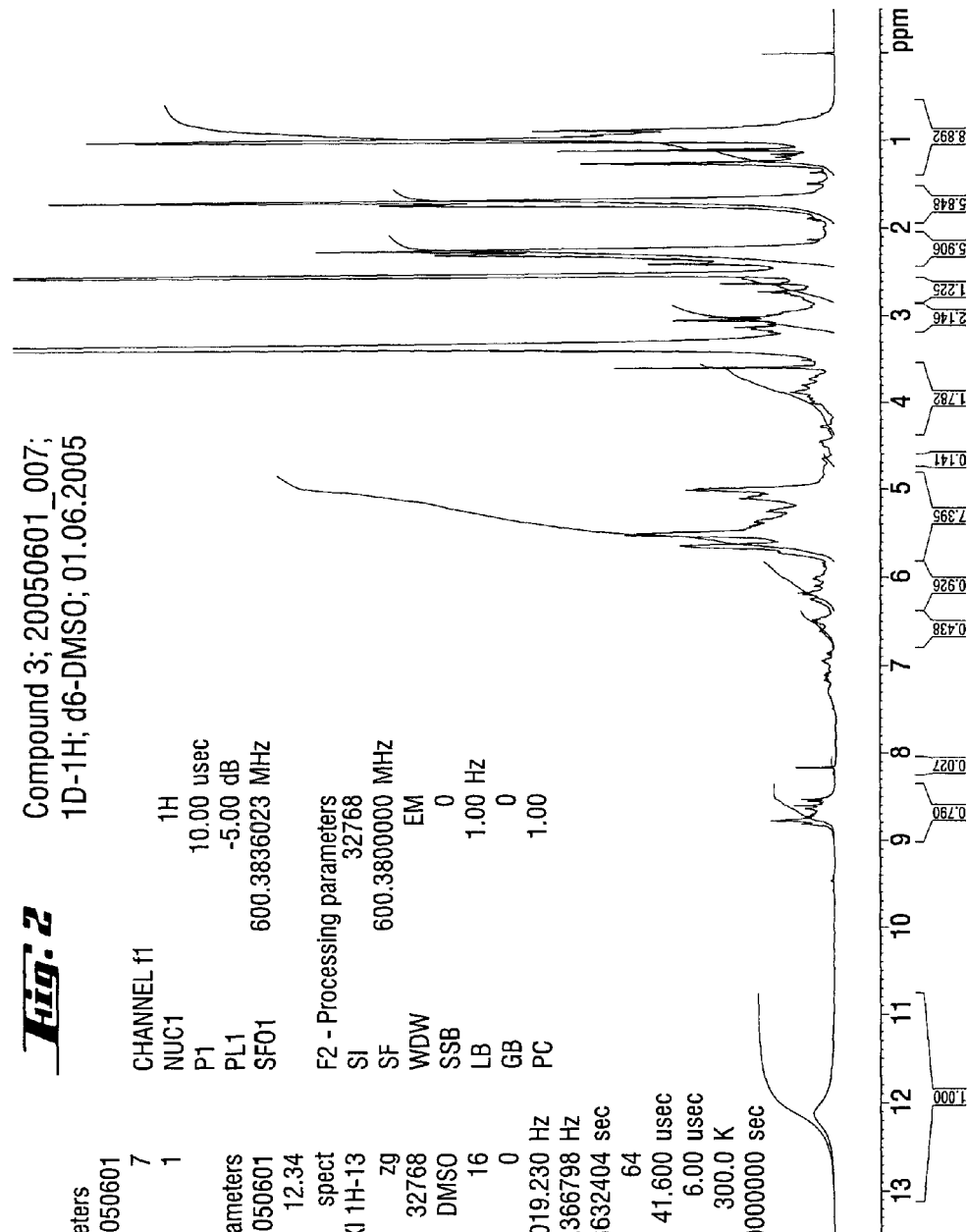

H-NMR: see FIG. 2

Example 3

Disorazole E1 Bis Hemi Succinate (4)

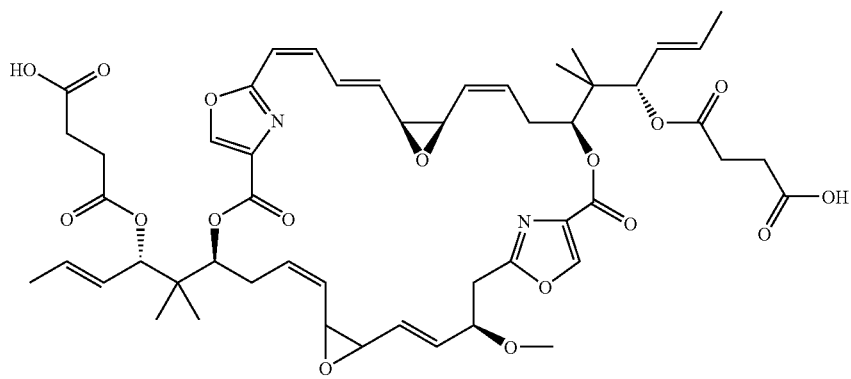

(4)

According to the general synthesis procedure listed under A., 138 mg disorazole E1, 70 mg DMAP and 730 mg succinic anhydride were dissolved in 10 ml dry pyridine, a spatula tip of mol sieve (4 A) was added and the reaction stirred for 4 days at RT under nitrogen. TLC-control: DCM-MeOH 9:1/ DCM-IPA 9:1 and analytical HPLC. The reaction mixture was diluted with ethyl acetate, poured on ice cold brine/HCl pH 3-4, extracted with ethyl acetate, the organic phase washed with brine until pH 4-5, dried over $Na_2SO_4$ and excess solvent removed under reduced pressure. Purification was performed via LC by Isco Companion with DCM/MeOH gradient to give 80 mg solid product (39% yield).

LC-MS: $[M+H]^+$ 975.5 calculated mass: 974

Figure 3:
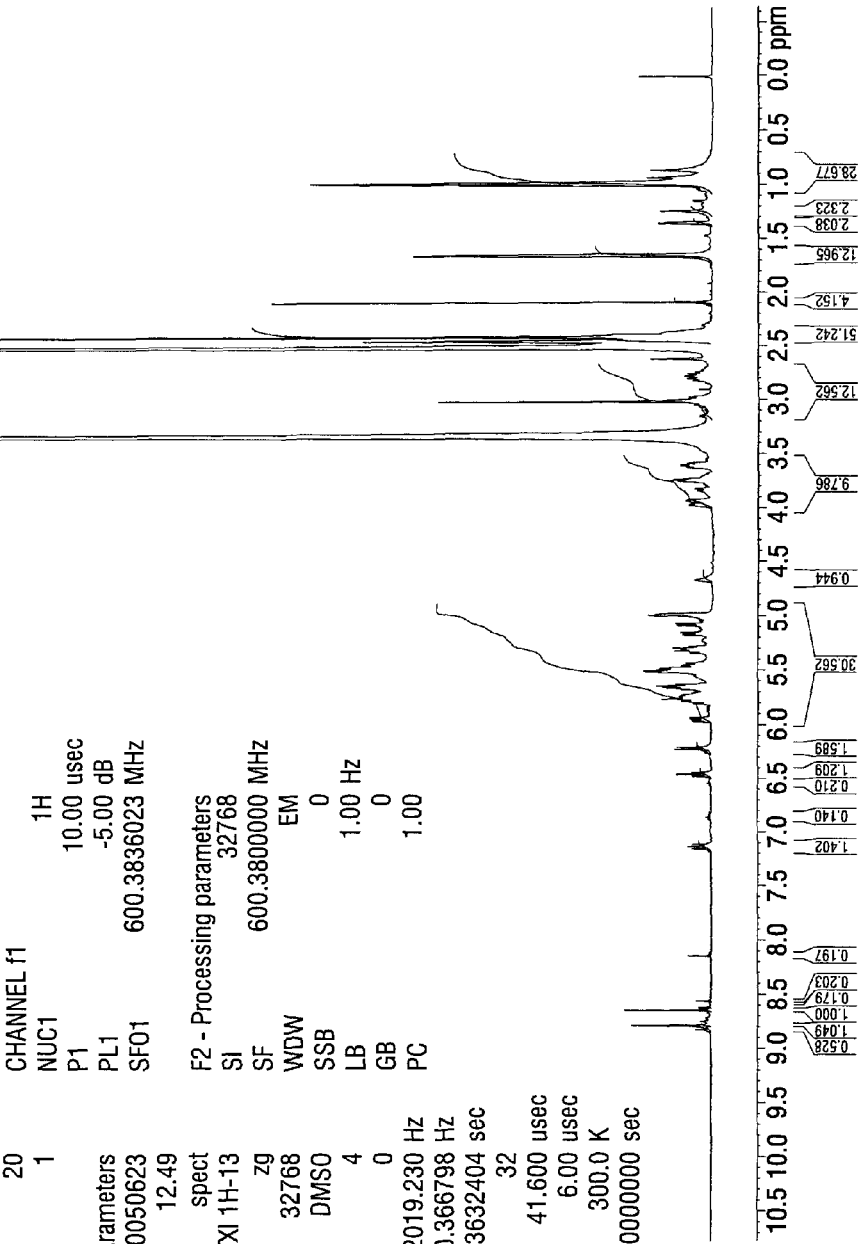

H-NMR: see FIG. 3

Example 4

Disorazole A1 Mono Hemi Succinate, Both Regio-Isomers (5) & (6)

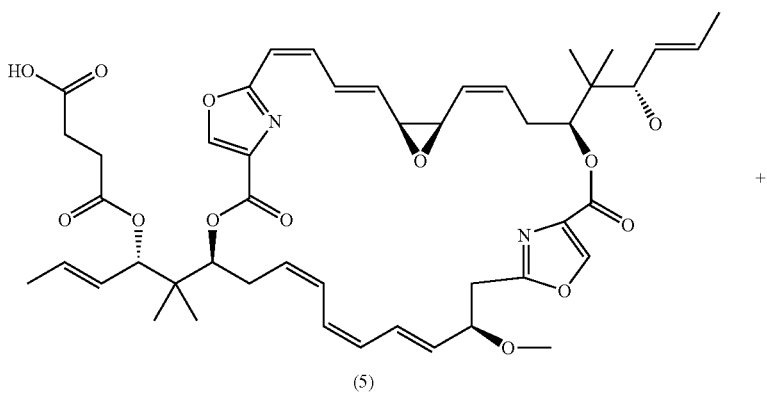

(5)

+

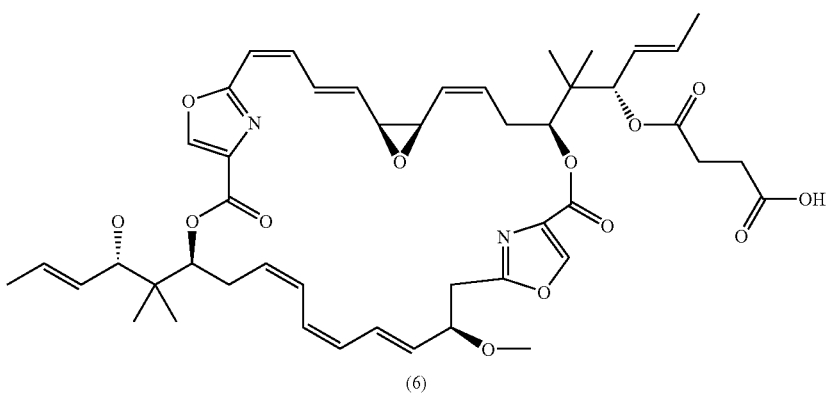

(6)

According to the general synthesis procedure listed under A., 30 mg disorazole A1, 15 mg DMAP and 160 mg succinic anhydride were dissolved in 2 ml dry pyridine and the reaction stirred for 4 days at RT under nitrogen. TLC-control: DCM-MeOH 9:1/DCM-IPA 9:1 and analytical HPLC. The reaction mixture was diluted with ethyl acetate, poured on ice cold brine/HCl pH 3-4, extracted with ethyl acetate, the organic phase washed with brine until pH 4-5, dried over $Na_2SO_4$ and excess solvent removed under reduced pressure. Purification was performed via LC by Isco Companion with DCM/MeOH gradient to give 5.3 mg solid product containing both region-isomers in a 1:1 ratio (15% combined yield).

LC-MS: $[M+H]^+$ 859.6
calculated mass: 858
H-NMR: see FIG. 4

Example 5

Disorazole A1 Bis Hemi Succinate (7)

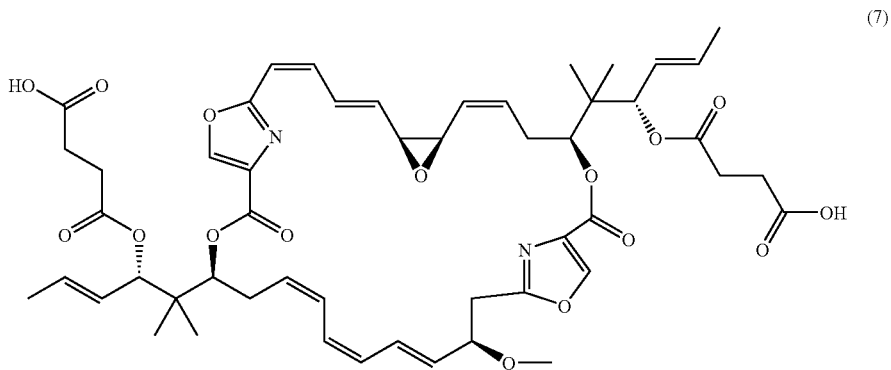 [SMILES: C/C=C/[C@H](OC(=O)CCC(=O)O)C(C)(C)[C@@H]1C\C=C/C=C\C=C\[C@H](OC)Cc2nc(co2)C(=O)O[C@H](C(C)(C)[C@H](/C=C/C)OC(=O)CCC(=O)O)C/C=C\[C@H]2O[C@H]2/C=C/C=C\c2nc(co2)C(=O)O1]

(7)

According to the general synthesis procedure listed under A., 138 mg disorazole A1, 70 mg DMAP and 730 mg succinic anhydride were dissolved in 10 ml dry pyridine, a spatula tip of mol sieve (4 A) was added and the reaction stirred for 4 days at RT under nitrogen. TLC-control: DCM-MeOH 9:1/DCM-IPA 9:1. The reaction mixture was diluted with ethyl acetate, poured on ice cold brine/HCl pH 3-4, extracted with ethyl acetate, the organic phase washed with brine until pH 4-5, dried over $Na_2SO_4$ and excess solvent removed under reduced pressure. Purification was performed via LC by Isco Companion with DCM/MeOH gradient to give 37 mg solid product 7 (yield: 20%).

LC-MS: $[M+H]^+$ 959.4
calculated mass: 958
H-NMR: see FIG. 5

Example 6

Disorazole Z Mono Hemi Succinate (8)

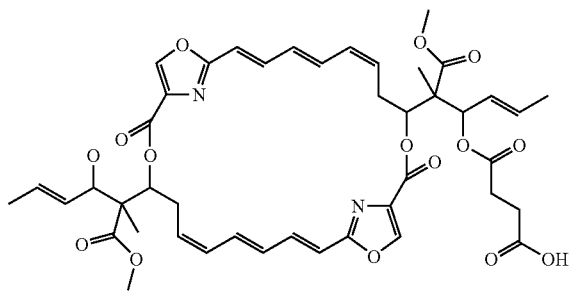

(8)

According to the general synthesis procedure listed under A., 80 mg Disorazol Z, 16 mg DMAP and 13 mg succinic anhydride were dissolved in 1.5 ml pyridine and a small portion of 4 A mol sieve was added to the reaction. The mixture was heated to 60° C. (oil bath temperature) and stirred for 24 h. The reaction was monitored via HPLC-UV. After cooling to room temperature, ethyl acetate was added and the mol sieve filtered off. The filtrate was evaporated to dryness under reduced pressure, the residue redissolved in 5 ml of a 40% solvent B mixture (A: 20 mM $NH_4AcO$, 5% AcN, 0.2% HOAc pH 4.5; B: 95% AcN, 5% water). After filtering through a luer lock membrane filter, the solution was injected into preparative HPLC (40% B→85% B in 25 min). The hemi mono succinate peaks was collected and the fraction lyophilized to give 31 mg of the pure product 8 as light brown solid (35%).

LC-MS: $[M+H]^+$ 847.0 calculated mass: 846

H-NMR: see FIG. 6

Example 7

Disorazole Z Bis Hemi Succinate (9)

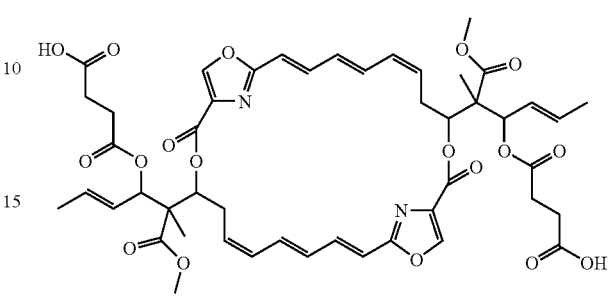

(9)

According to the general synthesis procedure listed under A., 188 mg disorazole Z, 31 mg DMAP and 500 mg succinic anhydride were dissolved in 4 ml pyridine and a small portion of 4 A mol sieve was added to the reaction. The mixture was heated to 40° C. (oil bath temperature) and stirred for 72 h. The reaction was monitored via HPLC-UV and TLC (DCM/MeOH 9:1). The reaction was diluted with DCM, transferred to an evaporator flask and the solvent removed under reduced pressure. The crude oil was again dissolved in DCM, adsorbed to RP18 silica gel, split into two similar fractions and used for RP-flash chromatography via Isco Companion LC (acetonitrile/water/0.1% acetic acid) with a 12 g RP column. Fraction #12-14 from run number 1 and fraction #2-3 from run number 2 were collected, unified and the solvent removed under reduced pressure/lyophilization. 105 mg of pale brown product was obtained (45%).

LC-MS: $[M+H]^+$ 947.3 calculated mass: 946

H-NMR: see FIG. 7

Example 8

Disorazole Z Bis Hemi Glutarate (10)

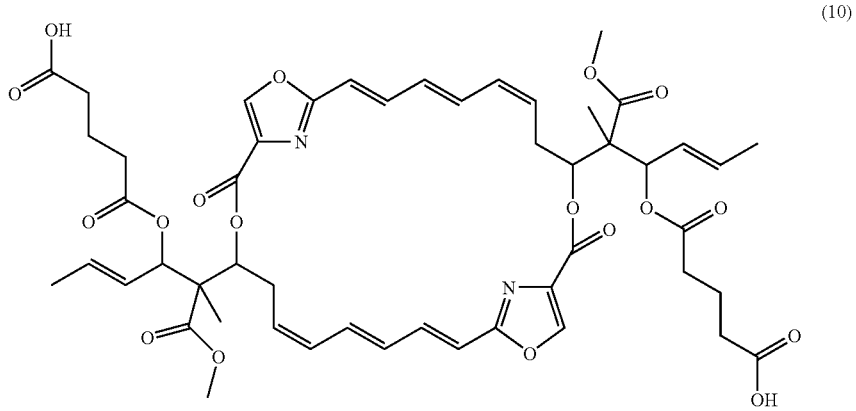 [SMILES: C/C=C/C(OC(=O)CCCC(=O)O)C(C)(C(=O)OC)C1C\C=C/C=C/C=C/c2nc(co2)C(=O)OC(C(C)(C(=O)OC)C(/C=C/C)OC(=O)CCCC(=O)O)C\C=C/C=C/C=C/c2nc(co2)C(=O)O1]

(10)

According to the general synthesis procedure listed under A., 183 mg Disorazol Z, 30 mg 4-DMAP and 560 mg glutaric anhydride were dissolved in 4 ml pyridine and a small portion of 4 A mol sieve was added to the reaction. The mixture was heated to 40° C. (oil bath temperature) and stirred for 72 h. The reaction was monitored via HPLC-UV and TLC (DCM/MeOH 9:1). The reaction was diluted with DCM, transferred to an evaporator flask and the solvent removed under reduced pressure. The crude oil was then dissolved in ethyl acetate and poured onto ice cold brine/HCl, washed to pH 4-5 with brine/water, dried over Na2SO4 and the solvent removed under reduced pressure. The residue was dissolved in DCM and adsorbed to RP18 silica gel for RP-flash chromatography via Isco Companion LC (acetonitrile/water/0.1% acetic acid). After removal of AcN/acetic acid under reduced pressure and lyophilisation of the aqueous concentrate, 75 mg (32%) of pure 10 was obtained as pale brown solid.

Figure 8:
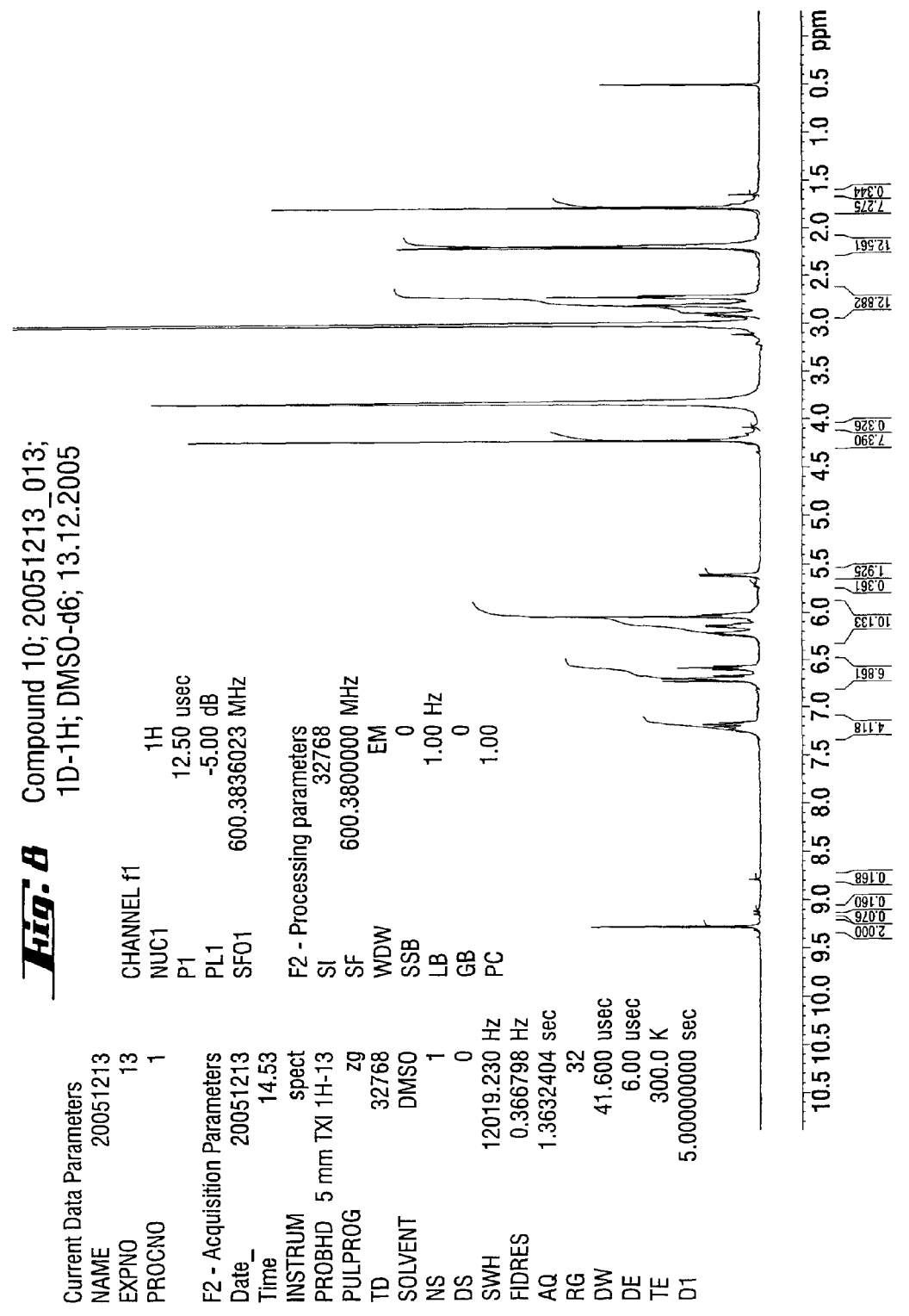

LC-MS: $[M+H]^+$ 975.3
calculated mass: 974
H-NMR: see FIG. 8

Example 9

Disorazole A1 Mono Hemi Succinyl [d-Lys$^6$]LHRH, Both Regio-Isomers (11) & (12)

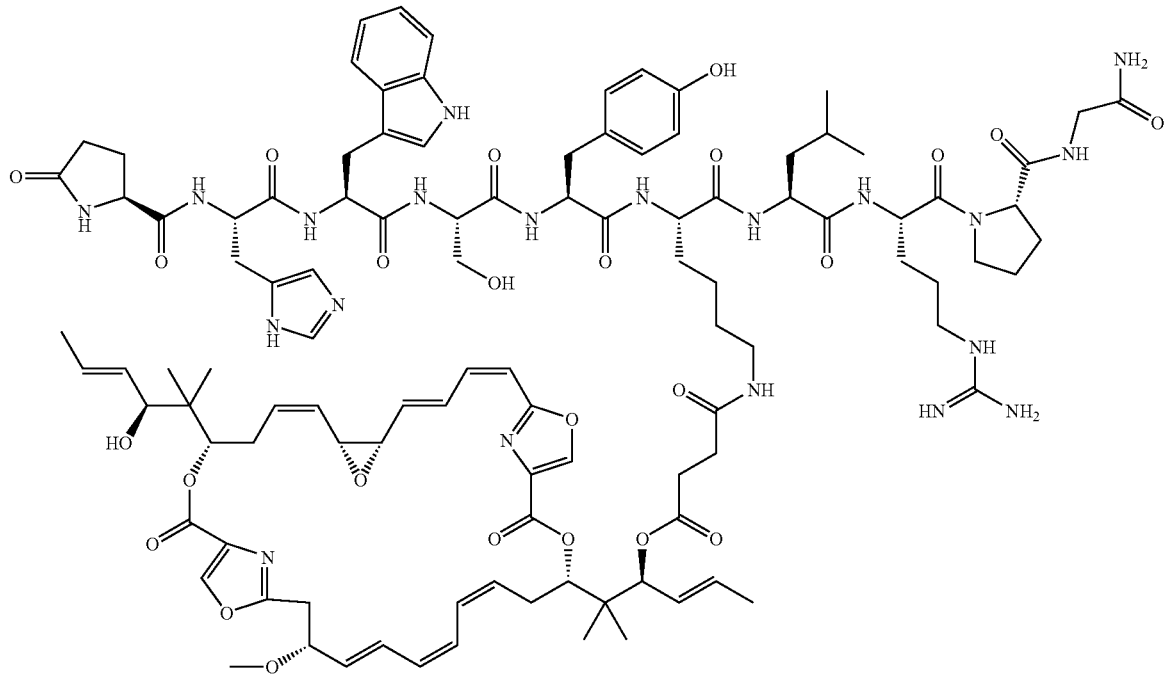

(11)

-continued (12)

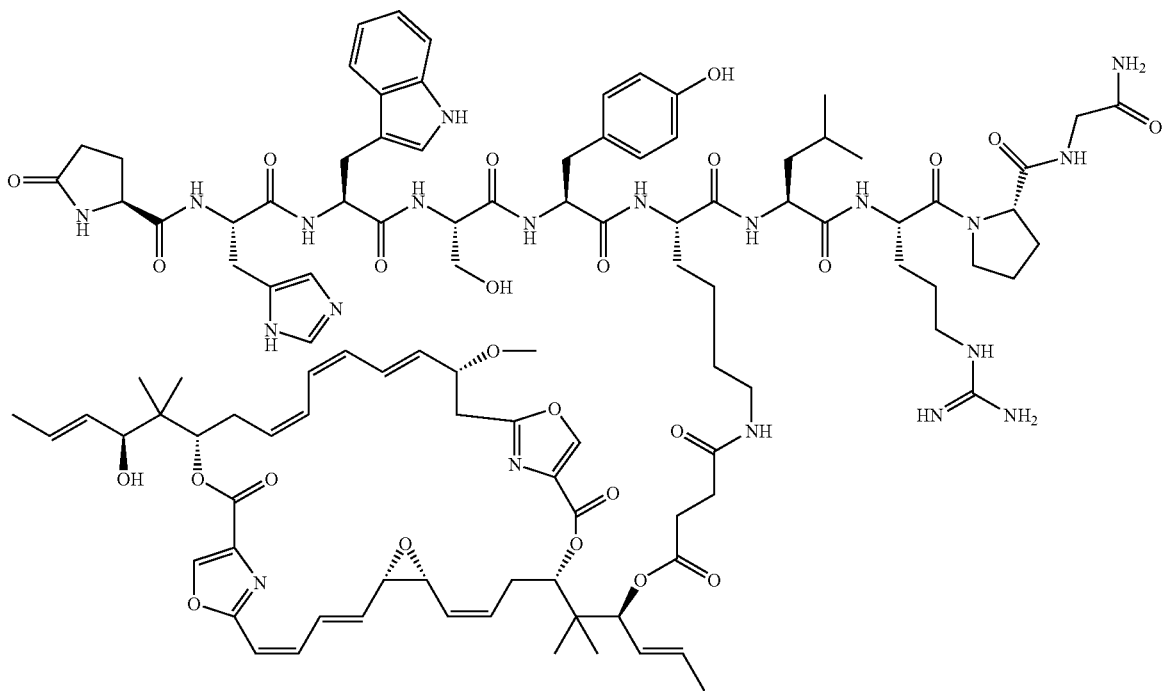

According to the general synthesis procedure listed under B., 6 mg disorazole A1 mono hemi succinate (1:1 mix of both regio isomers) and 3.2 mg HATU were dissolved in 0.25 ml DMF. 5 µl DIPEA was added and stirred for 20 min. at r.t. to allow formation of the activated ester complex. 10.1 mg [D-Lys$^6$]LHRH peptide was dissolved in 0.25 ml DMF, added to the mixture and the reaction stirred for 1.5 h at ambient temperature. The reaction was monitored by HPLC-UV and the mixture subsequently subjected to preparative HPLC. Therefore, the reaction mix was diluted with 1.5 ml of 40% solvent B mixture (A: 20 mM NH$_4$AcO, 5% AcN, 0.2% HOAc pH 4.5; B: 95% AcN, 5% water). The solution was acidified to pH 6 with approx. 0.1 ml 10% HOAc. After filtering through a luer lock membrane filter, the solution was injected into preparative HPLC (40% B→85% B in 25 min). The main peak was collected and the fraction lyophilized to give 5 mg of 11 and 12 as light brown flakes (1:1 ratio, combined yield: 35%).

HR-ESI-MS: (charge state +2) 1048.0 calculated mass: 2092

H-NMR: see FIG. 9

Example 10
Disorazole E1 Mono Hemi Succinyl [D-Lys⁶]LHRH, Both Regio-Isomers (13) & (14)
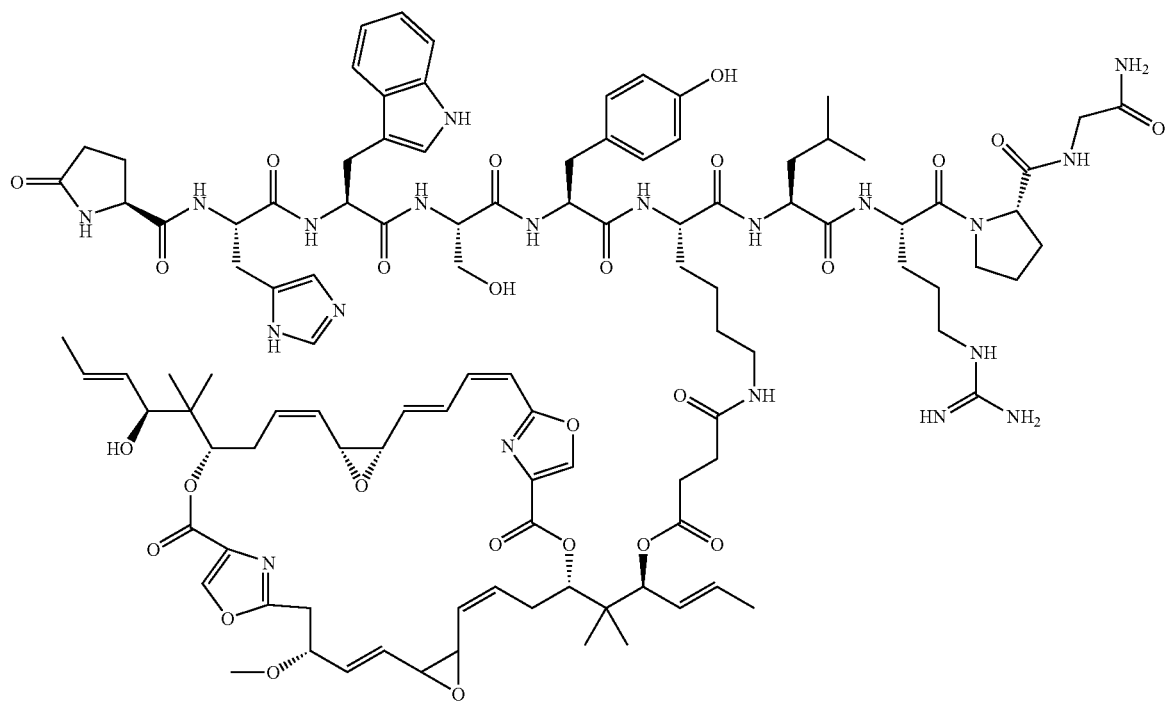
(13)
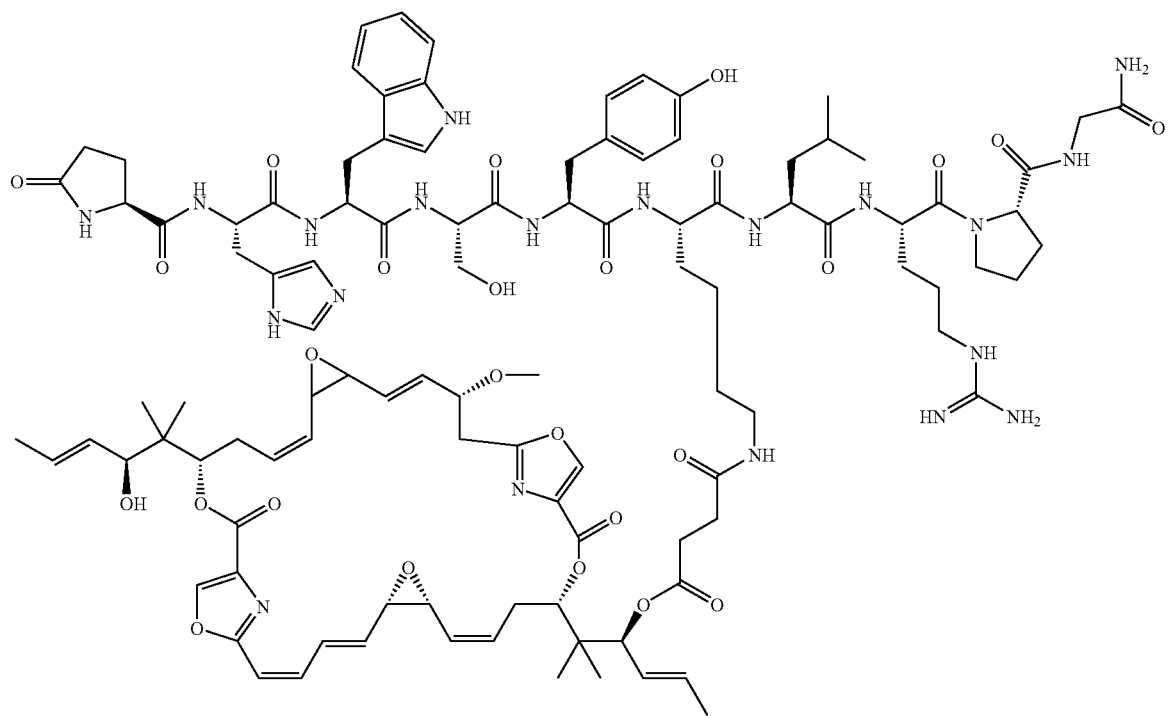
(14)

According to the general synthesis procedure listed under B., 40 mg disorazole E1 mono hemi succinate (1:1 mix of both regio isomers) and 18 mg HATU were dissolved in 1 ml DMF. 25 µl DIPEA was added and stirred for 15 min. at r.t. to allow formation of the activated ester complex. 54 mg [D-Lys⁶]LHRH peptide was dissolved in 1 ml DMF, added to the mixture and the reaction stirred for 2 h at ambient temperature. The reaction was monitored by HPLC-UV and the mixture subsequently subjected to preparative HPLC. Therefore, the reaction mix was diluted with 3.5 ml of 40% solvent B mixture (A: 20 mM NH$_4$AcO, 5% AcN, 0.2% HOAc pH 4.5; B: 95% AcN, 5% water). The solution was acidified to pH 6 with approx. 0.5 ml 10% HOAc. After filtering through a luer lock membrane filter, the solution was injected into preparative HPLC (40% B→85% B in 25 min). The main peak was collected and the fraction lyophilized to give 29 mg of 13 and 14 as light brown flakes (1:1 ratio, combined yield: 36%).

HR-ESI-MS: (charge state +2) 1056.0 calculated mass: 2108

H-NMR: see FIG. 10

Example 11

Disorazole A1 Bis Hemi Succinyl [D-Lys⁶]LHRH
(15)

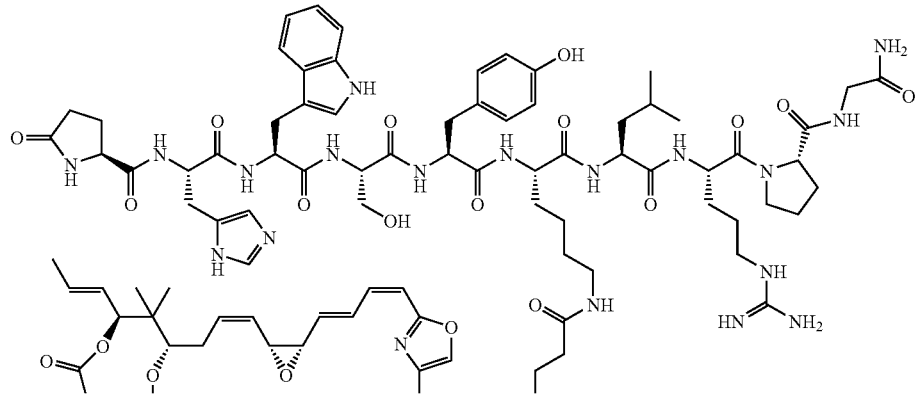

(15)

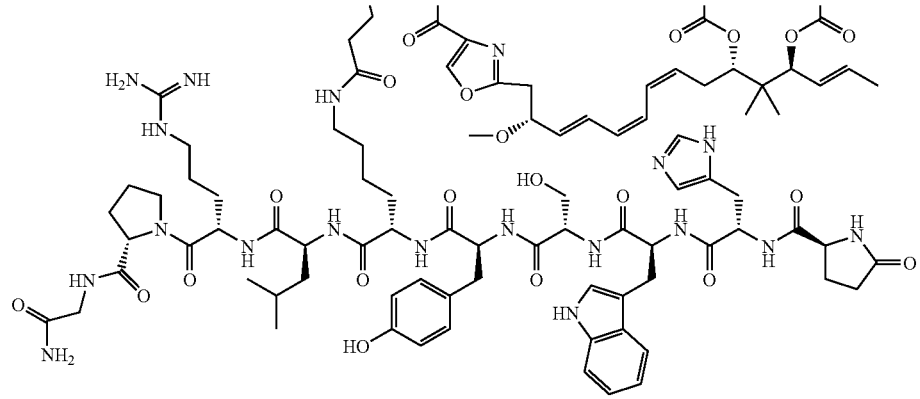

According to the general synthesis procedure listed under B., 15.7 mg disorazole A1 bis hemi succinate and 7.5 mg HATU were dissolved in 1 ml DMF. 11 µl DIPEA was added and stirred for 20 min. at r.t. to allow formation of the activated ester complex. 23.6 mg [D-Lys⁶]LHRH peptide was dissolved in 1 ml DMF, added to the mixture and the reaction stirred for 2 h at ambient temperature. The reaction was monitored by HPLC-UV and the mixture subsequently subjected to preparative HPLC. Therefore, the reaction mix was diluted with 4.5 ml of 40% solvent B mixture (A: 20 mM NH$_4$AcO, 5% AcN, 0.2% HOAc pH 4.5; B: 95% AcN, 5% water). The solution was acidified to pH 6 with approx. 0.5 ml 10% HOAc. After filtering through a luer lock membrane filter, the solution was injected into preparative HPLC (40% B→85% B in 25 min). The main peak was collected and the fraction lyophilized to give 18 mg of 15 as white flakes (yield: 32%).

HR-ESI-MS: (charge state +4) 858.4 calculated mass: 3426

H-NMR: see FIG. 11

Example 12

Disorazole Z Mono Hemi Succinyl [D-Lys⁶]LHRH (16)

(16)

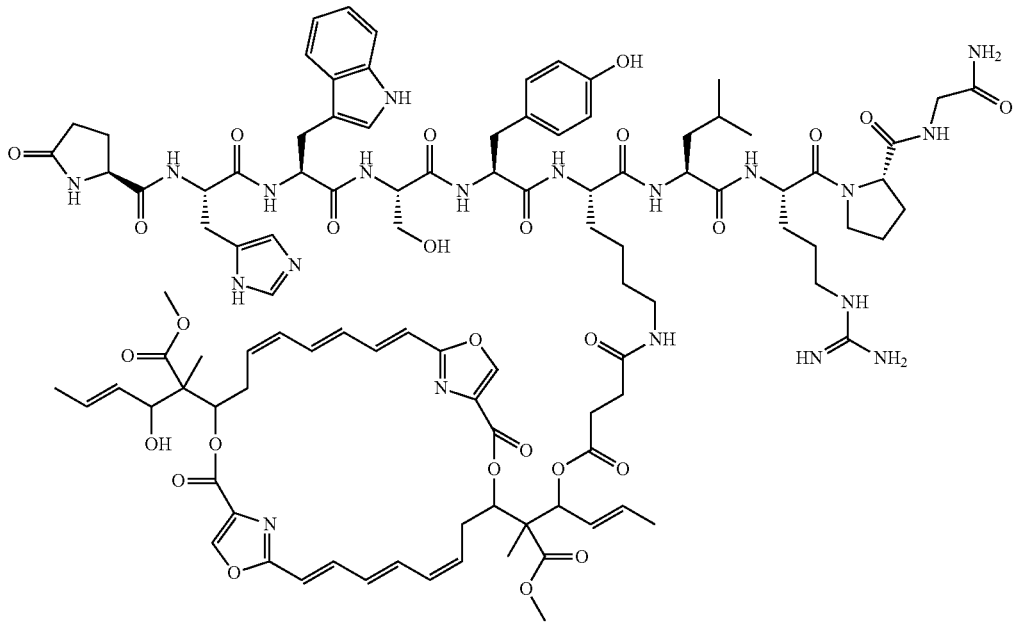

According to the general synthesis procedure listed under B., 45 mg disorazole Z mono hemi succinate and 24 mg HATU were dissolved in 1 ml DMF. 37 μl DIPEA was added and stirred for 20 min. at r.t. to allow formation of the activated ester complex. 76 mg [D-Lys$^6$]LHRH peptide was dissolved in 1 ml DMF, added to the mixture and the reaction stirred for 1.5 h at ambient temperature. The reaction was monitored by HPLC-UV and the mixture subsequently subjected to preparative HPLC. Therefore, the reaction mixture was diluted with 4.5 ml of 40% solvent B mixture (A: 20 mM NH$_4$AcO, 5% AcN, 0.2% HOAc pH 4.5; B: 95% AcN, 5% water). The solution was acidified to pH 6 with approx. 0.75 ml 10% HOAc. After filtering through a luer lock membrane filter, the solution was injected into preparative HPLC (40% B→85% B in 25 min). The main peak was collected and the fraction lyophilized to give 42 mg of 16 as light brown flakes (yield: 38%).

HR-ESI-MS: (charge state +2) 1042.0 calculated mass: 2080

Figure 12:
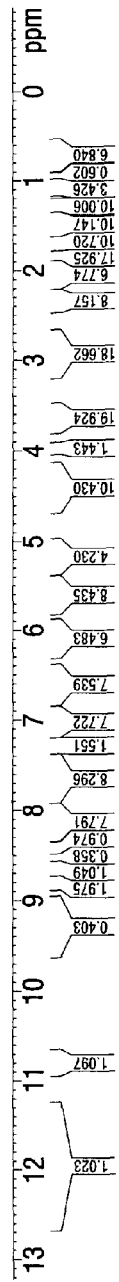

H-NMR: see FIG. 12

Example 13

Disorazole Z Bis Hemi Glutaryl [D-Lys$^6$]LHRH (17)

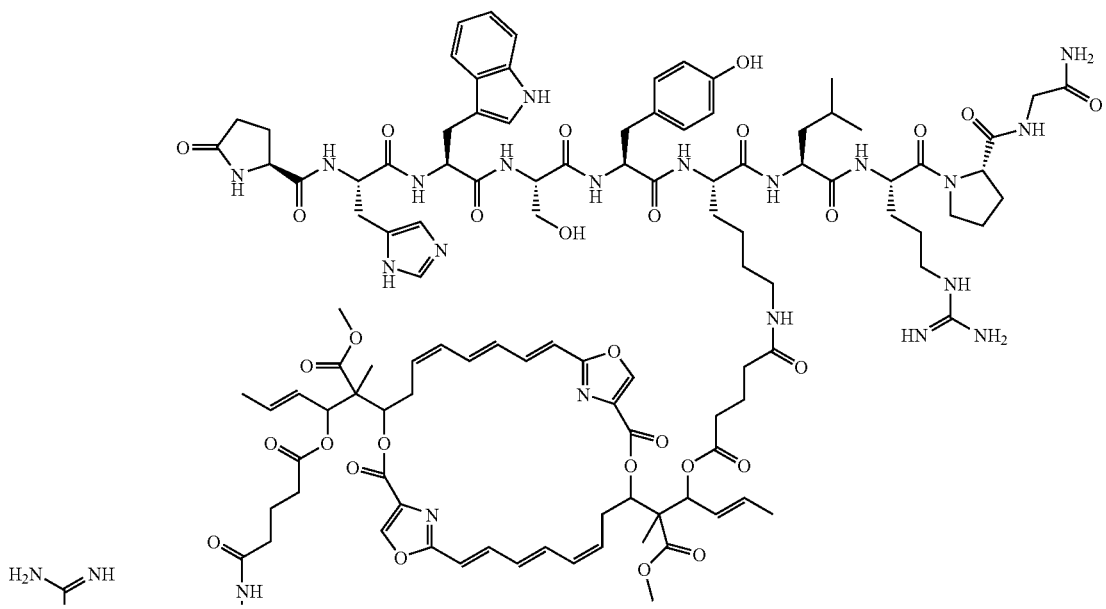

(17)

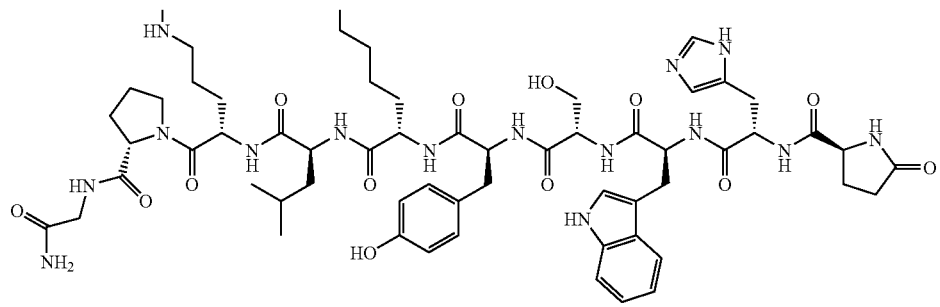

According to the general synthesis procedure listed under B., 35 mg disorazole Z bis hemi glutarate and 34 mg HATU were dissolved in 1 ml DMF. 54 μl DIPEA was added and stirred for 20 min. at r.t. to allow formation of the activated ester complex. 128 mg [D-Lys⁶]LHRH peptide was dissolved in 1 ml DMF, added to the mixture and the reaction stirred for 2 h at ambient temperature. The reaction was monitored by HPLC-UV and the mixture subsequently subjected to preparative HPLC. Therefore, the reaction mix was diluted with 4.5 ml of 40% solvent B mixture (A: 20 mM NH$_4$AcO, 5% AcN, 0.2% HOAc pH 4.5; B: 95% AcN, 5% water). The solution was acidified to pH 6 with approx. 1 ml 10% HOAc. After filtering through a luer lock membrane filter, the solution was injected into preparative HPLC (40% B→85% B in 25 min). The main peak was collected and the fraction lyophilized to give 39 mg of 17 as white flakes (yield: 33%).

HR-ESI-MS: (charge state +4) 862.4 calculated mass: 3442

Figure 13:
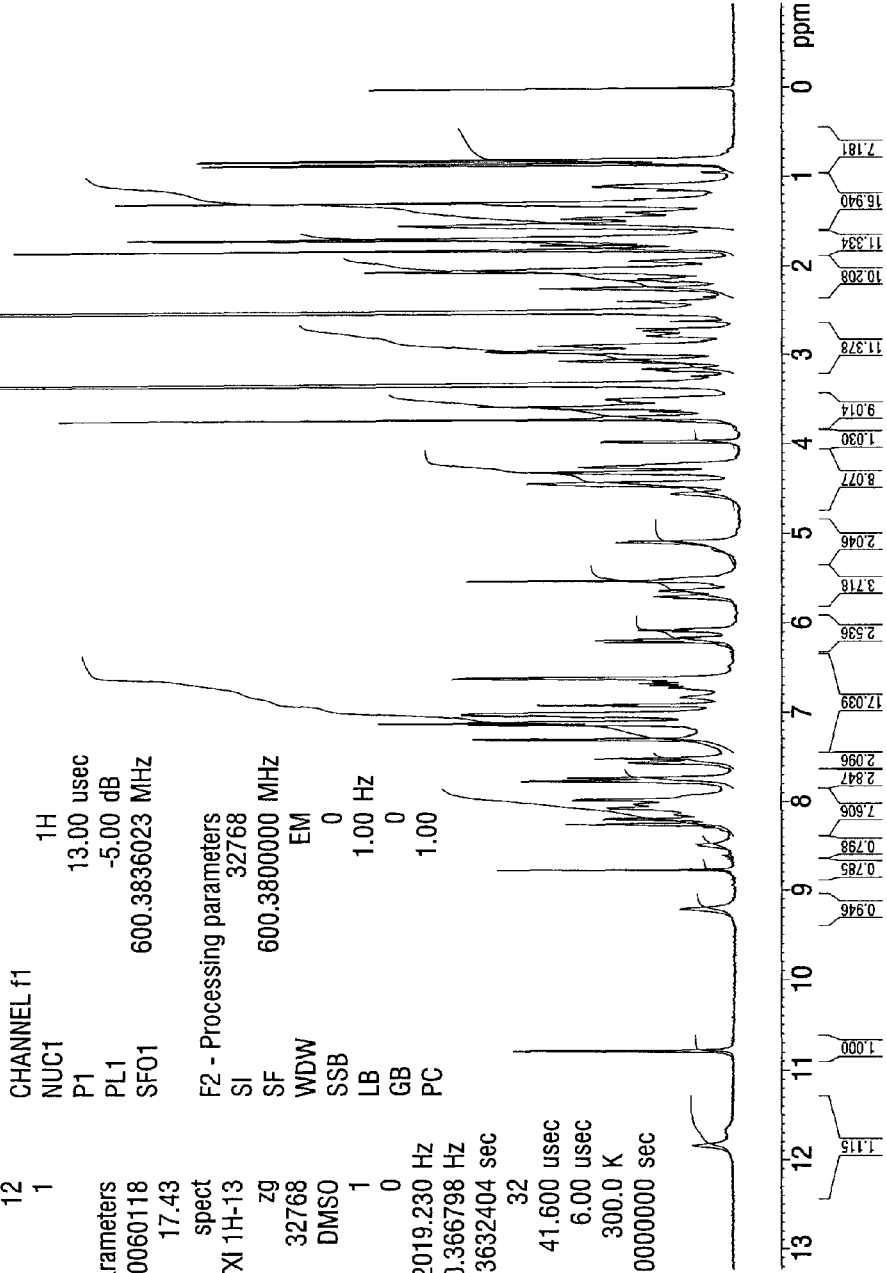

H-NMR: see FIG. 13

Example 14

Disorazole Z Mono Hemi Succinyl Somatostatin (18)

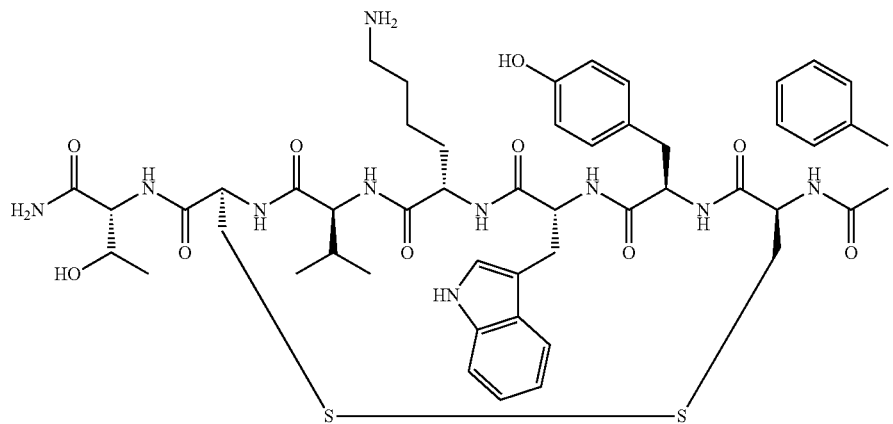

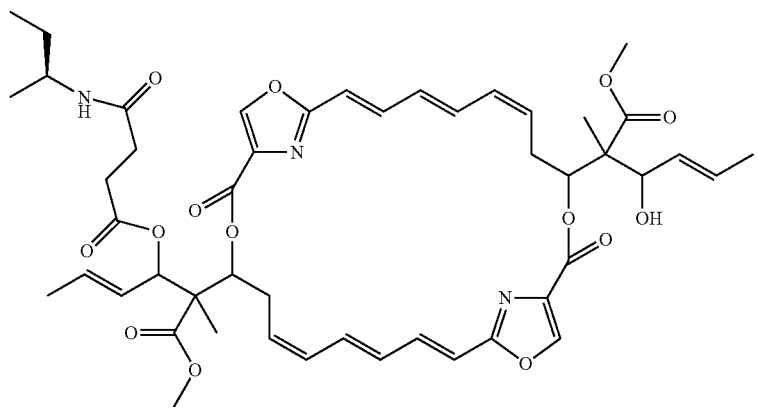

According to the general synthesis procedure listed under B., 20 mg disorazole Z mono hemi succinate and 21 mg HATU were dissolved in 1 ml DMF. 15 µl DIPEA was added and stirred for 15 min. at r.t. to allow formation of the activated ester complex. 25 mg of the synthetic peptide H-D-Phe-Cys-Tyr-D-Trp-Lys(Fmoc)-Val-Cys-Thr-NH$_2$×HCl (disulfide bridged) was dissolved in 1 ml DMF, added to the mixture and the reaction stirred for 4 h at ambient temperature. The reaction was monitored by HPLC-UV. The crude reaction mixture was diluted with 2 ml DMF and piperidine added to a final concentration of 10% (v/v). After stirring for 5 min at r.t., the mixture was directly subjected to preparative HPLC. Therefore, the reaction mix was diluted with 4.5 ml of 50% solvent B mixture (A: 20 mM NH$_4$AcO, 5% AcN, 0.2% HOAc pH 4.5; B: 95% AcN, 5% water). The solution was acidified to pH 6 with approx. 1.5 ml 10% HOAc. After filtering through a luer lock membrane filter, the solution was injected into preparative HPLC (50% B→100% B in 25 min). The main peak was collected and the fraction lyophilized to give 12 mg of 18 as beige flakes (yield: 33%).

HR-ESI-MS: (charge state +2) 937.4
calculated mass: 1873
H-NMR: see FIG. 14

Example 15

Compound 19

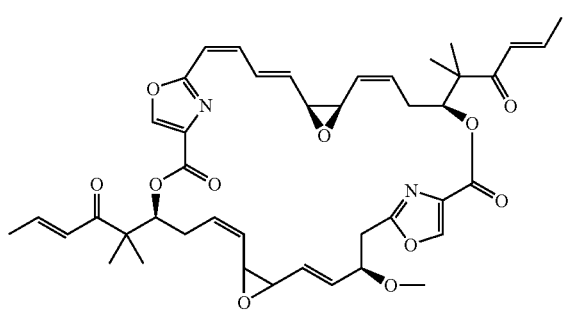 [SMILES: C/C=C/C(=O)C(C)(C)[C@@H]1C/C=C\C2OC2/C=C/[C@H](OC)Cc2nc(co2)C(=O)O[C@H](C(C)(C)C(=O)/C=C/C)C/C=C\[C@H]2O[C@H]2/C=C/C=C\c2nc(co2)C(=O)O1]

According to the general synthesis procedure listed under D., 20 mg of disorazole E1 were oxidized in order to obtain 10 mg diketone product (56%).
LC-MS: [M+H]$^+$: 771.5
calculated mass: 770
H-NMR: see FIG. 15

Example 16

Compound 20

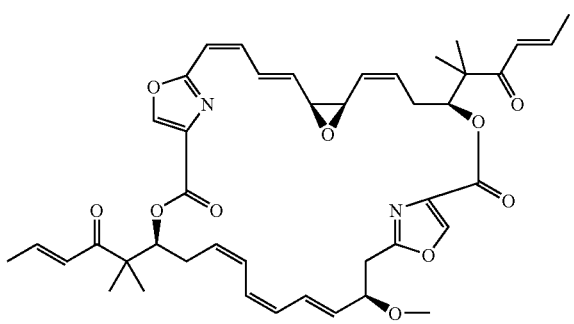 [SMILES: C/C=C/C(=O)C(C)(C)[C@@H]1C\C=C/C=C\C=C\[C@H](OC)Cc2nc(co2)C(=O)O[C@H](C(C)(C)C(=O)/C=C/C)C/C=C\[C@H]2O[C@H]2/C=C/C=C\c2nc(co2)C(=O)O1]

Figure 16:
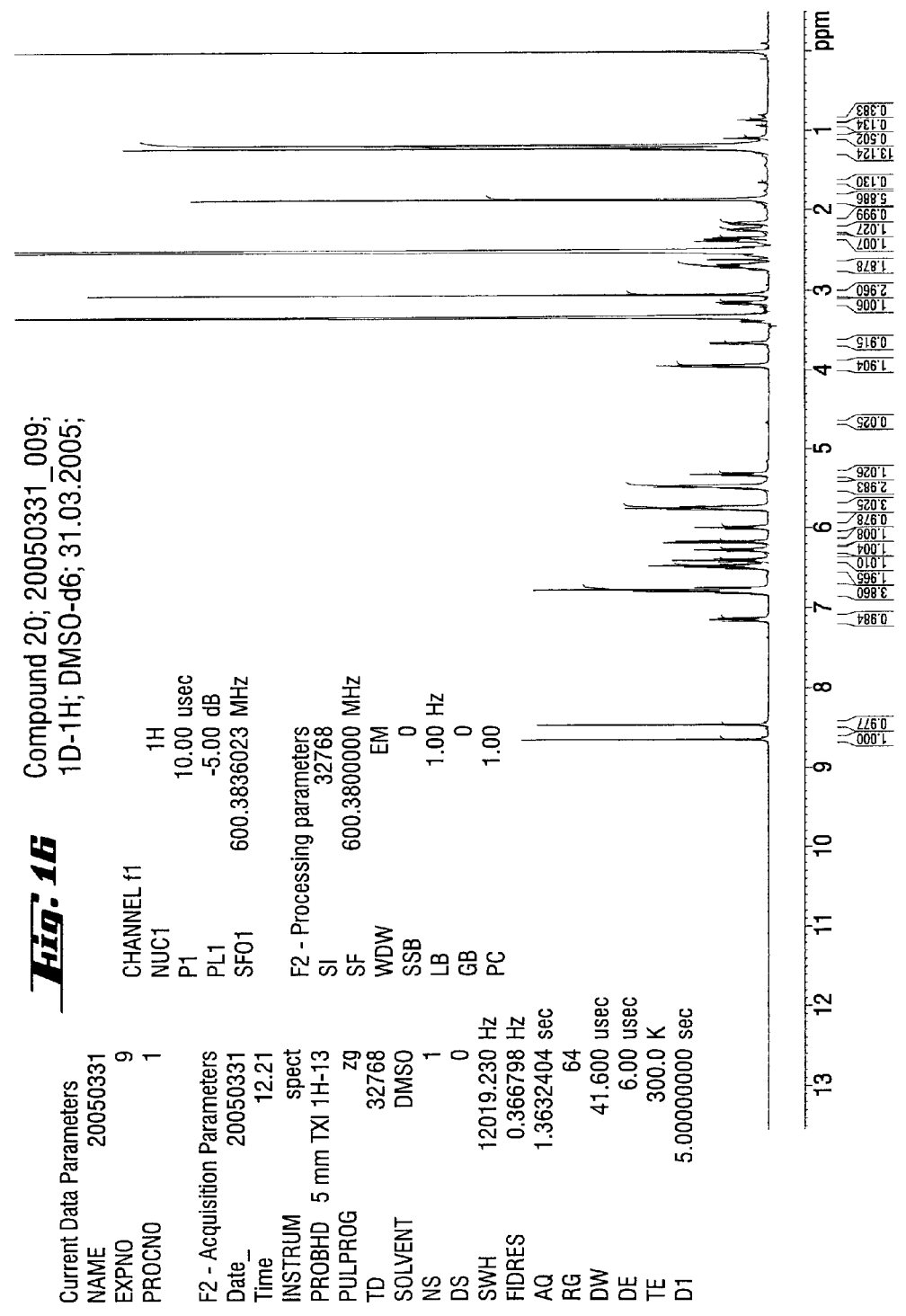

According to the general synthesis procedure listed under D., 25 mg of disorazole A1 were oxidized in order to obtain 17 mg diketone product (67%).
LC-MS: [M+1-1]$^+$: 755.6
calculated mass: 754
H-NMR: see FIG. 16

Example 17

Compound 21

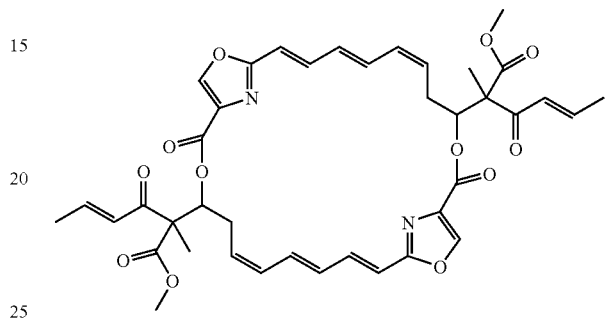

Figure 17:
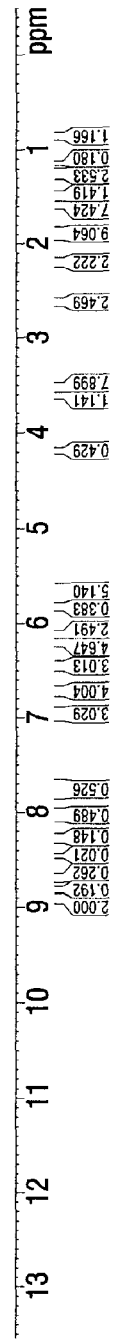

According to the general synthesis procedure listed under D., 44 mg of disorazole Z were oxidized in order to obtain 15 mg diketone product (29%).
LC-MS: [M+H]$^+$: 743.3
calculated mass: 742
H-NMR: see FIG. 17

II) Production of Disorazole Z by Fermentation

Disorazole Z is produced by fermentation of the myxobacteria *Sorangium cellulosum* producer strain Soce 1875 (available at DSMZ under accession No. DSM53600).

For inoculation of the fermenter, a starting culture cultivated in shake flasks is preferred. The fermentation process is carried out for example as batch or fed-batch.

As a starting culture, medium comprising the following components is used: 0.8% soluble starch (Merck 1.01252), 0.2% yeast extract, 0.2% degreased soy meal, 0.1% CaCl$_2$× 2H$_2$O, 0.1% MgSO$_4$×7 H$_2$O, 8 mg/L Na—Fe-EDTA, 1% HEPES buffer, 0.2% glucose, 1% XAD resin at a pH of 7.4 at the start of the cultivation. Starting culture shake flasks can be incubated at 30° C. at an agitation of 160 rpm. For fermentation, a batch fermentation of 70 liters of medium identical to that for the starting culture but without HEPES buffer at a pH of 7.9 before autoclaving is used. 1% (vol/vol) XAD (Amberlite XAD 16, Rohm and Haas) is added to adsorb disorazole Z.

The fermenter is inoculated with one liter starting culture. Cultivation is at a temperature of 30° C., aeration at 5.5 L/min at a stirrer speed of 80 rpm. If necessary, the pH is kept constant at or above 6.8 by addition of 5% KOH solution during the course of the fermentation. Residual starch is controlled by the iodine reaction. The glucose concentration is monitored, e.g. using test stripes (Roche).

The production culture is ready for harvesting when glucose and starch are essentially metabolized and when the concentration of disorazole Z reaches a plateau. After a total of twelve days, the fermentation is stopped and harvested by collecting the XAD resin by sieving. Cells which are attached to the XAD are included in the subsequent extraction and purification steps.

For analytical purposes, an aliquot from the fermentation culture is used for collection of XAD resin and cell mass, followed by extractions using methanol, methanol: ethanol: isopropanol (80:15:5), and a final step using acetone. The extracts are combined, concentrated and analysed by HPLC-MS.

When using an alternative *Sorangium cellulosum* strain, preferably Soce 427 (listed at DSMZ under accession number DSM53419) the following medium can be used for the starting culture: 0.3% starch (Cerestar SF 12618, Cerestar Deutschland, Krefeld), 0.2% degreased soy meal (Soyamine 50T, Lucas Meyer, Hamburg), 0.1% yeast extract (Marcor), 0.1% magnesium sulfate (Roth, PO27.2), 0.05% calcium chloride (Merck, 1.02382), 8 mg/L sodium-iron salt of ethylenediaminetetraacetic acid (Na—Fe-EDTA) (Merck, 108413) and 0.9% HEPES buffer (Roth, 9105.3), at a pH at 7.5. After autoclaving, 20% glucose solution (Riedel-de Haën 16301) is added to a final of 0.3% glucose. For fermentation, the same medium except for HEPES buffer is used at a pH of 7.9 before autoclaving.

Following fermentation according to above description, wet cell mass and XAD resin collected by centrifugation of 70 L fermentation broth of *Sorangium cellulosum*, strain So ce427, are extracted with portions of 3 L of methanol. The combined filtrate is evaporated to give a residual aqueous mixture. If necessary, water is added to give 1.2-1.5 L which are extracted with three portions of 1.2 L dichloromethane. The combined organic solutions are dried with anhydrous sodium sulfate and then evaporated to dryness. The residue is redissolved in 1 L of aqueous methanol (97%) and partitioned with three portions of heptane. The methanol layer is evaporated, diluted with toluene and evaporated to dryness. The residue is separated by gel chromatography with methanol on Sephadex LH-20 (Pharmacia) to give an enriched fraction of disorazole Z, which is purified by RP-MPLC(ODS-AQ, 120 Å, S 16 µm) with methanol-water (65/35) to give purified disorazol Z.

III) Antiproliferative Action on Various Tumor Cell Lines

Selected compounds of the invention were investigated for their antiproliferative activity in a proliferation test on established tumor cell lines.

The test used determines the cellular dehydrogenase activity and makes possible a determination of the cell vitality and indirectly the cell count.

The cell lines used are the human cervical carcinoma cell line KB/HeLa (ATCC CCL17), the ovarian adenocarcinoma cell line SKOV-3 (ATCC HTB77), the human glioblastoma cell line SF-268 (NCI-503138) and the lung carcinoma cell line NCI-H460 (NCI-503473). In addition, for the investigation of the cell cycle-specific action of the compounds of the invention, an RKOp27 cell system was used (Schmidt M et al. Oncogene 2000, 19(20): 2423-2429). RKO is a human colon carcinoma cell line (ATCC CRL-2577), in which the cell cycle inhibitor $p27^{kip1}$ induced by means of the ecdysone expression system is expressed and can be led to a cell cycle arrest specifically in G2. A nonspecifically acting substance inhibits the proliferation independently of whether the RKO cell is or is not arrested in G1 or G2. Cell cycle-specific substances such as, for example, tubulin inhibitors are, however, only cytotoxic if cells are not arrested and the cell cycle is passed through.

XTT Test for Cellular Dehydrogenase Activity

The adherently growing tumor cell lines KB/HeLa, SKOV-3, SF-268 and NCI-H460 were cultured under standard conditions in an incubator at 37° C., 5% $CO_2$ and 95% atmospheric humidity. On experimental day 1, the cells are detached using trypsin/EDTA and pelleted by centrifugation. Subsequently, the cell pellet is resuspended in the respective culture medium at the corresponding cell count and reacted in a 96-well microtiter plate. The plates are then cultured overnight in the incubator. The test substances are prepared as 1 mg/ml stock solutions in DMSO and diluted to the appropriate concentrations on experimental day 2 using culture medium. The substances in culture medium are then added to the cells and incubated in the incubator for 45 h. As a control, cells which are not treated with test substance are used. For the XTT assay, 1 mg/ml of XTT (sodium 3'-[1-(phenylaminocarbonyl)-3,4-tetrazolium]-bis(4-methoxy-6-nitro)benzenesulfonic acid) is dissolved in RPMI-1640 medium without Phenol Red. Additionally, a 0.383 mg/ml PMS (N-methyldibenzopyrazine methylsulfate) solution in phosphate-buffered saline solution (PBS) is prepared. On experimental day 4, 75 µl/well of XTT-PMS mixture is pipetted onto the cell plates which in the meantime have been incubated with the test substances for 45 h. For this, shortly before use, the XTT solution is mixed with the PMS solution in the ratio 50:1 (vol:vol). The cell plates are then incubated in the incubator for a further 3 h and the optical density ($OD_{490\ nm}$) is determined in a photometer. By means of the $OD_{490\ nm}$ determined, the percentage inhibition is calculated relative to the control and plotted semilogarithmically in the form of a concentration-action curve. The $IC_{50}$ is calculated by means of a regression analysis from the concentration-action curve using the program Graphpad Prism.

Cell Cycle Analysis by Means of the RKOp27 Model

The assay is carried out in 96-well plates. By inducible expression of $p27^{kip1}$, the cells are completely arrested in growth, but do not die. By comparison of the activity on induced and noninduced cells, conclusions on the mechanism of action (cell cycle specificity) of the therapeutics can be drawn. Noninduced cells are inoculated in approximately three-fold higher cell count, since division no longer takes place during the assay in comparison with uninduced cells (20000 cells/well induced, 6250 cells/well not induced). The controls are untreated cells (+/−induction). The induction is carried out with 3 µM muristerone A. On the 1st day, the cells are exposed (+/−muristerone A) and incubated at 37° C. for 24 h. On day 2, the test substance is added (control DMSO) and incubation is continued at 37° C. for a further 45 h before a standard XTT assay is carried out.

In table 1, the cytotoxic and/or growth-inhibiting activities of selected compounds of the invention with/without expression of $p27^{kip1}$ are shown in comparison with the cytotoxic moiety doxorubicin, the prior art conjugate AN-152, and disorazole moieties disorazole A1, E1 and Z, and selected compounds of the invention: disorazole Z-(Glutaryl-[D-Lys$^6$]LHRH)$_2$-compound 17; disorazole Z-Succinyl-[D-Lys$^6$]LHRH-compound 16; disorazole E1-Succinyl-[D-Lys$^6$]LHRH-compounds 13/14; disorazole A1-Succinyl-[D-Lys$^6$]LHRH-compounds 11/12; disorazole A1-(Succinyl-[D-Lys$^6$]LHRH)$_2$-compound 15.

The compounds tested showed no cytotoxic activities in the induced state of $p27^{kip1}$. The results show a very potent inhibition of the proliferation of the selected tumor cell lines by the selected compounds of the invention. Furthermore, the tested conjugates show a clear attenuation of toxicity compared to the free, unconjugated disorazole moieties.

TABLE 1

| compound | IC$_{50}$ [μg/ml] | | | | | |
|---|---|---|---|---|---|---|
| | KB/HELA | SKOV-3 | SF-268 | NCI-H460 | RKOp27 | RKOp27 induced |
| doxorubicin | 0.320 | 0.347 | 0.305 | 0.105 | 0.082 | 0.124 |
| AN-152 | 0.871 | 1.238 | 1.258 | 0.558 | 0.587 | 0.632 |
| disorazol Z | 0.001005 | 0.000504 | 0.001284 | 0.000670 | 0.000659 | >3.16 |
| compound 16 | 0.018915 | 0.007683 | 0.017800 | 0.009235 | 0.005180 | >3.16 |
| compound 17 | >3.16 | >3.16 | >3.16 | >3.16 | >3.16 | >3.16 |
| disorazol A1 | 0.000049 | 0.000027 | 0.000125 | 0.000022 | 0.000049 | >3.16 |
| compounds 11/12 | 0.058930 | 0.042800 | 0.113100 | 0.029660 | 0.033960 | >3.16 |
| compound 15 | >3.16 | >3.16 | >3.16 | >3.16 | ca. 3.16 | >3.16 |
| disorazol E1 | 0.000170 | 0.000074 | 0.000474 | 0.000065 | 0.000170 | >3.16 |
| compounds 13/14 | 0.018910 | 0.016850 | 0.055660 | 0.012803 | 0.017240 | >3.16 |

IV) GnRH-Receptor Dependent Proliferation Assay

The dose-dependent receptor-mediated inhibition of cell proliferation of selected compounds of the invention was investigated.

To study these effects a human GnRH receptor (hGnRH-R) positive cell line (5C6; Beckers et al., Eur. J. Biochem. 1995, 231: 535-543) and an hGnRH-R negative cell line (LTK$^-$; ECACC No. 85011432) was used.

Respective cells were exposed to 1 mL culture medium in 24 well multi-titer-plates (MTPs) with a cell number of 15000 cells per well. The cell number is adjusted in such a way that after 5 days of testing the untreated control cells are still in the exponential growth phase.

Test compounds are given to the cultured cells after 4 hours of initial growth (adherence) in a volume of 100 μL to yield the final concentrations given in table 2.

After 30 min of incubation at 37° C. the entire culture medium is sucked off and the cells are washed twice with culture medium without test compounds. After the washing the cells are placed into an incubator (at 37° C., 5% CO$_2$ and 95% atmospheric humidity) and incubated for further 4 days.

For the determination of the cell number after incubation the cells are detached using trypsin/EDTA and centrifuged. The number of vital cells and the total cell number are counted using a Vi-Cell Analyzer (Beckman Coulter).

The number of vital cells is analyzed in comparison with untreated control cells (=100%). Only cell groups (respective wells) are considered of which the total cell viability is more than 90%, i.e. inhibition of cell proliferation by unspecific toxicity can be excluded.

In table 2, the proliferation status after 96 hours of incubation of hGnRH-R positive and negative cells in the presence and absence of different concentrations of test compounds are displayed. The proliferation status of untreated control cells after 96 hours is set to 100%. Test compounds used were prior art conjugate AN-152 and the following selected compounds of the invention: disorazole Z-(Glutaryl-[D-Lys$^6$]LHRH)$_2$-compound 17; disorazole Z-Succinyl-[D-Lys$^6$]LHRH-compound 16; disorazole E1-Succinyl-[D-Lys$^6$]LHRH-compounds 13/14; disorazole A1-Succinyl-[D-Lys$^6$]LHRH-compounds 11/12; disorazole A1-(Succinyl-[D-Lys$^6$]LHRH)$_2$-compound 15.

All tested compounds of the invention show a dose-dependent inhibition of cell proliferation over the investigation period of 96 hours. This inhibition effect is specific as can be seen from the results with the hGnRH-R negative cell line LTK$^-$.

TABLE 2

| | cell line 5C6 | | | | cell line LTK− | | | |
|---|---|---|---|---|---|---|---|---|
| compound | 100 nM | 10 nM | 1 nM | 0.1 nM | 100 nM | 10 nM | 1 nM | 0.1 nM |
| control | 100% | | | | 100% | | | |
| AN-152 | 42.1 | | | | 101.3 | | | |
| compound 17 | 41.7 | 58.5 | 85.9 | 95.5 | 98.0 | 98.8 | 99.8 | 100.9 |
| control | 100% | | | | 100% | | | |
| AN-152 | 43.9 | | | | 102.3 | | | |
| compound 16 | 21.9 | 54.1 | 80.9 | 83.8 | 61.7 | 103.4 | 105.8 | 101.8 |
| control | 100% | | | | 100% | | | |
| AN-152 | 42.1 | | | | 101.3 | | | |
| compounds 13/14 | 14.6 | 45.9 | 80.8 | 85.9 | 27.0 | 93.2 | 98.8 | 98.6 |
| control | 100% | | | | 100% | | | |
| AN-152 | 43.9 | | | | 102.3 | | | |
| compounds 11/12 | 23.5 | 52.5 | 80.3 | 88.0 | 77.2 | 101.4 | 111.5 | 109.6 |
| control | 100% | | | | 100% | | | |
| AN-152 | 43.9 | | | | 102.3 | | | |
| compound 15 | 43.0 | 66.6 | 98.6 | 95.1 | 101.7 | 108.0 | 111.3 | 108.6 |

V) GnRH-Receptor Dependent Anti-Proliferative Action of Compound 16 In Vivo

30 CD 1 nu/nu nude mice were inoculated subcutaneously with the GnRH receptor positive, human ovarian carcinoma cell line OVCAR-3 (5 million cells per animal). The experiment was started after formation of solid tumors. 5 animals per dose group were used.

On day 0 of the experiment, the individual tumor volume was determined by palpation and set to 100%. Test compounds were administered subsequently on day 0 of the experiment by injection into the tail vein of the test animals.

A standard volume of 10 ml of 0.9% saline per kg (200 μl per 20 g mouse) containing the test compound in the required concentration was administered once only on day 0 of the experiment.

The tumor size was determined again by palpation on day 18 of the experiment.

In the case of appearance of additional tumors, the volumes were added.

No toxic effects, like weight loss, were recorded throughout the experiment.

| Group | Control (saline) | Disorazol Z (0.16 mg/kg = 215 nmol/kg) | Compound 16 (0.5 mg/kg = 215 nmol/kg) | Compound 16 (0.1 mg/kg = 43 nmol/kg) |
|---|---|---|---|---|
| Average tumor size day 0 | 86 | 92 | 74 | 79 |
| Standard deviation day 0 | 15 | 34 | 59 | 21 |
| Average tumor size day 18 | 206 | 146 | 40 | 76 |
| Standard deviation day 18 | 165 | 97 | 26 | 64 |

The results demonstrate the growth of the untreated tumors, the moderate suppression of tumor growth by disorazol Z alone, and the dose dependent, clearly improved antiproliferative efficacy obtained by conjugation of disorazol Z to [D-Lys$^6$]-LHRH.

The above written description of the invention provides a manner and process of making and using it such that any person skilled in this art is enabled to make and use the same, this enablement being provided in particular for the subject matter of the appended claims, which make up a part of the original description and including a compound of the formula (I) or (IV):

$$C1-B1-A-B2-C2 \quad (I)$$

$$C1-B1-A \quad (IV),$$

wherein for (I) and (IV):

A is a disorazole moiety according to formula (II)

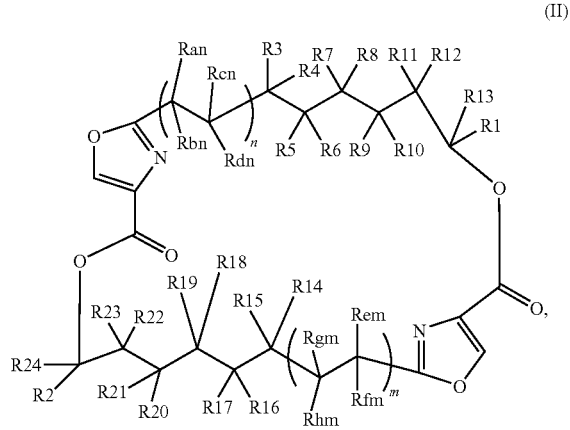

(II)

wherein:

Ra$_n$, Rb$_n$, Rc$_n$, Rd$_n$, Re$_m$, Rf$_m$, Rg$_m$, Rh$_m$, R1, R2, R3, R4, R5, R6, R7, R8, R9, R10, R11, R12, R13, R14, R15, R16, R17, R18, R19, R20, R21, R22, R23, R24 are independently from each other selected from the group consisting of hydrogen, alkyl, cycloalkyl, cycloalkyl-alkyl, aryl, heteroaryl, aryl-alkyl, heteroaryl-alkyl, heterocyclyl, heterocyclyl-alkyl, alkylsulfonyl, arylsulfonyl, aryl-alkylsulfonyl, halogen, hydroxyl, carbonyl, acetyl, carboxyl, carboxylester, amide, carbonate, carbamate, alpha-amino acid residues, beta-amino acid residues, alkoxyl, amino, imino, hydroxylamino, mono-alkylamino, di-alkylamino, hydrazinyl, cyano, alkyl-cyano, sulfhydryl, disulfidylalkyl and/or alkyl-sulfidyl which are optionally substituted in the alkyl, cycloalkyl, cycloalkyl-alkyl, aryl, heteroaryl, aryl-alkyl, heteroaryl-alkyl, heterocyclyl, heterocyclyl-alkyl, alkylsulfonyl, arylsulfonyl, aryl-alkylsulfonyl, carbonyl, acetyl, carboxyl, carboxylester, amide, carbonate, carbamate, alkoxyl, mono-alkylamino, di-alkylamino, alkyl-cyano, disulfidylalkyl and/or alkyl-sulfidyl group by 1, 2 or 3 substituents independently from each other selected from the group consisting of alkyl, cycloalkyl, cycloalkyl-alkyl, aryl, heteroaryl, arylalkyl, heteroaryl-alkyl, heterocyclyl, heterocyclyl-alkyl, alkylsulfonyl, arylsulfonyl, aryl-alkylsulfonyl, halogen, —F, —Cl, —Br, —I, —N$_3$, —NO$_2$, =O, =S, =S(O)$_2$, hydroxyl, carbonyl, acetyl, carboxyl, carboxylester, —C(O)OH, —C(O)NH$_2$, amide, carbonate, carbamate, alpha-amino acid residues, beta-amino acid residues, alkoxyl, amino, imino, hydroxylamino, mono-alkylamino, di-alkylamino, hydrazinyl, cyano, alkyl-cyano, sulfhydryl, disulfidylalkyl and/or alkyl-sulfidyl;

optionally, any two adjacent radicals R of radicals Ra$_n$, Rb$_n$, Rd$_n$, Rd$_n$, Re$_m$, Rf$_m$, Rg$_m$, Rh$_m$, R1, R2, R3, R4, R5, R6, R7, R8, R9, R10, R11, R12, R13, R14, R15, R16, R17, R18, R19, R20, R21, R22, R23, R24 can form an atomic bond to yield a double bond or can form an epoxide (oxiran), aziran (aziridine), alkyl-, cycloalkyl-, cycloalkyl-alkyl-, heteroaryl-, arylalkyl-, heteroaryl-alkyl-, heterocyclyl- and/or heterocyclyl-alkyl-substituted aziran (aziridine), thiirane and/or thiirane-S-oxide group;

B1, B2 are independently from each other a linker, that covalently links A with C1 and/or C2;

C1, C2 are independently from each other a cell-binding molecule selected from the group consisting of peptide, peptide hormone, protein, protein hormone, receptor ligand, blood plasma protein, serum protein, antibody, and antibody fragment;

n is 0, 1, 2, 3;

m is 0, 1, 2, 3.

Also included are pharmaceutical compositions of such compounds, e.g., with excipients, carriers, etc., especially where the at least one compound is present in a unit dose of from 0.0001 mg to 100 mg per kg of a patient's bodyweight and optionally including at least one additional pharmacologically active substance for example selected from the group consisting of: DNA topoisomerase I and/or II inhibitors, DNA intercalators, alkylating agents, microtubule destabilisators, hormone- and/or growth-factor-receptor-agonists and/or -antagonists, inhibitors of signal transduction, antibodies against growth factors and their receptors, kinase inhibitors, anti-metabolites, actinomycin D, aminoglutethimide, asparaginase, avastin, azathioprin, BCNU (carmustine), bleomycin, busulfan, carboplatin, CCNU (lomustine), chlorambucil, cisplatin, colaspase, cyclophosphamide, cytarabin, dactinomycin, daunorubicin, diethylstilbestrole, docetaxel, doxorubicin (adriamycin), DTIC (dacarbacin), epirubicin, epothilone, erbitux, erythrohydroxynonyladenine, ethinylestradiole, etoposide, fludarabine phosphate, fluoxymesterone, flutamide, gemcitabine, gleevec/glivec, herceptin, hexamethylrmelamine, hydroxurea, hydroxyprogesterone caproate, idarubicin, ifosfamide, interferone, iressa, irinotecan, L-asparaginase, leucovorine, mechlorethamine, medroxyprogesterone acetate, megestrole acetate, melphalan, mesna, methotrexate, mitomycin C, mitotan, mitoxantrone, N-phosphonoacetyle-L-aspartate (PALA), oxaliplatin, paclitaxel, pentostatine, plicamycin, prednisolone, prednisone, procarbazine, raloxifen, rapamycin, semustin, sorafenib, streptozocin, tamoxifen, tarceva, taxotere, teniposide, testosterone propionate, thioguanine, thiotepa, topotecan, trimethylemelamine, uridine, vinblastine, vincristin, vindesine, vinorelbin, 2',2'-difluorodeoxycytidine, 5-fluorodeoxyuridine monophosphate, 5-azacytidine cladribine, 5-fluorodeoxyuridine, 5-fluorouracile (5-FU), 6-mercaptopurine.

Also included is the treatment and/or prophylaxis of acute leukemia, adenocarcinoma, basalioma, benign tumors, bladder cancer, bowel cancer, brain tumors, breast cancer, bronchial carcinoma, carcinoids, carcinomas, cervical cancer, cervical carcinoma, chronic leukemia, colon cancer, colon carcinoma, colorectal cancer, connective tissue cancer, corpus carcinoma, endometrial cancer, esophageal cancer, Ewing-Sarcoma, gastrinoma, glioblastoma, glioma, gynaecological tumors, head and/or neck cancer, hepatoblastoma, hepatoma, hyperplasia, hyperproliferative diseases, intraocular melanoma, Kaposi-Sarcoma, laryngeal carcinoma, larynx cancer, leimoyoma, leukemia, liver tumor, lung cancer, non-small cell lung cancer, lymphoma, malign tumors, mamma carcinoma, medulloblastoma, melanoma, multiple myeloma, nephroblastoma, neuroblastoma, neuroendocrine tumors, osteosarcoma, ovarian cancer, pancreas tumor, prostate cancer, prostate carcinoma, rectal carcinoma, renal cancer, renal cell carcinoma, retinoblastoma, rhabdoid tumor, sarcomas, skin cancer, soft part sarcoma, solid tumors, spinalioma, stomach cancer, testicular cancer, thymoma, thyroid gland cancer, tumors starting from the brain and/or nervous system and/or meninges, urinary cancer and/or uterus cancer.

Administration can be at any time, for example before and/or during and/or after radiation therapy treatment and/or surgery.

Also included is a kit comprising a pharmacologically active amount of at least one compound as described herein and a pharmacologically active amount of at least one additional pharmaceutically active substance.

As used herein, the phrases selected from the group consisting of, chosen from, and the like include mixtures of the specified materials. Terms such as contain(s) and the like as used herein are open terms meaning 'including at least' unless otherwise specifically noted. Phrases such as mention may be made, etc. preface examples of materials that can be used and do not limit the invention to the specific materials, etc., listed.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The invention claimed is:

1. A method for the treatment of ovarian, endometrial, cervical, uterine, prostate, bladder, liver, stomach, pancreatic, breast, colon, brain, lung or skin cancer, multiple myeloma, lymphoma or leukemia, comprising administering to a patient in need thereof a compound of the formula (I) or (IV):

C1-B1-A-B2-C2      (I)

C1-B1-A      (IV), wherein A is a disorazole moiety according to formula (III)

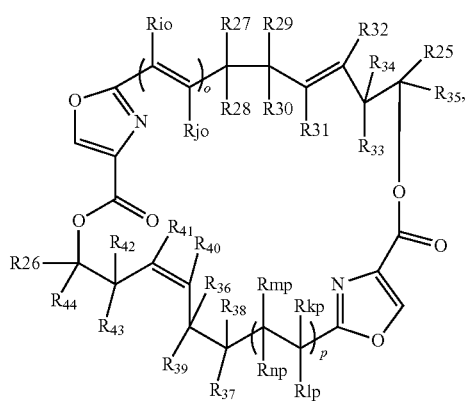

(III)

wherein $Ri_o$, $Rj_o$, $Rk_p$, $Rm_p$, R28, R30, R31, R32 R33, R34, R35, R36, R38, R40, R41, R42, R43, and R44 are hydrogen;
$R1_p$ and $Rn_p$ together form a double bond or are independently selected from the group consisting of hydrogen and alkoxyl;
R27 and R29 together form a double bond or an epoxide;
R37 and R39 together form a double bond or an epoxide;
R25 and R26 are independently from each other selected from the group consisting of: alkyl which is optionally substituted in the alkyl group by 1, 2 or 3 substituents independently from each other selected from the group consisting of alkyl, cycloalkyl, cycloalkyl-alkyl, aryl, heteroaryl, aryl-alkyl, heteroaryl-alkyl, heterocyclyl, heterocyclyl-alkyl, alkylsulfonyl, arylsulfonyl, aryl-alkylsulfonyl, halogen, —F, —Cl, —Br, —I, —N$_3$, =O, =S, =S(O)$_2$, hydroxyl, carbonyl, acetyl, carboxyl, carboxylester, amide, carbonate, carbamate, alpha-amino acid residues, beta-amino acid residues, alkoxyl, amino, imino, hydroxylamino, mono-alkylamino, di-alkylamino, hydrazinyl, cyano, alkyl-cyano, sulfhydryl, disulfidylalkyl and alkyl-sulfidyl;
B1 and B2 are independently from each other selected from the group consisting of dicarbonic acid residue linker, succinyl and glutaryl;
C1 and C2 are independently from each other selected from the group consisting of LHRH, [D-Lys$^6$]-LHRH, somatostatin, and a somatostatin analogue;
o is 1 or 2; and
p is 1 or 2.

2. The method according to claim 1, wherein the compound is selected from the group consisting of:
disorazole A1—succinyl-[D-Lys$^6$]LHRH (regioisomeric compounds 11 and 12):

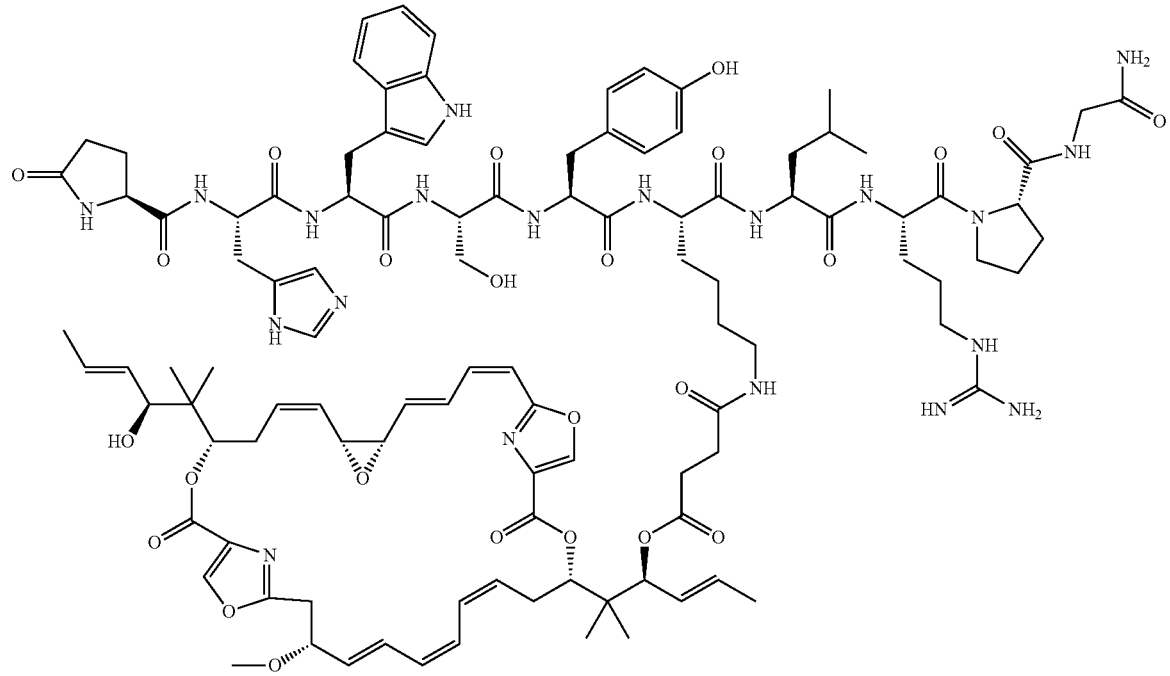

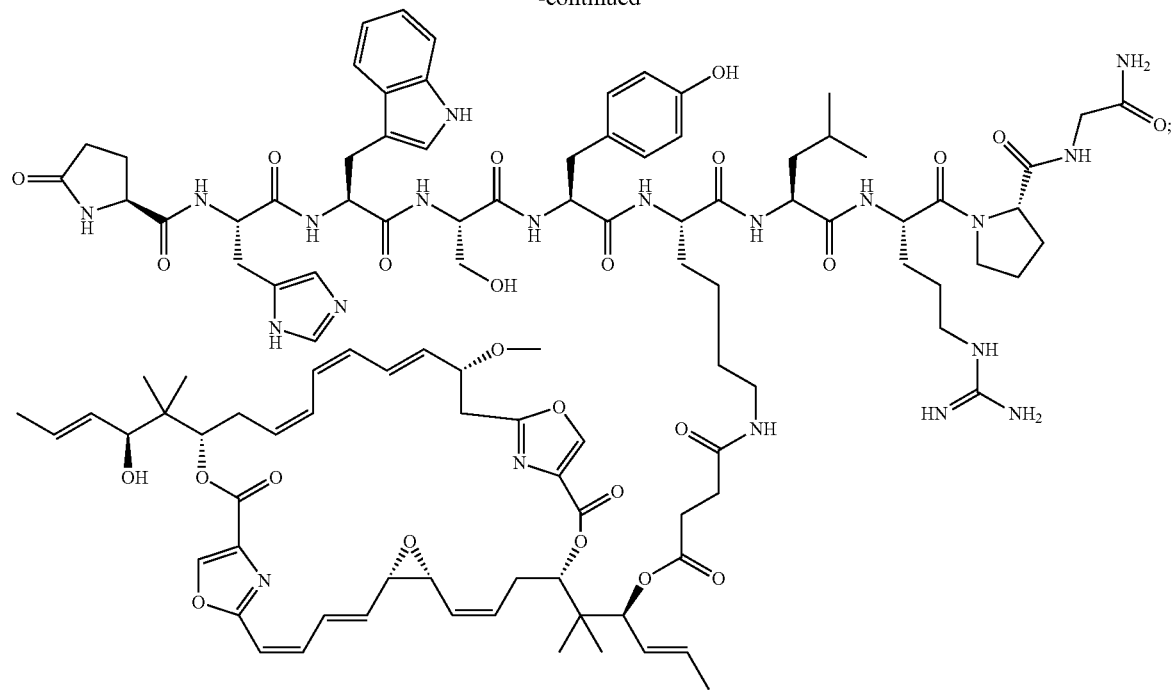
disorazole E1—succinyl-[D-Lys⁶]LHRH (regioisomeric compounds 13 and 14):
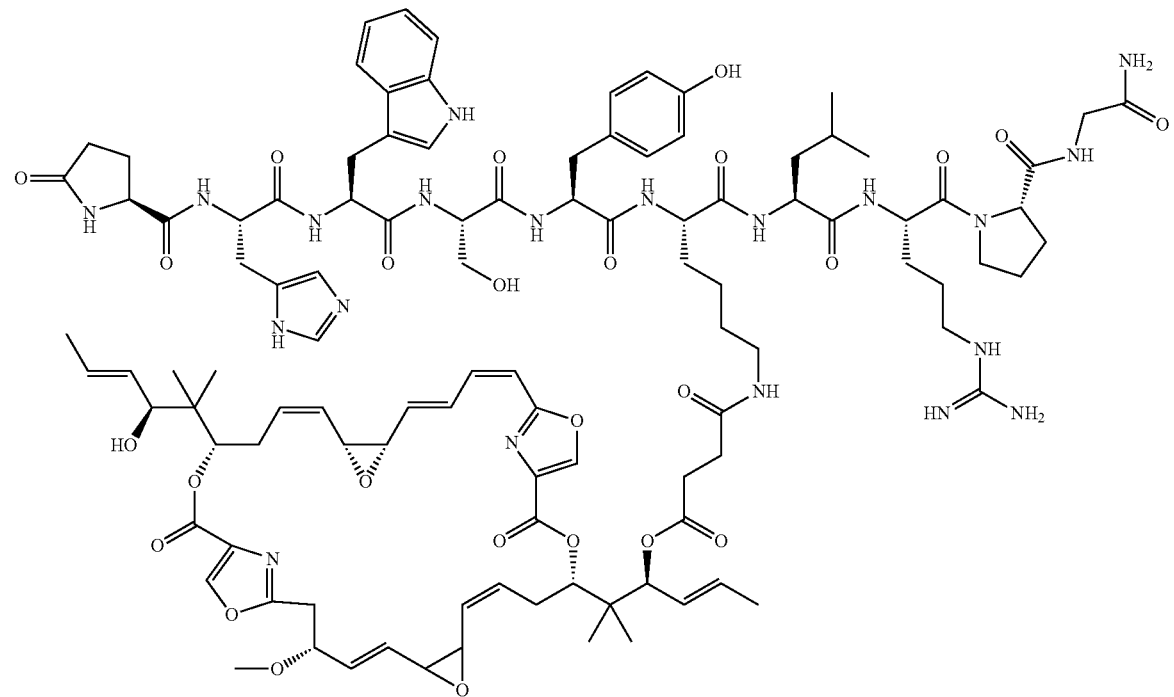

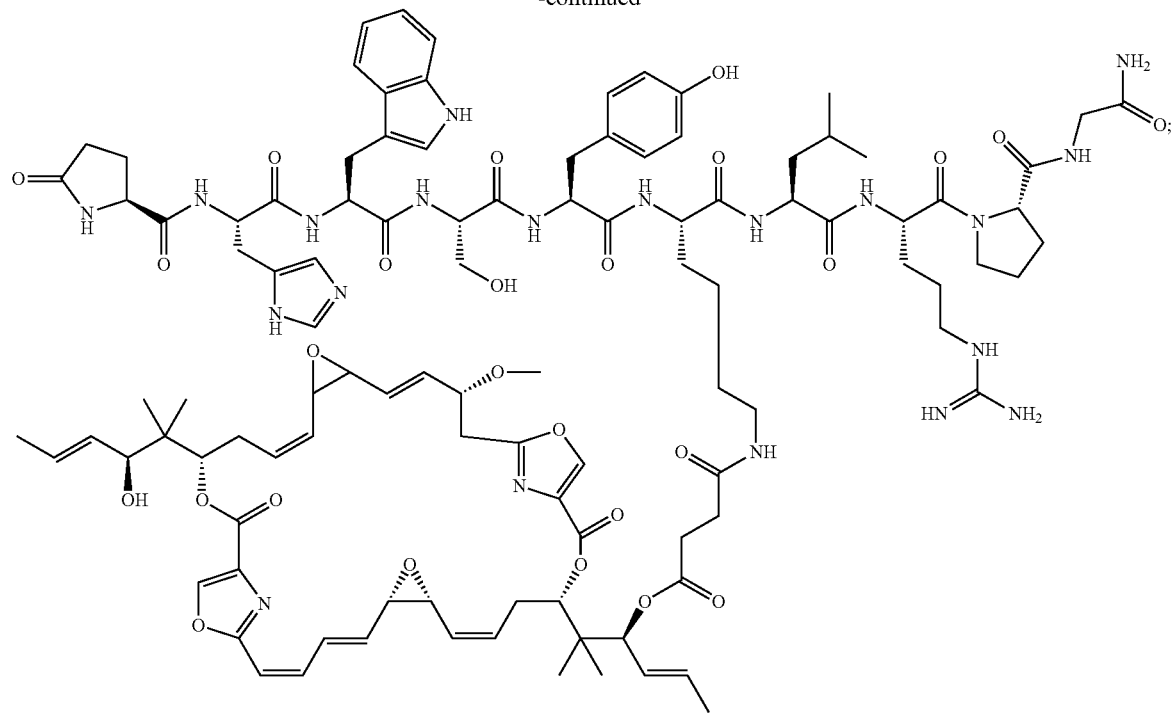
disorazole A1—(succinyl-[D-Lys⁶]LHRH)₂ (compound 15):
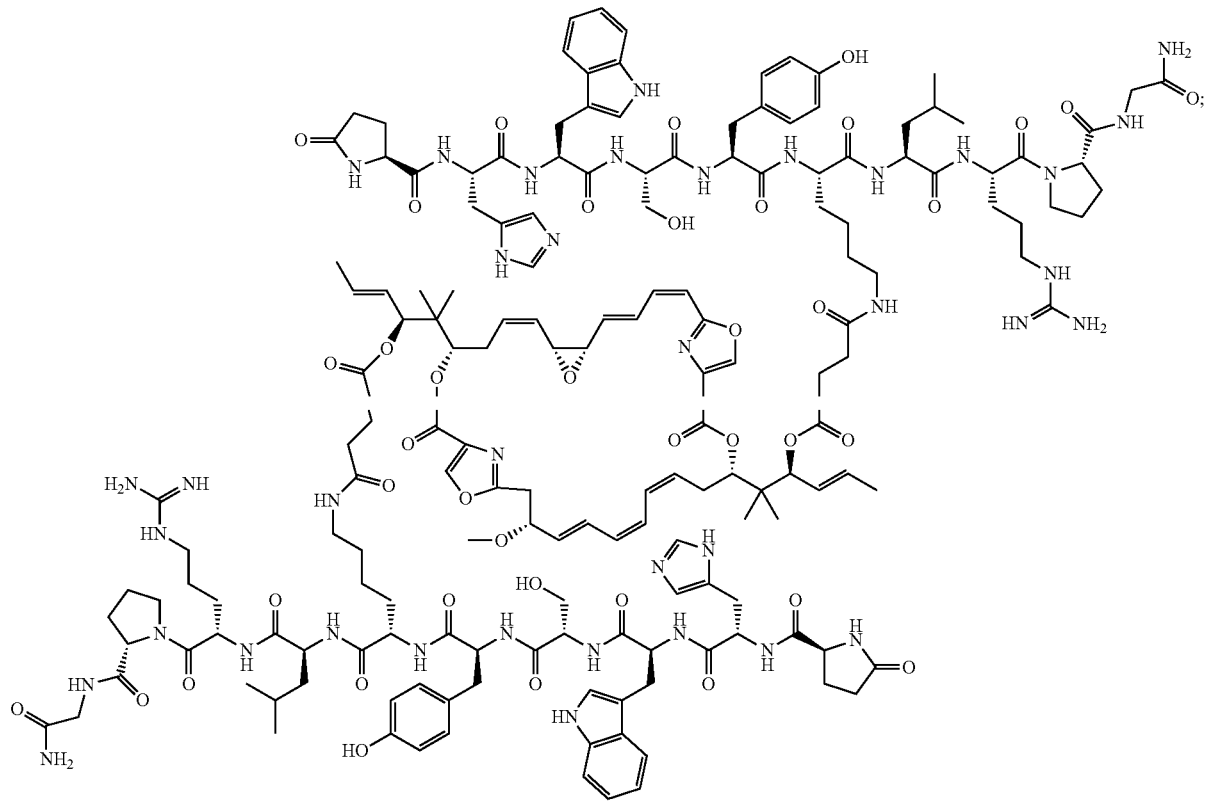

disorazole Z—succinyl[D-Lys⁶]LHRH (compound 16):
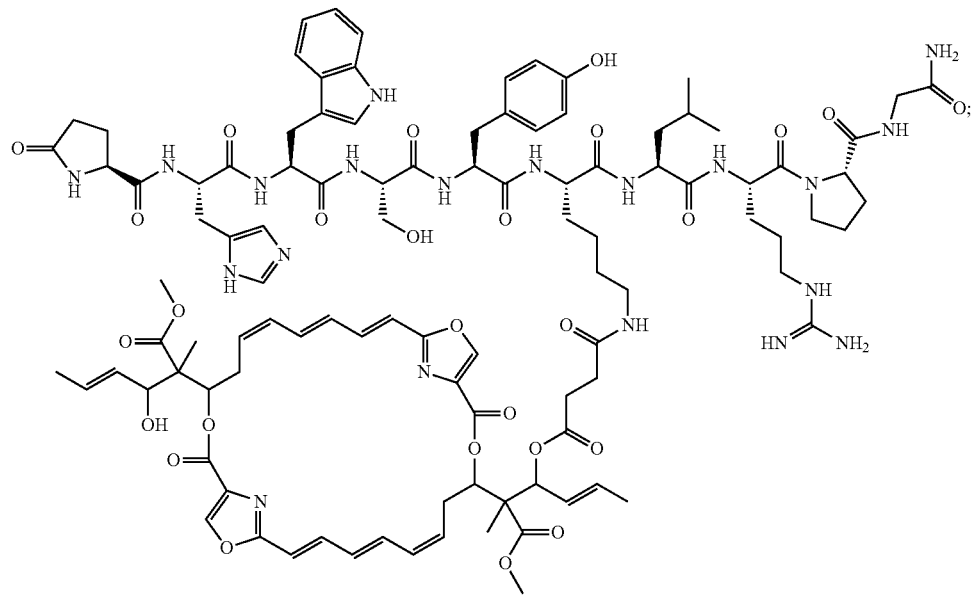 [SMILES: C/C=C/C(O)C(C)(C(=O)OC)C1C\C=C/C=C/C=C/c2nc(co2)C(=O)OC(C(C)(C(=O)OC)C(/C=C/C)OC(=O)CCC(=O)NCCCC[C@H](NC(=O)[C@H](Cc2ccc(O)cc2)NC(=O)[C@H](CO)NC(=O)[C@H](Cc2c[nH]c3ccccc23)NC(=O)[C@H](Cc2cnc[nH]2)NC(=O)[C@@H]2CCC(=O)N2)C(=O)N[C@@H](CC(C)C)C(=O)N[C@@H](CCCNC(=N)N)C(=O)N2CCC[C@H]2C(=O)NCC(N)=O)C\C=C/C=C/C=C/c2nc(co2)C(=O)O1]
disorazole Z—(glutaryl-[D-Lys⁶]LHRH)₂ (compound 17):
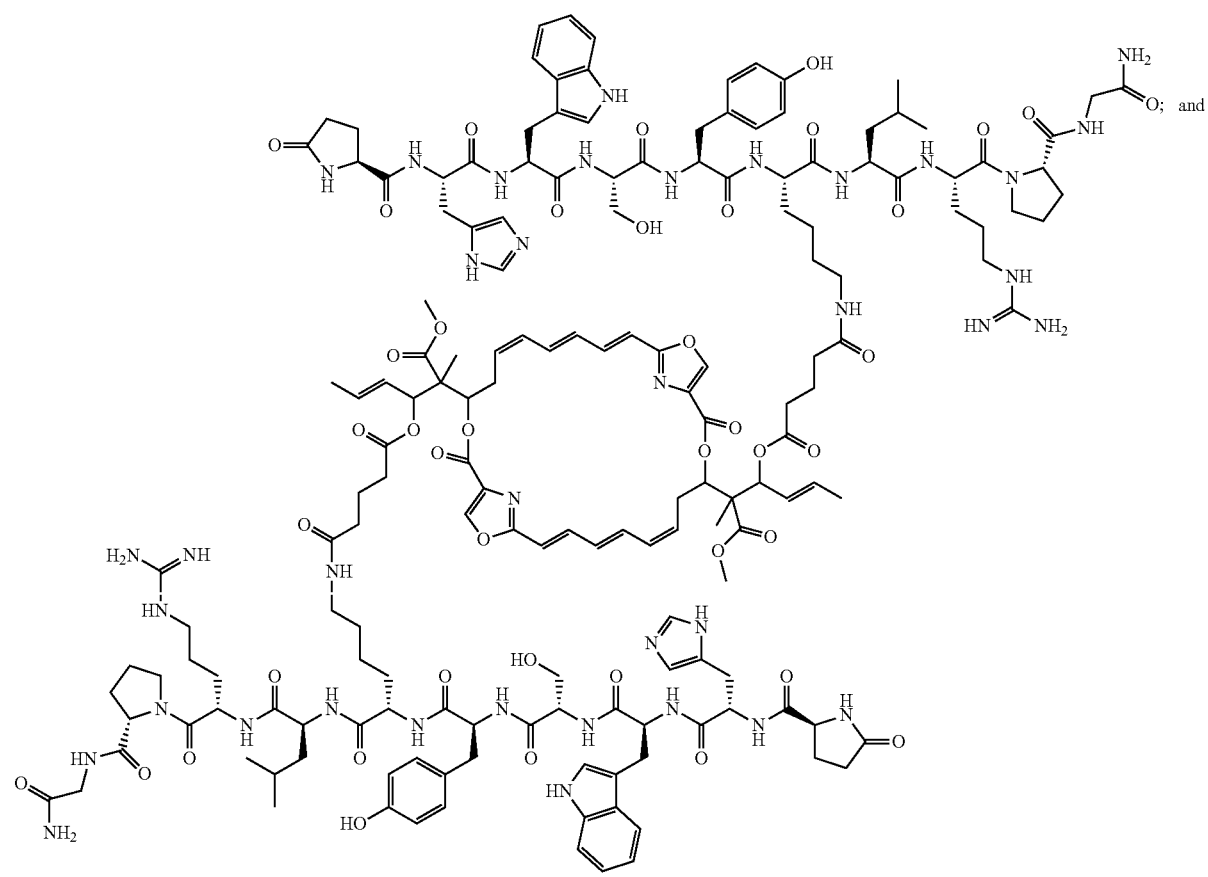
and disorazole Z—succinyl-somatostatin (compound 18):

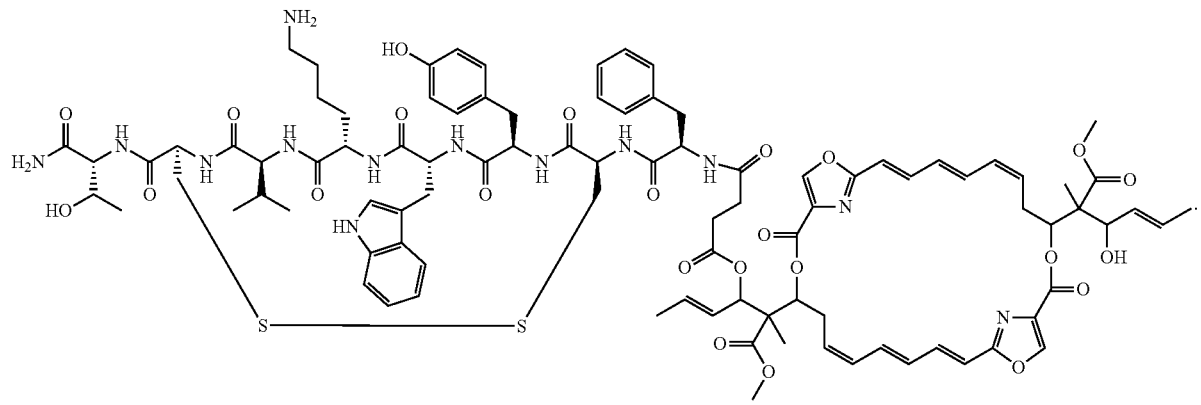 [SMILES: C/C=C/C(O)C(C)(C(=O)OC)C1C\C=C/C=C/C=C/c2nc(co2)C(=O)OC(C(C)(C(=O)OC)C(/C=C/C)OC(=O)CCC(=O)N[C@H](Cc2ccccc2)C(=O)N[C@H]2CSSC[C@@H](C(=O)N[C@@H](C(N)=O)C(C)O)NC(=O)[C@H](C(C)C)NC(=O)[C@H](CCCCN)NC(=O)[C@@H](Cc3c[nH]c4ccccc34)NC(=O)[C@@H](Cc3ccc(O)cc3)NC2=O)C\C=C/C=C/C=C/c2nc(co2)C(=O)O1 ; "."]

3. The method of claim 1, which is for treating cervical carcinoma.

4. The method of claim 1, which is for treating ovarian cancer, wherein said ovarian cancer is ovarian adenocarcinoma.

5. The method of claim 1, which is for treating brain cancer, wherein said brain cancer is glioblastoma.

6. The method of claim 1, which is for treating lung cancer, wherein said lung cancer is lung carcinoma.

7. The method of claim 1, which is for treating colon cancer, wherein said colon cancer is colon carcinoma.

8. The method of claim 1, which is for treating ovarian cancer.

9. The method of claim 1, which is for treating endometrial cancer.

10. The method of claim 1, which is for treating cervical cancer.

11. The method of claim 1, which is for treating uterine cancer.

12. The method of claim 1, which is for treating prostate cancer.

13. The method of claim 1, which is for treating liver cancer.

14. The method of claim 1, which is for treating stomach cancer.

15. The method of claim 1, which is for treating pancreatic cancer.

16. The method of claim 1, which is for treating breast cancer.

17. The method of claim 1, which is for treating colon cancer.

18. The method of claim 1, which is for treating brain cancer.

19. The method of claim 1, which is for treating lung cancer.

20. The method of claim 1, which is for treating skin cancer.

21. The method of claim 1, which is for treating multiple myeloma.

22. The method of claim 1, which is for treating a lymphoma.

23. The method of claim 1, which is for treating leukemia.

* * * * *

SEQUENCE LISTING

```
<160> NUMBER OF SEQ ID NOS: 6

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Psi

<400> SEQUENCE: 1

Gln Trp Ala Val Gly His Xaa Leu Leu
 1               5

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Glp

<400> SEQUENCE: 2

Xaa His Trp Ser Tyr Gly Leu Arg Pro Gly
 1               5                  10
```

```
<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Pyr

<400> SEQUENCE: 3

Xaa His Trp Ser His Gly Trp Tyr Pro Gly
 1               5                  10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Pro Lys Pro Gln Gln Phe Phe Gly Leu Met
 1               5                  10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Nle

<400> SEQUENCE: 5

Asp Ser Phe Val Gly Leu Xaa
 1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Pro Pro Gly Phe Ser Pro Phe Arg
 1               5
```